United States Patent
Zhang et al.

(10) Patent No.: US 10,189,955 B2
(45) Date of Patent: Jan. 29, 2019

(54) NESTED SUPRAMOLECULAR CAPSULES

(71) Applicant: CAMBRIDGE ENTERPRISE LIMITED, Cambridge, Cambridgeshire (GB)

(72) Inventors: Jing Zhang, Cabimbridge (GB); Roger Coulston, Cabimbridge (GB); Richard Parker, Cambridge (GB); Christopher Abell, Cambridge (GB); Oren Scherman, Cambridge (GB); Ziyi Yu, Cambridge (GB)

(73) Assignee: CAMBRIDGE ENTERPRISE LIMITED, Cambridge (GB)

( * ) Notice: Subject to any disclaimer, the term of this patent is extended or adjusted under 35 U.S.C. 154(b) by 0 days.

(21) Appl. No.: 14/763,071

(22) PCT Filed: Jan. 30, 2014

(86) PCT No.: PCT/GB2014/050259
§ 371 (c)(1),
(2) Date: Jul. 23, 2015

(87) PCT Pub. No.: WO2014/118553
PCT Pub. Date: Aug. 7, 2014

(65) Prior Publication Data
US 2015/0368407 A1    Dec. 24, 2015

(30) Foreign Application Priority Data
Jan. 30, 2013    (GB) .................................. 1301648.0

(51) Int. Cl.
*C08G 83/00* (2006.01)
*B01J 13/16* (2006.01)
(Continued)

(52) U.S. Cl.
CPC .......... *C08G 83/008* (2013.01); *A61K 9/4808* (2013.01); *B01J 13/14* (2013.01);
(Continued)

(58) Field of Classification Search
None
See application file for complete search history.

(56) References Cited

U.S. PATENT DOCUMENTS

| 6,911,572 B1 | 6/2005 | Bruhn et al. |
| 7,060,498 B1 | 6/2006 | Wang |

(Continued)

FOREIGN PATENT DOCUMENTS

| CN | 1736367 A | 2/2006 |
| JP | 2007-211060 A | 8/2007 |

(Continued)

OTHER PUBLICATIONS

Zhang et al., One-Step Fabrication of Supramolecular Microcapsules from Microfluidic Droplets, Science 2012, vol. 335, pp. 690-694.*

(Continued)

*Primary Examiner* — Jeffrey D Washville
(74) *Attorney, Agent, or Firm* — Oliff PLC

(57) ABSTRACT

A nested capsule having a first capsule held within a second capsule. Each of the first and second capsules has a shell that is a supramolecular cross-linked network, such as a cucurbituril supramolecular cross-linked network. Each capsule shell is obtained or is obtainable from the complexation of a composition including a host, such as cucurbituril, and one or more building blocks having suitable guest functionality for the host, thereby to form a supramolecular cross-linked network. The nested capsules are suitable for delivering and selectively releasing an encapsulant at a location.

26 Claims, 24 Drawing Sheets

(51) Int. Cl.
  B01J 13/14    (2006.01)
  C08J 3/075    (2006.01)
  B01J 13/22    (2006.01)
  C09B 67/02    (2006.01)
  C09B 69/10    (2006.01)
  A61K 9/48     (2006.01)

(52) U.S. Cl.
  CPC ............. B01J 13/16 (2013.01); B01J 13/22 (2013.01); C08J 3/075 (2013.01); C09B 67/0097 (2013.01); C09B 69/101 (2013.01); C09B 69/103 (2013.01); C09B 69/106 (2013.01); *Y10T 428/2985* (2015.01)

(56) References Cited

U.S. PATENT DOCUMENTS

| | | | |
|---|---|---|---|
| 8,378,059 | B2 | 2/2013 | Rauwald et al. |
| 2002/0022016 | A1* | 2/2002 | Walsh ............... A61K 9/1652 424/93.1 |
| 2002/0133003 | A1 | 9/2002 | Kim et al. |
| 2004/0247680 | A1 | 12/2004 | Farokhzad et al. |
| 2005/0250551 | A1 | 11/2005 | Helle |
| 2005/0250881 | A1 | 11/2005 | Gref et al. |
| 2006/0154254 | A1 | 7/2006 | Kim et al. |
| 2006/0292570 | A1 | 12/2006 | Keinan |
| 2008/0175920 | A1* | 7/2008 | Kim .................... C08G 61/123 424/497 |
| 2008/0199519 | A1 | 8/2008 | Thoenes et al. |
| 2010/0247477 | A1* | 9/2010 | Rauwald ............. C08G 83/008 424/78.3 |
| 2010/0254890 | A1 | 10/2010 | Yang et al. |

FOREIGN PATENT DOCUMENTS

| | | |
|---|---|---|
| KR | 2008/0010168 A | 1/2008 |
| WO | 99/064485 A1 | 12/1999 |
| WO | 05/023816 A2 | 3/2005 |
| WO | 2005/112890 A1 | 12/2005 |
| WO | 07/046575 A1 | 4/2007 |
| WO | 07/106144 A1 | 9/2007 |
| WO | 08/096360 A2 | 8/2008 |
| WO | 2009/071899 A2 | 6/2009 |
| WO | 2011/047870 A1 | 4/2011 |
| WO | 11/077099 A2 | 6/2011 |
| WO | 13/014452 A1 | 1/2013 |
| WO | 2013/124654 A1 | 8/2013 |

OTHER PUBLICATIONS

Yang et al. "Highly Stereoselective Photocyclodimerization of a-Cyclodextrin-Appended Anthracene Mediated by y-Cyclodextrin and Cucurbit[8]uril: A Dramatic Steric Effect Operating Outside the Binding Site". J. Am. Chem. Soc. vol. 130, No. 27, pp. 8574-8575, 2008.
Jun. 20, 2013 International Search Report and Written Opinion issued in International Patent Application No. PCT/GB2013/050414.
May 14, 2012 Search Report issued in Great Britain Patent Application No. GB1202834.6.
Huang et al. "Fabrication of cucurbit[6]uril mediated alginate physical hydrogel beads and their application as a drug carriers". e-Polymers. vol. 95, pp. 1-11, 2008.
Park et al. "In Situ Supramolecular Assembly and Modular Modification of Hyaluronic Acid Hydrogels for 3D Cellular Engineering". ACS Nano. vol. 6, No. 4, pp. 2960-2968, 2012.
Loh et al. "New Biodegradable Thermogelling Copolymers Having Very Low Gelation Concentrations". Biomacromolecules. vol. 8, pp. 585-593, 2007.
Kim et al. "New Cucurbituril Homologues: Syntheses, Isolation, Characterization, and X-ray Crystal Structures of Cucurbit[n]uril (n=5, 7, and 8)". J. Am. Chem. Soc. vol. 122, pp. 540-541, 2000.

U.S. Appl. No. 14/379,109 in the name of Scherman et al., filed Aug. 15, 2014.
Jan. 3, 2012 Ofice Action issued in U.S. Appl. No. 12/734,925.
Jul. 2, 2012 Office Action issued in U.S. Appl. No. 12/734,925.
Appel et al; "Supramolecular Cross-Linked Networks via Host—Guest Complexation with Cucurbit[8]uril;" J. Am. Chem. Soc.; 2010; col. 132; pp. 14251-14260.
Patra et al; "Formation and Size Tuning of Colloidal Microcapsules via Host-Guest Molecular Recognition at the Liquiid-Liquid Interface;" Langmuir; 2009; vol. 25; No. 24; pp. 13852-13854.
Wang et al; "Stepwise Assembly of the Same Polyelectrolytes Using Host-Guest Interaction to Obtain Microcapsules with Multiresponsive Properties;" Chem. Mater.; 2008; vol. 20; pp. 4194-4199.
Hwang et al; "Noncovalent Immobilization of Proteins on a Solid Surface by Cucurbit[7]uril-Ferrocenemethylammonium Pair, a Potential Replacement of Biotin-Avidin Pair;" J. Am. Chem Soc.; 2007; vol. 129; pp. 4170-4171.
Nov. 7, 2011 Search Report issued in British Patent Application No. 1112893.1.
Mar. 14, 2012 Search Report issued in British Patent Application No. 1202127.5.
Nov. 29, 2012 Search Report issued in International Patent Application No. PCT/GB2012/051787.
Nov. 29, 2012 Written Opinion issued in International Patent Application No. PCT/GB2012/051787.
Abraham et al; "Microfluidic Synthesis of Reversibly Swelling Porous Polymeric Microcapsules with Controlled Morphology;" Adv. Mater. 2008; vol. 20; pp. 2177-2182.
Ameloot et al; "Interfacial synthesis of hollow metal-organic framework capsules demonstrating selective permeability;" Nature Chemistry; 2011; vol. 3, p. 382-387.
An et al; pH Controlled Permeability of Lipid/Protein Biometric Microcapsules; Biomacromolecules; 2006; vol. 7; pp. 580-585.
Andrieux et al; "Characterization of Fluorescein Isothiocyanate-Dextrans Used in Vesicle Permeability Studies;" Anal. Chem.; 2002; vol. 74; No. 20; pp. 5217-5226.
Bush et al; "Charge-Mediated Recognition of N-Terminal Tryptophan in Aqueous Solution by a Synthetic Host;" J. Am. Chem. Soc.; 2005; vol. 127; pp. 14511-14517.
Caruso et al; "Nanoengineering of Inorganic and Hybrid Hollow Spheres by Colloidal Templating;" Science; 1998; vol. 282; pp. 1111-1114.
Cavalieri et al; "Assembly and Functionalization of DNA-Polymer Microcapsules;" ACS Nano; 2009; vol. 3; No. 1; pp. 234-240.
Chiefari et al; "Living Free-Radical Polymerization by Reversible Addition-Fragmentation Chain Transfer: The RAFT Process;" Macromolecules; 1998; vol. 31; pp. 5559-5562.
Coulston et al; "Supramolecular gold nanoparticle-polymer composites formed in water with cucurbit[8]uril;" Chem. Commun.; 2011; vol. 47; pp. 164-166.
Cui et al; "Monodisperse Polymer Capsules: Tailoring Size, Shell, Thickness, and Hydrophobic Cargo Loading via Emulsion Templating;" Adv. Funct. Mater.; 2010; vol. 20; 1625-1631.
De Cock et al; "Polymeric Multilayer Capsules in Drug Delivery;" Angew. Chem. Int. Ed.; 2010; vol. 49; pp. 6954-6973.
Donath et al; "Novel Hollow Polymer Shells by Colloid-Templated Assembly of Polyelectrolytes;" Angew. Chem. Int. Ed.; 1998; vol. 37; No. 16; pp. 2201-2205.
Dsouza et al; "Fluorescent Dyes and Their Supramolecular Host/Guest Complexes with Macrocycles in Aqueous Solution;" Chem. Rev.; 2011; vol. 111; pp. 7941-7980.
Duffy et al; "Rapid Prototyping of Microfluidic Systems in Poly(dimethylsiloxan);" Anal. Chem.; 1998; vol. 70; pp. 4974-4984.
Frens et al; "Controlled Nucleation for the Regulation of the Particle Size in Monodisperse Gold Suspensions;" Nature Physical Science; 1973; vol. 241; pp. 20-22.
Garstecki et al; "Formation of droplets and bubbles in a microfluidic T-junction-scaling and mechanism of break-up;" Lab Chip; 2006; vol. 6; pp. 437-446.
Günther et al; "Multiphase microfluidics: from flow characteristics to chemical and materials synthesis;" Lab Chip; 2006; vol. 6; pp. 1487-1503.

(56) References Cited

OTHER PUBLICATIONS

Hermanson et al; "Permeability of silk microcapsules made by the interfacial adsorption of protein;" Phys. Chem. Chem. Phys.; 2007; vol. 9; pp. 6642-6446.
Holtze et al; "Biocompatible surfactants for water-in-fluorocarbon emulsions;" Lab Chip; 2008; vol. 8; pp. 1632-1639.
Huebner et al; "Microdroplets: A sea of applications?;" Lab Chip; 2008; vol. 8; pp. 1244-1254.
Jiao et al; "A Systems Approach to Controlling Supramolecular Architecture and Emergent Solution Properties via Host-Guest Complexation in Water;" J. Am. Chem. Soc.; 2010; vol. 132; pp. 15734-15743.
Jiao et al; "Size Selective Supramolecular Cages from Aryl-Bisimidazolium Derivatives and Cucurbit[8]uril;" Organic Letters; 2011; vol. 13; No. 12; pp. 3044-3047.
Kim et al; "New Cucurbituril Homologues: Syntheses, Isolation, Characterization, and X-ray Crystal Structures of Cucurbit[n]uril (n = 5, 7, and 8);" J. Am. Chem. Soc.; 2000; vol. 122; pp. 540-541.
Lagona et al; "The Cucurbit[n]uril Family;" Angew. Chem. Int. Ed.; 2005; vol. 44; pp. 4844-4870.
Martin et al; "Charged Gold Nanoparticles in Non-Polar Solvents: 10-min Synthesis and 2D Self-Assembly;" Langmuir; 2010; vol. 26; No. 10; pp. 7410-7417.
Moghaddam et al; "New Ultrahigh Affinity Host-Guest Complexes of Cucurbit[7]uril with Bicyclo[2.2.2]octane and Adamantane Guests: Thermodynamic Analysis and Evaluation of M2 Affinity Calculations;" J. Am. Chem. Soc.; 2011; vol. 133; pp. 3570-3581.
Patra et al; "Colloidal Microcapsules: Self-Assembly of Nanoparticles at the Liquid-Liquid Interface;" Chem. Asian J.; 2010; DOI: 10.1002/asia.201000301; pp. 1-13.
Peyratout et al; "Tailor-Made Polyelectrolyte Microcapsules: From Multilayers to Smart Containers;" Angew. Chem. Int. Ed.; 2004; vol. 43; pp. 3762-3783.
Priest et al; "Microfluidic polymer multilayer adsorption on liquid crystal droplets for microcapsule synthesis;" Lab Chip; 2008; vol. 8; pp. 2182-2187.
Rauwald et al; "Correlating Solution Binding and ESI-MS Stabilities by Incorporating Solvation Effects in a Confined Cucurbit[8]uril System;" J. Phys. Chem. B; 2010; vol. 114; pp. 8606-8615.
Rekharsky et al; "Complexation Thermodynamics of Cyclodextrins;" Chem. Rev.; 1998; vol. 98; pp. 1875-1917.
Utada et al; "Monodisperse Double Emulsions Generated from a Microcapillary Device;" Science; 2005; vol. 308; pp. 537-541.
Xu et al; "Preparation of Highly Monodisperse Droplet in a T-Junction Microfluidic Device;" AIChE Journal; 2006; vol. 52; No. 9; pp. 3005-3010.
Yang et al; "Microfluidic assisted synthesis of multi-functional polycaprolactone microcapsules: incorporation of CdTe quantum dots, Fe3O4 superparamagnetic nanoparticles and tamoxifen anticancer drugs;" Lab Chip; 2009; vol. 9; pp. 961-965.
Rauwald et al.; "Supramolecular Block Copolymers with Cucurbit[8]uril in Water;" Angew. Chem. Int. Ed.; 2008; pp. 3950-3953; vol. 47.
Broeren et al.; "Multivalency in the Gas Phase: The Study of Dendritic Aggregates by Mass Spectrometry;" Angew. Chem. Int. Ed.; 2004; pp. 3557-3562; vol. 43.
Osaka et al.; "Characterization of host-guest complexes of cucurbit[n]uril (n=6,7) by electrospray ionization mass spectrometry;" J. Mass Spectrom; 2006; pp. 202-207; vol. 41; John Wiley & Sons, Ltd.
Brunsveld et al.; "Supramolecular Polymers;" Chem. Rev.; 2001; pp. 4071-4097; vol. 101; American Chemical Society.
Knapp et al.; "A Novel Synthetic Strategy toward Soluble, Well-Defined Ruthenium(II) Coordination Polymers," Macromolecules; 1996; pp. 478-480; vol. 29; American Chemical Society.
Kim et al.; "Direct Synthesis of Polymer Nanocapsules with a Noncovalently Tailorable Surface.," Angew. Chem. Int. Ed.; 2007; vol. 46, pp. 3471-3474.
Ligthart et al.; "Supramolecular Polymer Engineering;" Macromolecular Engineering, Precise Synthesis, Materials Properties, Applications; 2007; pp. 351-399.

Nov. 3, 2009 International Search Report issued in International Patent Application No. PCT/GB2008/004016.
Nov. 3, 2009 Written Opinion of the International Search Report issued in International Patent Application No. PCT/GB2008/004016.
Hwang et al, "Noncovalent Immobilization of Proteins on a Solid Surface by Cucurbit[7]uril-Ferrocenemethylammonium Pair, a Potential Replacement of Biotin-Avidin Pair". J. Am. Chem Soc. vol. 129, pp. 4170-4171, 2007.
Appel et al. "Ultrahigh-Water-Content Supramolecular Hydrogels Exhibiting Multistimuli Responsiveness". J. Am. Chem. Soc. vol. 134, pp. 11767-11773, 2012.
Appel et al. "Supramolecular polymeric hydrogels". Chem. Soc. Rev. vol. 41, pp. 6195-6214, 2012.
Benguigui et al. "Homogeneous and inhomogeneous polyacrylamide gels as observed by small angle neutron scattering: A connection with elastic properties". Eur. Phys. J. B. vol. 11, pp. 439-444, 1999.
Biedermann et al. "Postpolymerization Modification of Hydroxyl-Functionalized Polymers with Isocyanates". Macromolecules. vol. 44, pp. 4828-4835, 2011.
Esposito et al. "Comparative analysis of tetracycline—containing dental gels: poloxamer- and monoglyceride-based formulations". International Journal of Pharmaceutics. vol. 142, pp. 9-23, 1996.
Estroff et al. "Water Gelation by Small Organic Molecules". Chem. Rev. vol. 104, No. 3, pp. 1201-1217, 2004.
Greenfield et al. "Tunable Mechanics of Peptide Nanofiber Gels". Langmuir. vol. 26, No. 5, pp. 3641-3647, 2010.
Hartgerink et al. "Self-Assembly and Mineralization of Peptide-Amphiphile Nanofibers". Science. vol. 294, pp. 1684-1688, Nov. 23, 2001.
Heitmann et al. "Sequence-Specific Recognition and Cooperative Dimerization of N-Terminal Aromatic Peptides in Aqueous Solutions by a Synthetic Host". J. Am. Chem. Soc. vol. 128, pp. 12574-12581, 2006.
Horkay et al. "Macroscopic and Microscopic Thermodynamic Observations in Swollen Poly(vinyl acetate) Networks". Macromolecules. vol. 24, pp. 2896-2902, 1991.
Horkay et al. "Structural investigations of a neutralized polyelectrolyte gel and an associating neutral hydrogel". Polymer. vol. 46, pp. 4242-4247, 2005.
Hunt et al. "Tunable, High Modulus Hydrogels Driven by Ionic Coacervation". Adv. Mater. vol. 23, pp. 2327-2331, 2011.
Katakam et al. "Controlled release of human growth hormone following subcutaneous administration in dogs". Int. J. Pharm. vol. 152, pp. 53-58, 1997.
Koopmans et al. "Formation of Physical Hydrogels via Host-Guest Interactions of β-Cyclodextrin Polymers and Copolymers Bearing Adamantyl Groups". Macromolecules. vol. 41, pp. 7418-7422, 2008.
Kretschmann et al. "Switchable Hydrogels Obtained by Supramolecular Cross-Linking of Adamantyl-Containing LCST Copolymers with Cyclodextrin Dimers". Angew. Chem. Int. Edit. vol. 45, pp. 4361-4365, 2006.
Richard et al. "Analysis and Visualisation of Neutron-Scattering Data". J. Neutron Research. vol. 4, pp. 33-39, 1996.
Lee et al. "Unprecedented host-induced intramolecular charge-transfer complex formation". Chem. Comm. pp. 2692-2693, 2002. The Royal Soc. of Chem.
Li et al. "Poly(ester urethane)s Consisting of Poly[(R)-3-hydroxybutyrate] and Poly(ethylene glycol) as Candidate Biomaterials: Characterization and Mechanical Property Study". Biomacromolecules. vol. 6, pp. 2740-2747, 2005.
Loh et al. "Micellization and Thermogelation of Poly(ether urethane)s Comprising Poly(ethylene glycol) and Poly (propylene glycol)". Macromol. Symp. vol. 296, pp. 161-169, 2010.
Loh et al. "Biodegradable Thermogelling Poly[(R)-3-hydroxybutyrate]-Based Block Copolymers: Micellization, Gelation, and Cytotoxicity and Cell Culture Studies". J. Phys. Chem B. vol. 113, pp. 11822-11830, 2009.
Loh et al. "Hydrolytic degradation and protein release studies of thermogelling polyurethane copolymers consisting of poly[(R)]-3-hydroxybutyrate], poly(ethylene glycol), and poly(propylene glycol)". Biomaterials. vol. 28, pp. 4113-4123, 2007.

(56) References Cited

OTHER PUBLICATIONS

Loh et al. "Biodegradable thermogelling polyester urethane)s consisting of polylactic acid)—Thermodynamics of micellization and hydrolytic degradation". Biomaterials. vol. 29, pp. 2164-2172, 2008.
Loh et al. "Synthesis and water-swelling of thermo-responsive poly(ester urethane)s containing poly(e-caprolactone), poly(ethylene glycol) and poly(propylene glycol)". Biomaterials. vol. 29, pp. 3185-3194, 2008.
Loh et al. "Controlled drug release from biodegradable thermoresponsive physical hydrogel nanofibers". J. Contol. Release. vol. 143, pp. 175-182, 2010.
Loh et al. "Encapsulation of basic fibroblast growth factor in thermogelling copolymers preserves its bioactivity." J. Mater. Chem. vol. 21, pp. 2246-2254, 2011.
Lutolf, Matthias. "Spotlight on hydrogels". Nature Materials. vol. 8, pp. 451-453, Jun. 2009.
Mynar et al. "The gift of healing". Nature. vol. 451, pp. 895-896, Feb. 2008.
Nakamura et al. "Supramolecular Catalysis of the Enantiodifference [4+4] Photocyclodimerization of 2-Anthracenecarboxylate by y-Cyclodextrin". J. Am. Chem. Soc. vol. 125, pp. 966-972, 2003.
Nochi et al. "Nanogel antigenic protein-delivery system for adjuvant-free intranasal vaccines". Nat. Mat. vol. 9, pp. 572-578, Jun. 20, 2010.
Peppas et al. "Physicochemical Foundations and Structural Design of Hydrogels in Medicine and Biology". Annu. Rev. Biomed. Eng. vol. 2, pp. 9-29, 2000.
Pezron et al. "Conformation of gelatin chains in aqueous solutions: 1. A light and small-angle neutron scattering study". Polymer. vol. 32, No. 17, pp. 3201-3210, 1991.
Reczek et al. "Multivalent Recognition of Peptides by Modular Self-Assembled Receptors". J. Am. Chem. Soc. vol. 131, pp. 2408-2415, 2009.
Ritger et al. "A Simple Equation for Description of Solute Release I. Fickian and Non-Fickian Release from Non-Swellable Devices in the form of Slabs, Spheres, Cyclinders or Discs". Journal of Contorlled Release. vol. 5, pp. 23-36, 1987.
Staats et al. "Chaperoning vaccines". Nat. Mat. vol. 9, pp. 537-538, Jul. 2010.
Tamaki et al. "Reversible Photodimerization of Water-Soluble Anthracenes included in y-Cyclodextrin." Chem. Lett. pp. 53-56, 1984.
Uzunova et al. "Toxicity of cucurbit[7]uril and cucurbit[8]uril: an explanatory in vitro and in vivo study". Org. Biomol. Chem. vol. 8 No. 9, pp. 2037-2042, May 7, 2010.
Van Tomme et al. "Self-gelling hydrogels based on oppositely charged dextran microspheres". Biomaterials. vol. 26, pp. 2129-2135, 2005.
Wang et al. "High-water-content mouldable hydrogels by mixing clay and a dendritic molecular binder". Nature. vol. 463, pp. 339-343, Jan. 21, 2010.
Wojtecki et al. "Using the dynamic bond to access macroscopically responsive structurally dynamic polymers". Nat. Mat. vol. 10, pp. 14-27, 2011.
Wu et al. "Fabrication of Supramolecular Hydrogels for Drug Delivery and Stem Cell Encapsulation". Langmuir. vol. 24, pp. 10306-10312, 2008.
Biedermann, Frank et al., "Benzobis (imidazolium)-Cucurbit[8]uril Complexes for Binding and Sensing Aromatic Compounds in Aqueous Solutions," Chemistry: A European Journal, vol. 16, pp. 13716-13722, 2010.
Chen, Guosong et al., "Cyclodextrin-based inclusion complexation bridging supramolecular chemistry and macromolecular self-assembly," Chem. Soc. Rev., vol. 40, pp. 2254-2266, 2011.
Chu, Liang-Yin et al., "Preparation of Micron-sized Monodispersd Thermoresponsive Core-Shell Microcapsules," Langmuir, vol. 18, pp. 1856-1864, 2002.

Jeon, Woo Sung et al., "Control of the stoichemetry in host-guest complexation by redox chemistry of guests: Inclusion of methylviologen in cucurbit[8]uril," Chem. Commun., vol. 38, pp. 1828-1829, 2002.
Ke, Hengte et al., "Gold-Nanoshelled Microcapsules: A Theranostic Agent for Ultrasound Contrast Imaging and Photothermal Therapy," Angewandte Chemie, vol. 123, pp. 3073-3077, 2011.
Lan, Yang et al., "A supramolecular route towards core-shell polymeric microspheres in water via cucurbit[8]uril complexation," Chem. Commun., vol. 48, pp. 8757-8759, 2012.
Liu, Yiliu et al., "Host-Enhanced pi-pi Interaction for Water-Soluble Supramolecular Polymerization," Chemistry: A European Journal, vol. 17, pp. 9930-9935, 2011.
Rauwald, Urs et al., ""On-Demand" control of thermoresponsive properties of poly(N-isopropylacrylamide) with cucurbit[8]uril host-guest complexes," Chem. Commun., vol. 47, pp. 6000-6002, 2011.
Waldeck, D. H. et al.,"Photoisomerization Dynamics of Stilbenes," Chem. Rev., vol. 91, pp. 415-436, 1991.
Wu, Jing et al., "Cucurbit[7]uril Complexation Drives Thermal trans-cis-Azobenzene Isomerization and Enables Colorimetric Amine Detection," Chemistry: A European Journal, vol. 15, pp. 11675-11680, 2009.
Wu, Chi et al., "Globule-to-Coil Transition of a Single Homopolymer Chain in Solution," Phys. Rev. Lett., vol. 80, No. 18, pp. 4092-4094, 1998.
Xiao, Wang et al., "Design of a Photoswitchable Hollow Microcapsular Drug Delivery System by Using a Supramolecular Drug-Loading Approach," J. Phys. Chem. B, vol. 115, pp. 13796-13802, 2011.
Yang, Xiao-Chao et al., "Drug Delivery Using Nanoparticle-Stabilized Nanocapsules," Angewandte Chemie, vol. 123, pp. 497-501, 2011.
Zha, Liusheng et al., "Monodisperse Temperature-Sensitive Microcontainers," Advanced Materials, vol. 14, No. 15, pp. 1090-1092, 2002.
Zhang, Jing et al., "One-Step Fabrication of Supramolecular Microcapsules from Microfluidic Droplets," Science, vol. 335, pp. 690-694, 2012.
Zhou, Jinwen et al., "Recent developments in PDMS surface modification for microfluidic devices," Electrophoresis, vol. 31, pp. 2-16, 2010.
Lim et al. "Self-Assembled Ternary Complex of Cationic Dendrimer, Cucurbituril, and DNA: Noncovalent Strategy in Developing a Gene Delivery Carrier". Bioconjugate Chem. vol. 13, pp. 1181-1185, 2002.
Glossary, Drug-Discovery-and-Development, 2012, http:www.dddmag.com/content/glossary-drug-discovery-and-development-terms.
Bosman et al.; "Supramolecular polymers at work;" Materials Today; Apr. 2004; pp. 34-39; vol. 7.
Sijbesma et al.; "Reversible Polymers Formed from Self-Complementary Monomers Using Quadruple Hydrogen Bonding;" Science; Nov. 28, 1997; pp. 1601-1604; vol. 278.
Archer et al.; "Coordination chemistry from monomers to copolymers;" Coordination Chemistry Reviews; 1993; pp. 49-68; vol. 128; Elsevier Sequoia.
Swiegers et al.; "New Self-Assembled Structural Motifs in Coordination Chemistry;" Chem. Rev.; 2000; pp. 3483-3537; vol. 100; American Chemical Society.
Lehn et al.; "Spontaneous assembly of double-stranded helicates from oligobipyridine ligands and copper(I) cations: Structure of an inorganic double helix;" Proc. Natl. Acad. Sci.; Chemistry; May 1987; pp. 2565-2569; vol. 84.
Schütte et al.; "Metallosupramolecular Thin Polyelectrolyte Films;" Angew. Chem. Int. Ed.; 1998; pp. 2891-2893; vol. 37, No. 20; Wiley-VCH Verlag GmbH & Co.
Lohmeijer et al.; "Supramolecular Engineering with Macromolecules: An Alternative Concept for Block Copolymers;" Angew. Chem. Int. Ed.; 2002; pp. 3825-3829; vol. 41, No. 20; Wiley-.
Chen et al; "Ruthenuim Bipyridine-Containing Polymers and Block Copolymers via Ring-Opening Metathesis Polymerization;" Macromolecules; 2004; pp. 5866-5872; vol. 37; American Chemical Society.

(56) References Cited

OTHER PUBLICATIONS

Zhou et al,; "Synthesis and Characterization of Bis(2,2':6'2"-terpyridine)ruthenium(II)-Connected Diblock Polymers via RAFT Polymerization;" Macromolecules; 2005; pp. 4114-4123; vol. 38; American Chemical Society.
Fustin et al.; "Metallo-Supramolecular Block Copolymers," Advanced Materials; 2007; pp. 1665-1673; vol. 19.
Scherman et al.; "Olefin metathesis and quadruple hydrogen bonding: A powerful combination in multistep supramolecular synthesis;" PNAS; Aug. 8, 2006; pp. 11850-11855; vol. 103, No. 32; The National Academy of Sciences of the USA.
Yang et al.; "Supramolecular AB Diblock Copolymers;" Angew. Chem. Int. Ed.; 2004; pp. 6471-6474; vol. 43.
Higley et al.; "A Modular Approach toward Block Copolymers;" Chem. Eur. J.; 2005; pp. 2946-2953; vol. 11.
Yamauchi et al.; "Combinations of Microphase Separation and Terminal Multiple Hydrogen Bonding in Novel Macromolecules;" J. Am. Chem. Soc.; 2002; pp. 8599-8604; vol. 124; American Chemical Society.
Binder et al.; "Supramolecular Poly(ether ketone)-Polyisobutylene Pseudo-Block Copolymers;" Journal of Polymer Science: Part A: Polymer Chemistry; 2004; pp. 162-172; vol. 42; Wiley Periodicals, Inc.
Söntjens et al.; Stability and Lifetime of Quadruply Hydrogen Bonded 2-Ureido-4[1-H]-pyrimidinone Dimers; J. Am. Chem. Soc.; 2000; pp. 7487-7493; vol. 122; American Chemical Society.
Shimizu; "Mini Review-Perspectives on main-chain hydrogen bonded supramolecular polymers;" Polymer International; 2007; pp. 444-452; vol. 56; Society of Chemical Industry.
Behrend et al.; "Justus Liebig's Annalen Der Chemie.;" 1904; pp. 1-37; vol. 339.
Freeman et al.; "Cucurbituril;" J. Am. Chem. Soc.; 1981; pp. 7367-7368; vol. 103; American Chemical Society.
Kim et al.; "Selective Inclusion of a Hetero-Guest Pair in a Molecular Host: Formation of Stable Charge-Transfer Complexes in Cucurbit[8]uril;" Angew. Chem. Int. Ed.; 2001; pp. 1526-1529; vol. 40, No. 8; Wiley-VCH Verlag GmbH.
Sindelar et al.; "Supramolecular Assembly of 2,7-Dimethyldiazapyrenium and Cucurbit[8]uril: A New Fluorescent Host for Detection of Catechol and Dopamine;" Chem. Eur. J.; 2005; pp. 7054-7059; vol. 11.
Jeon et al.; "Supramolecular Amphiphiles: Spontaneous Formation of Vesicles Triggered by Formation of a Charge-Transfer Complex in a Host;" Angew. Chem. Int. Ed.; 2002; pp. 4474-4476; vol. 41, No. 23.
Jeon et al.; "Molecular Loop Lock: A Redox-Driven Molecular Machine Based on a Host-Stablized Charge-Transfer Complex;" Angew. Chem. Int. Ed.; 2005; pp. 87-91; vol. 44.
Ko et al.; "Designed Self-Assembly of Molecular Necklaces Using Host-Stabilized Charge-Transfer Interactions;" J. Am. Chem. Soc.; 2004; pp. 1932-1933; vol. 126; American Chemical Society.
Kim et al.; "Growth of poly(pseudorotaxane) on gold using host-stabilized charge-transfer interaction;" Chem. Commun.; 2004; pp. 848-849; The Royal Society of Chemistry.
Jeon et al.; "A [2]Pseudorotaxane-Based Molecular Machine: Reversible Formation of a Molecular Loop Driven by Electrochemical and Photochemical Stimuli;" Angew. Chem, In, Ed.; 2003; pp. 4097-4100; vol. 42.
Ko et al.; "Supramolecular assemblies built with host-stabilized charge-transfer interactions;" Chem. Commun.; 2007; pp. 1305-1315; The Royal Society of Chemistry.
Moon et al.; "Cucurbit[8]uril-Mediated Redox-Controlled Self-Assembly of Viologen-Containing Dendrimers;" Angew. Chem. Int. Ed.; 2004; pp. 5496-5499; vol. 43.
Wang et al.; "Electrochemical Switching and Size Selection in Cucurbit[8]uril-Mediated Dendrimer Self-Assembly;" Angew. Chem. Int. Ed.; 2006; pp. 7042-7046; vol. 45.
Floudas et al.; "Poly(ethylene oxide-b-isoprene) Diblock Copolymer Phase Diagram;" Macromolecules; 2001; pp. 2947-2957; vol. 34; American Chemical Society.

Sun et al.; "The photoinduced long-lived charge-separated state of Ru(bpy).sub.3-methylviologen with cucurbit[8]uril in aqueous solution;" Chem. Commun; 2006; pp. 4195-4197; The Royal Society of Chemistry.
Jon et al.; "A facile, stereoselective [2+2] photoreaction mediated by cucurbit[8]uril;" Chem. Commun.; 2001; pp. 1938-1939; The Royal Society of Chemistry.
De Greef et al., "Supramolecular Polymerization," Chem. Rev. 2009, 109, pp. 5687-5754.
Li et al., "Self-Assembled Supramolecular Hydrogels formed by biodegradable PEO-PHB-PEO triblock copolymers and a-cyclodextrin for controlled drug delivery," Biomaterials 27 (2006), pp. 4132-4140.
Patra et al., "Colloidal Microcapsules: Self-Assembly of Nanoparticles at the Liquid-Liquid Interface," Chem. Asian J., 2010, 5, pp. 2442-2453.
Anema et al. "Shell-Isolated Nanoparticle-Enhanced Raman Spectroscopy: Expanding the Versatility of Surface-Enhanced Raman Scattering". Annu. Rev. Anal. Chem. vol. 4, pp. 129-150, 2011.
Comiskey et al. "An electrophoretic ink for all-printed reflective electronic displays". Nature. vol. 394, pp. 253-255, Jul. 16, 1998.
Danil de Namor et al. "Thermodynamics of Calixarene Chemistry". Chem. Rev. vol. 98, pp. 2495-2525, 1998.
Forster et al. "Infrared, Ramen and Resonance Ramen Investigations of Methylviologen and its Radical Cation". Journal of Ramen Spectroscopy. vol. 12, No. 1, pp. 36-48, 1982.
Gokel et al. "Crown Ethers: Sensors for Ions and Molecular Scaffolds for Materials and Biological Models". Chem. Rev. vol. 104, pp. 2723-2750, 2004.
Granath, Kirsti. "Solution Properties of Branched Dextrans". Journal of Colloid Science. vol. 13, pp. 308-328, 1958.
Kelly et al. "The Optical Properties of Metal Nanoparticles: The Influence of Size, Shape and Dielectric Environment". J. Phys. Chem. B. vol. 107, pp. 668-677, 2003.
Kola et al., "A detailed description of synthetic and natural polymers which are used in the formulation of sustained release drug delivery system: a review," Journal of Chemical and Pharmaceutical Sciences, vol. 6(3), pp. 161-169, Jul.-Sep. 2013 Issue.
Kwok et al., "Synthetic hydrogels 2. Polymerization induced phase separation in acrylamide systems" Polymer 44 (2003) 7335-7344.
Mehvar, Reza. "Dextrans for targeted and sustained delivery of therapeutic and imaging agents". Journal of Controlled Release. vol. 69, pp. 1-25, 2000.
Nechifor et al., "The Size Distribution of Core Shell Polymeric Capsules as Revealed by Low-Field NMR Diffusometry," Applied Magnetic Resonance, vol. 40, pp. 205-211, Published Online Feb. 12, 2011.
Ritger et al. "A Simple Equation for Description of Solute Release II. Fickian and Anomalous Release from Swellable Devices". Journal of Controlled Release. vol. 5, pp. 37-42, 1987.
Taylor et al. "Precise Subnanometer Plasmonic Junctions for SERS within Gold Nanoparticle Assemblies Using Cucurbit[n]uril 'Glue'". ACS Nano. vol. 5, No. 5, pp. 3878-3887, 2011.
Theberge et al. "Microdroplets in Microfluidics: An Evolving Platform for Discoveries in Chemistry and Biology". Angew. Chem. Int. Ed. vol. 49, pp. 5846-5868, 2010.
Thorsen et al. "Dynamic Pattern Formation in a Vesicle-Generating Microfluidic Device". Physical Review Letters. vol. 86, No. 18, pp. 4163-4166, Apr. 30, 2001.
Kim et al., Direct Synthesis of Polymer Nanocapsules: Self-Assembly of Polymer Hollow Spheres through Irreversible Covalent Bond Formation; J. Am. Chem. Soc., vol. 132(28), pp. 9908-9919; Published (Web): Jun. 24, 2010.
Hans-Peter M. de Hoog et al., "Self-Assembled Architectures with Multiple Aqueous Compartments," Soft Matter, 2012, 8, 4552-4561.
Todd R. Hoare et al., "Hydrogels in Drug Delivery: Progress and Challenges," Polymer 49, (2008), 1993-2007.
Jul. 30, 2013 Office Action issued in Great Britain Application No. GB1301648.0.

* cited by examiner (a) — Outer fluorous oil and [−]-dopant
— Inner fluorous oil and [+]-dopant
— Mixed solution of charged polymers (b) — [+]-polymer diffuses to the [−]-dopant
— [−]-polymer diffuses to the [+]-dopant

Figure 9

| Polymer | 4% Surfactant | 4% Surfactant + 0.2% negative-dopant (carboxylic acid) |
|---|---|---|
| Polymer A Positive (rhodamine-tag) | | |
| Polymer B Negative (FITC-tag) | | |
| Polymer B' Weakly positive (rhodamine-tag) | | |
| Mixed system With CB[8] | | |
| Evaporated droplets | | |
| Rehydrated particles | | |

NESTED SUPRAMOLECULAR CAPSULES

RELATED APPLICATION

This application claims the benefit of and priority to GB 1301648.0 filed on 30 Jan. 2013, the contents of which are hereby incorporated by reference in their entirety.

FIELD OF THE INVENTION

This invention relates to nested capsules, particularly microcapsules, based on a supramolecular, such as cucurbituril-based, cross-linked network, and methods for the preparation of such capsules, and their use in methods of delivering encapsulated components.

BACKGROUND

The microencapsulation of a component by self-assembled hollow microspheres is one of the important aspects of nanotechnology and materials science. Control over the shape and composition of the supporting structure, parameters that influence the material properties, is important for many applications, such as diagnostics, drug delivery, electronic displays and catalysis (see Ke et al. *Angew. Chem.* 2011, 123, 3073; De Cock et al. *Angew. Chem. Int. Ed.* 2010, 49, 6954; Yang et al. *Angew. Chem.* 2011, 123, 497; Comiskey et al. *Nature* 1998, 394, 253; Peyratout et al. *Angew. Chem. Int. Ed.* 2004, 43, 3762). Preparation of conventional polymeric microcapsules proceeds via a layer-by-layer (L-b-L) scheme, where a solid support is coated by the sequential addition of a series of oppositely charged polyelectrolyte layers (see Caruso et al. *Science* 1998, 282, 1111; Donath et al. *Angew. Chem. Int. Ed.* 1998, 37, 2201). This strategy provides a uniform material but suffers from reduced encapsulation efficiencies due to the solid template. An alternative method utilises colloidal emulsion-templating where liquid-liquid interfaces drive the self-assembly of shell components (see Cui et al. *Adv. Funct. Mater.* 2010, 20, 1625). However, it is difficult to control monodispersity and material diversity of the resulting microcapsules, thereby limiting its functionality in drug delivery and sensing applications.

In contrast, microfluidic droplets, a subset of colloidal emulsion, have shown great promise for microcapsule fabrication (see Gunther et al. *Lab Chip* 2006, 6, 1487; Huebner et al. *Lab Chip* 2008, 8, 1244; Theberge et al. *Angew. Chem. Int. Ed.* 2010, 49, 5846). These droplets of narrow size distribution (polydispersity index <2%) can be generated at extremely high frequency with economic use of reagents (see Xu et al. *AIChE Journal* 2006, 52, 3005). Initial efforts to prepare capsules based on microdroplet-assisted fabrication have focused on phase separation using double emulsion and liquid crystal core templating (see Utada et al. *Science* 2005, 308, 537; Priest et al. *Lab Chip* 2008, 8, 2182). The formation of polymeric capsule walls has also been described in an approach that involves microfluidic device surface treatment and rapid polymerization techniques (see Zhou et al. *Electrophoresis* 2009, 31, 2; Abraham et al. *Advanced Materials* 2008, 20, 2177). The wall is formed as the solvent evaporates from formed organic solvent droplets. Metal-organic framework capsules have also been recently reported (see Ameloot et al. *Nat. Chem.* 2011, 3, 382). With the current ionic or covalent cross-linking strategies, however, the main challenge in capsule fabrication lies in the simultaneous production of uniform capsules with high cargo loading efficiencies and facile incorporation of diverse functionality into the capsule shell.

The present inventors have now established a capsule based on a cucurbituril-based host-guest network. Designing microstructures using multivalency and cooperativity through molecular recognition provides an unparalleled opportunity in the fabrication of microcapsules with tailorable interactions and functionalities. However, efforts in preparing microcapsules using supramolecular host-guest approach, as described herein, are scarce (see De Cock et al. *Angew. Chem. Int. Ed.* 2010, 49, 6954).

Previous disclosures include a colloidal microcapsule comprising β-cyclodextrin and modified gold nanoparticles (AuNPs) prepared via emulsion templating (Patra et al., *Langmuir* 2009, 25, 13852), and a microcapsule comprising polymers functionalized with cyclodextrin and ferrocene prepared using a L-b-L synthesis (Wang et al., *Chemistry of Materials* 2008, 20, 4194).

Some of the present inventors have described the preparation of capsules, particularly microcapsules, based on a cucurbituril cross-linked network (see Zhang et al. *Science* 2012, 335, 690; and WO 2013/014452), the contents of which are hereby incorporated by reference in their entirety. This work does not describe or teach the use of nested capsules.

SUMMARY OF THE INVENTION

The present invention provides a nested capsule comprising a first capsule held within a second capsule, and each of the first and second capsules has a shell of material that is a supramolecular cross-linked network.

The second capsule may hold one or more first capsules. In one embodiment, the second capsule holds two, three, four or five first capsules.

The supramolecular cross-linked network includes a non-covalent complex of a host, such as cucurbituril, and one or more building blocks comprising suitable guest functionality. The guests are non-covalently held by the host, for example in a cavity of the host. Thus, the complex non-covalently crosslinks the building block and/or non-covalently links the building block to another building block thereby forming the network.

In one embodiment, the shell of the second capsule has a different reactivity to the shell of the first capsule.

In one embodiment, the network of the first capsule is different to the network of the second capsule.

In one embodiment, the network of the second capsule includes a building block, such as a polymer, that is different to a building block present in the network of the first capsule.

In one embodiment, the complex present in the network of the second capsule is different to the complex present in the network of the first capsule. In one embodiment, the guests are different.

In one embodiment, the host is selected from cucurbituril, cyclodextrin, calix[n]arene, and crown ether compounds.

In one embodiment, the host is capable of forming a ternary host-guest complex.

In one embodiment, the host is a cucurbituril compound.

In one embodiment, the host is CB[8].

In a further embodiment of the invention there is provided a nested capsule as described above, holding an encapsulant. The encapsulant may be held in the first capsule. The encapsulant may be held in the second capsule. An encapsulant may also be provided in both the first and second capsules.

In one embodiment, the nested capsule holds a first encapsulant and a second encapsulant, wherein the first encapsulant is held by the first capsule, and the second encapsulant is held by the second capsule. The first and second encapsulants may be the same or different.

In one embodiment, the second capsule is held within a third capsule, and the third capsule has a shell of material that is a supramolecular cross-linked network. The third capsule may hold one or more second capsules. In one embodiment, the third capsule holds two, three, four or five second capsules. In further embodiment, the nested capsule is provided with fourth, fifth, tenth, twentieth or more capsules, with each capsule holding one or more capsules of a lower generation.

The first capsule may hold a first encapsulant. The second capsule may hold a second encapsulant, which is not held in the first capsule. The shell of the first capsule may prevent the first and the second encapsulants from interacting. The shell of the second capsule may prevent the release of the second encapsulant from the second capsule. The shell of the second capsule may prevent the release of the first capsule from the second capsule. The shell of the second capsule may prevent the release of the first encapsulant from the second capsule.

In a further aspect of the invention there is provided a method for the preparation of a nested capsule, the method comprising the steps of:
  (i) providing a first capsule, wherein the first capsule has a shell that is a supramolecular cross-linked network;
  (ii) encapsulating the first capsule within a shell of a second capsule, wherein the shell of the second capsule is a supramolecular cross-linked network, thereby to form a nested capsule.

Also provided is a further method for the preparation of a nested capsule, the method comprising the steps of:
  (i) providing a first droplet within a second droplet, wherein each of the first and second droplets has at its interface components suitable for forming a shell that is a supramolecular cross-linked network;
  (ii) permitting the components at the interfaces of the first and the second droplet to form a supramolecular cross-linked network, thereby to form a nested capsule.

In a further aspect, the present invention provides a method of delivering a component to a location, the method comprising the steps of:
  (i) providing a nested capsule of the invention, which hold an encapsulant;
  (ii) delivering the nested capsule to a location; and
  (iii) permitting release of the encapsulated component from the nested capsule at the location.

In one embodiment, the encapsulant is held in the first capsule or the second capsule or both.

In a further aspect, the present invention provides a method of delivering a plurality of encapsulants to one or more locations, the method comprising the steps of:
  (i) providing a nested capsule of the invention, the nested capsule comprising a first capsule held within a second capsule, and each of the first and second capsules having a shell of material that is a supramolecular cross-linked network, wherein the first capsule holds a first encapsulant and the second capsule holds a second encapsulant;
  (ii) delivering the nested capsule to a location;
  (iii) permitting release of the second encapsulant from the second capsule at a first location; and
  (iv) subsequently permitting release of the first encapsulant from the first capsule at the first location or a second location.

In a related aspect, the present invention provides a method of delivering a plurality of components to a location, the method comprising the steps of:
  (i) providing a nested capsule of the invention, the nested capsule comprising a first capsule held within a second capsule, and each of the first and second capsules having a shell of material that is a supramolecular cross-linked network, wherein the first capsule holds a first encapsulant and the second capsule holds a second encapsulant;
  (ii) delivering the nested capsule to a location; and
  (iii) permitting release of the second encapsulant from the second capsule at a first location and simultaneously permitting release of the first encapsulant from the first capsule, thereby to deliver the first and second encapsulants to the location.

In another aspect, the present invention provides a method of synthesis, the method comprising the steps of:
  (i) providing a nested capsule of the invention, the nested capsule comprising a first capsule held within a second capsule, and each of the first and second capsules having a shell of material that is a supramolecular cross-linked network, wherein the first capsule holds a first encapsulant and the second capsule holds a second encapsulant;
  (ii) permitting release of the first encapsulant from the first capsule into the second capsule, thereby to permit the first encapsulant to interact with the second encapsulant to yield a product; and
  (iii) optionally permitting the release of the product from the second capsule.

In an alternative aspect of the invention, a shell of a capsule in the nested capsule is a network formed from the covalent crosslinking of a building block and/or the covalent linking of a building block to another building block thereby forming the network. A host is non-covalently linked to a building block. More particularly, the covalent linkages may be formed between guests of the building block or blocks. The product formed from the covalent linking of building blocks may be non-covalently held by the host.

A capsule provided in the nested capsule of the invention may have a shell of material that has non-covalent and covalent linkages as described above.

A nested capsule of the invention may have a capsule where the shell comprises covalent linkages as described above. In one embodiment, another capsule in the nested capsule of the invention may comprise non-covalent linkages as described above. In an alternative embodiment, the another capsule may also have a shell comprising covalent linkages as described above.

Also provided by the invention is a capsule having a shell that is a covalently cross-linked network, wherein the network is obtainable from a supramolecular cross-linked network by the ternary complexation of a composition comprising a host and one or more building blocks having suitable guest functionality, thereby to form a supramolecular cross-linked network, wherein the covalent cross-links are obtainable from the reaction of the guests held in the ternary complex.

In another aspect of the invention there is provided a capsule having a shell of material that is a supramolecular and a covalent cross-linked network.

In one aspect of the invention there is provided a method of synthesising a nested capsule, the method comprising the steps of:
  (i) forming a first droplet of a first fluid in a continuous phase of a second fluid;

(ii) forming a second droplet of the second fluid in a continuous phase of a third fluid, wherein the second droplet contains the first droplet or a capsule obtained therefrom;

(iii) providing a first building block having guest functionality at the interface of the first fluid and the second fluid, and permitting the first building block to complex with a host at the interface;

(iv) providing a second building block having guest functionality at the interface of the second fluid and the third fluid, and permitting the first building block to complex with a host at the interface.

SUMMARY OF THE FIGURES

FIG. 7(a) shows the even distribution of the charged polymers in the second droplet immediately after formation of the double emulsion droplet; and FIG. 7(b) shows the double emulsion droplet after the charged polymers have diffused to the droplets boundaries of opposite charge. Differential charging of the two oil-water interfaces controls the diffusion of a polymer to the inner or outer interface. Through use of a mixture of both positively and negatively charged polymers, this discriminatory effect will allow for the formation of disparate polymer capsules.

FIG. 9 is a collection of micrographs showing the distribution of a rhodamine-tagged positively charged polymer A (PVA-Rhod-MV), a FITC-tagged negatively-charged (PHEAm-FITC-Azo) polymer B and a weakly positively charged polymer B' (PVA-Rhod-Stil), with and without a CB[8] host in a single emulsion droplet. The continuous phase is provided with 4 wt % of surfactant and optionally 0.2 wt % of a negative dopant. Polymer A can form a complex with both polymers B and B' in the presence of CB[8]. In a mixed system, it is found that polymer A will complex exclusively with the polymer offering the same interfacial properties; polymer B when the droplet interface is neutral (leading to microspheres) and polymer B' when it is negatively charged (leading to microcapsules).

the chemical structures and schematic representations of the photochemistry of the trans-azobenzene-functionalized copolymer 19E and its cis-isomer 19Z; (c) the UV-vis spectra of an aqueous solution of 19E ($3.7\times10^{-7}$M, [trans-azobenzene]=$1.84\times10^{-4}$ M) after it was exposed to irradiation using 350 nm light at various time intervals; (d) The optical microscope images of dried AuNP-embedded microcapsules; and (e) a schematic of the microcapsule obtained from a compositions comprising copolymer 19E, $MV^{2+}$-AuNP 3c, and CB[8] ([transazobenzene]=[$MV^{2+}$]=CB[8]=$6.1\times10^{-5}$ M).

Figure 14:
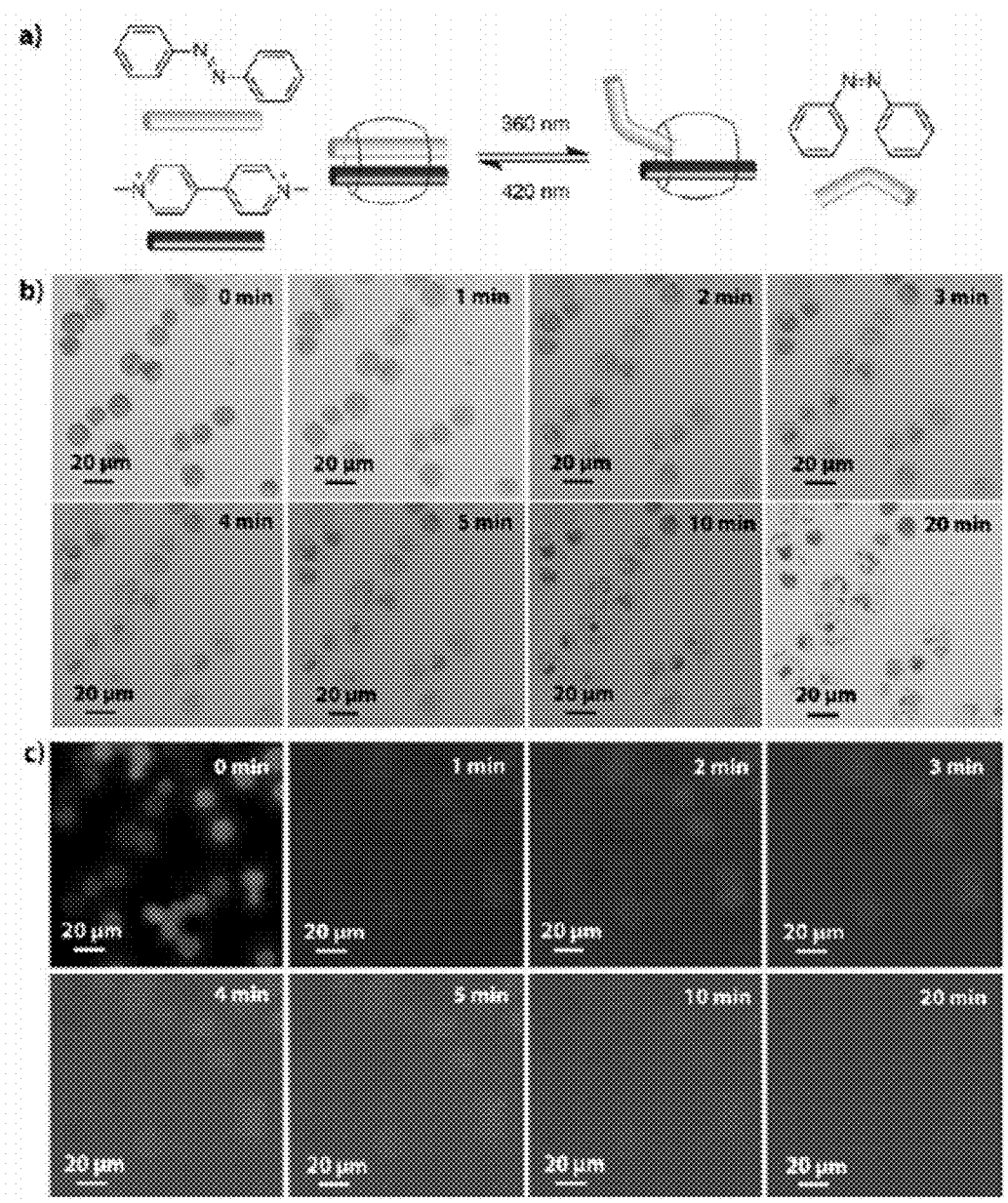

FIG. 14 is (a) a schematic representation of the disruption of the [(trans-azobenzene)(MV2+)⊂CB[8]] ternary complex on account of the photochemistry-induced spatial change in the trans-azobenzene moiety; (b) the bright field images of the rehydrated AuNP-containing microcapsules after irradiation using 360 nm light for various time intervals; and (c) the corresponding fluorescence images of the rehydrated AuNP-embedded microcapsules after irradiation using 360 nm light for various time intervals. The microcapsules were prepared from copolymer 19E, $MV^{2+}$-AuNP 3c, and CB[8] ([trans-azobenzene]=[$MV^{2+}$]=CB[8]=$6.1\times10^{-5}$ M).

Figure 15:
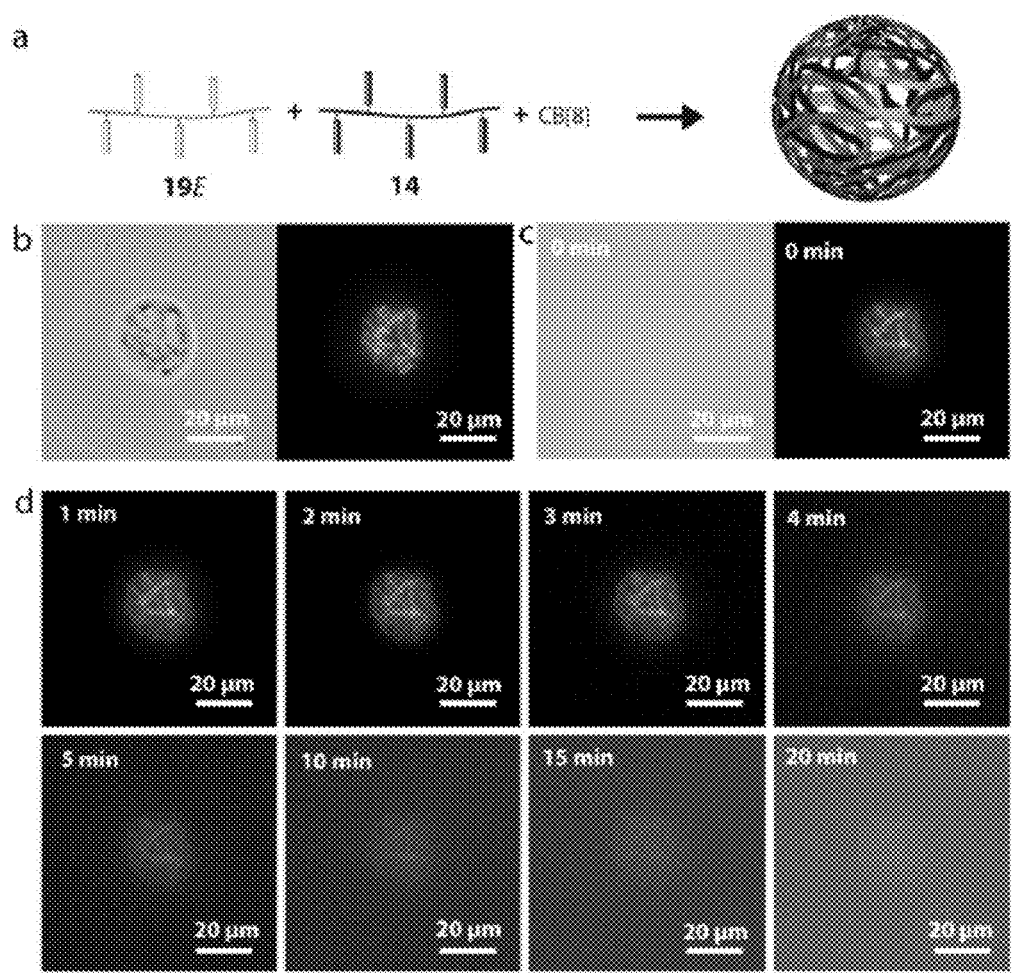

FIG. 15 is (a) a schematic representation of a microcapsule obtained from a composition comprising copolymer 19E, $MV^{2+}$-containing copolymer 14, and CB[8] ([trans-azobenzene]=[$MV^{2+}$]=CB[8]=$6.1\times10^{-5}$ M), containing 500 kDa FITC-dextran ($1.3\times10^{-6}$ M); (b) the bright field and fluorescence images of the dehydrated polymeric microcapsules containing a 500 kDa FITC-dextran as encapsulant; (c) the bright field and fluorescence images of the rehydrated polymeric microcapsules containing 500 kDa FITC-dextran as encapsulant; and (d) the fluorescence images of the rehydrated polymeric microcapsules after irradiation using 360 nm light for various time intervals from 0 minutes to 20 minutes.

Figure 16:
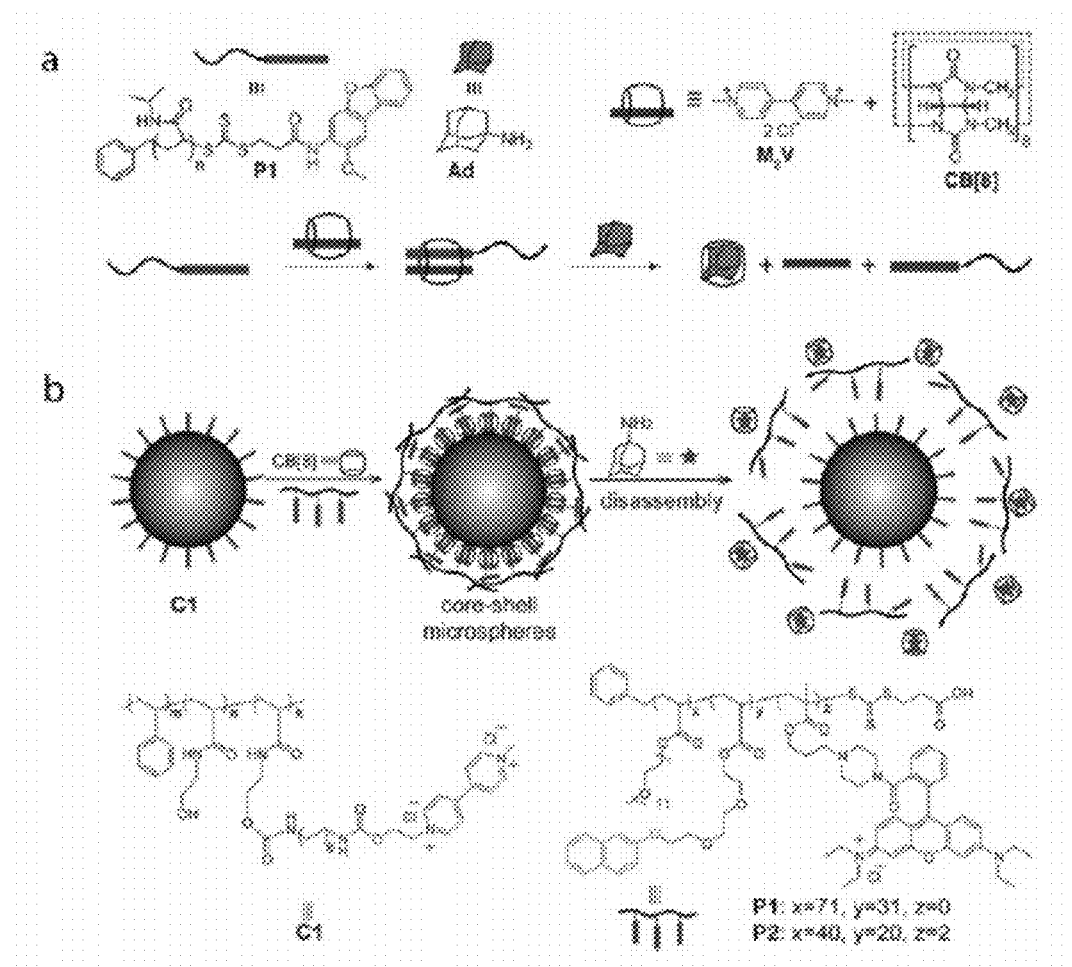

FIG. 16 is (a) a schematic of a chain-end complexation of end functionalized PNIPAm with [(MV2+)⊂CB[8]] followed by disruption of the ternary complex in the presence of 1-aminoadamantane. Reproduced from Rauwald et al. *Chem. Comm.* 2011, 47, 6000; and (b) reversible preparation of core-shell polymeric microspheres via the formation and dissociation of CB[8] ternary complex using 1-adamantamine. Reproduced from Lan et al. *Chem. Comm.* 2012, 48, 8757.

Figure 17:
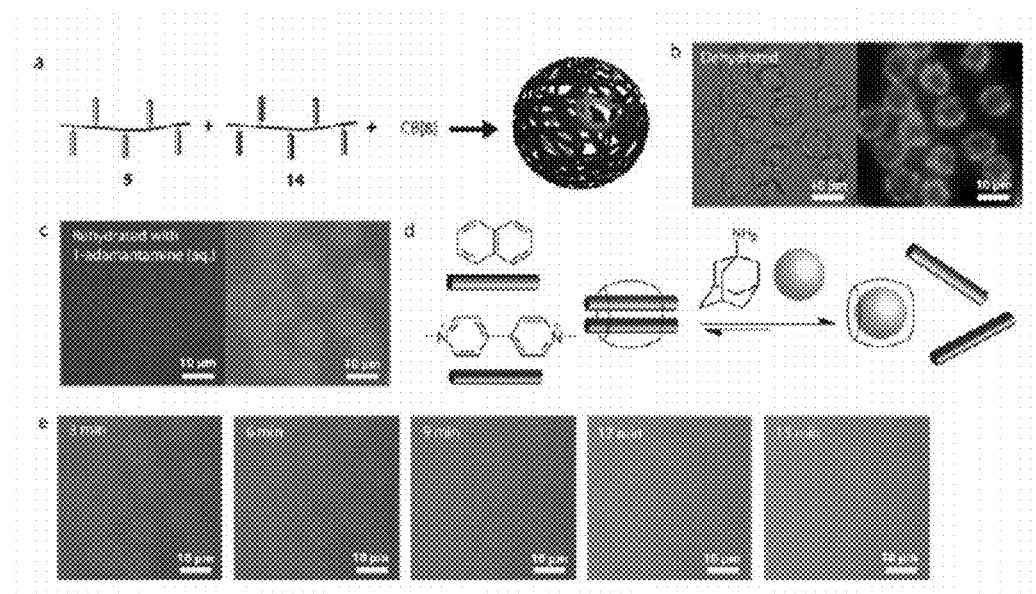

FIG. 17 is (a) a schematic representation of the formation of the a microcapsule from copolymers 5, 14 and CB[8]; (b) The bright field and fluorescence images of the dehydrated microcapsules containing a 500 kDa FITC-dextran encapsulant; (c) the bright field and fluorescence images of the loaded microcapsules redispersed in an aqueous solution of 1-adamantamine (100 µM); (d) a schematic representation of the disruption of the [(naphthol)($MV^{2+}$)⊂CB[8]] ternary complex by 1-adamantamine; and (e) fluorescence images of the adamantamine-immersed microcapsules over time showing the steady release of the FITC-labelled cargo.

Figure 18:
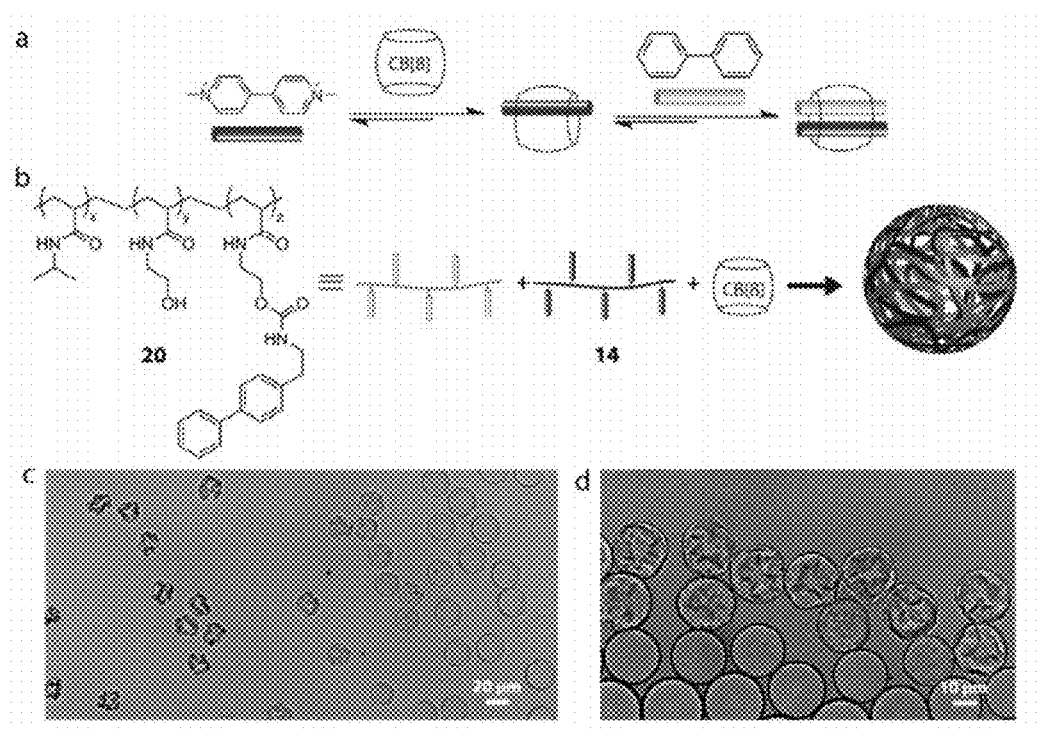

FIG. 18 is (a) schematic representation of the formation of the [(MV2+)(biphenyl)⊂CB[8]] ternary complex; (b) the chemical structure of the biphenyl-containing PNIPAm-based copolymer 20, and the schematic representation of the formation of the polymeric microcapsule from copolymers 14, 20 and CB[8]; (c) the bright field microscope image of the dehydration process of the microdroplet precursors; and (d) a close-up image of the morphology of the transformation from microdroplets to polymeric microcapsules. The microcapsules were prepared from microdroplets containing an aqueous mixture of 20, 14 and CB[8] ([biphenyl]=[$MV^{2+}$]=CB[8]]=$3\times10^{-5}$ M).

Figure 19:
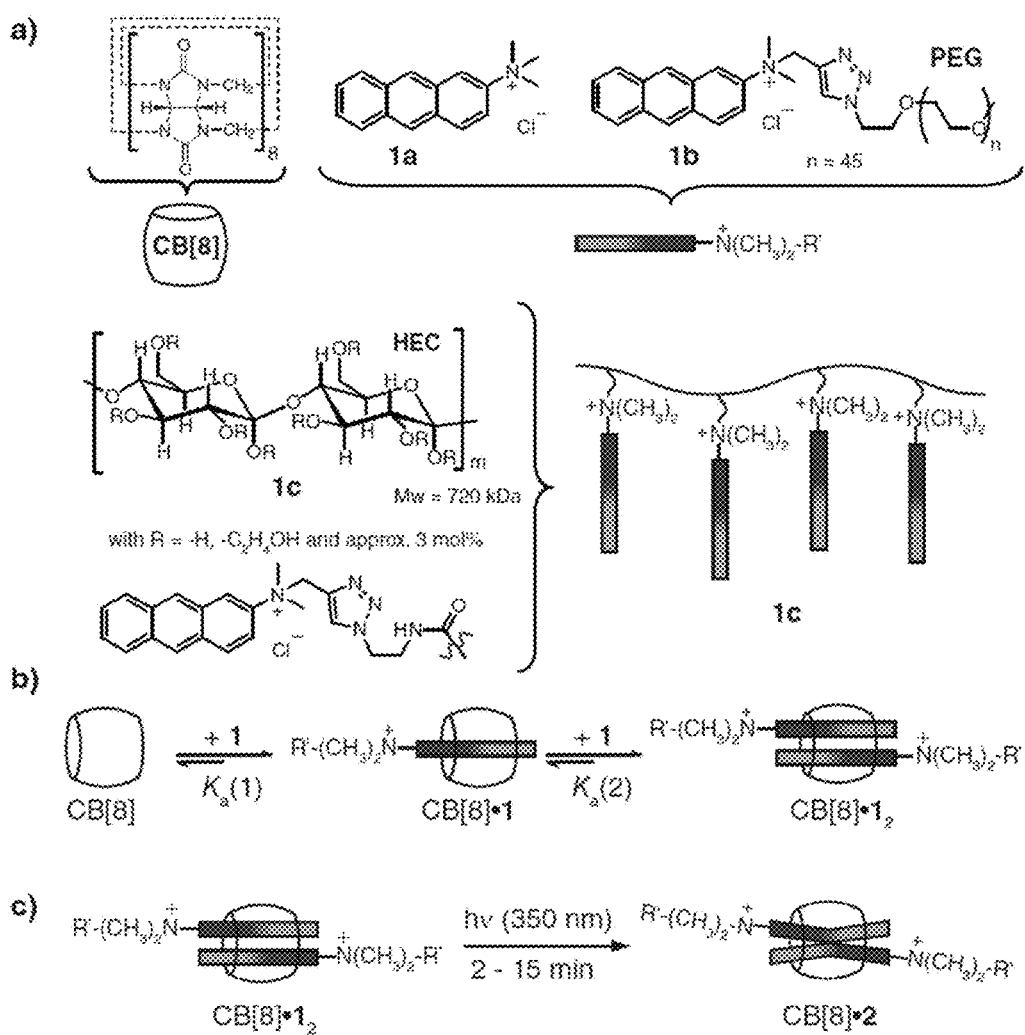

FIG. 19 shows (a) the chemical structures of compounds used in the dimerisation study: CB[8], small-molecule cationic anthracene-species 1a and its macromolecular analogues 1b (end-group functionalised poly(ethylene glycol) polymer, PEG) and 1c (side-chain functionalised hydroxyethyl cellulose, HEC); b) a reaction schematic of CB[8] "handcuffing" together two anthracene-moieties in a face-to-face π-π-stack to form a 1:2 homoternary complex in water; and (c) a reaction schematic of the photoirradiation of the 1:2 ternary complex with a 350 nm light-source leads to nearly quantitative [4+4] photodimerisation within minutes.

Figure 20:
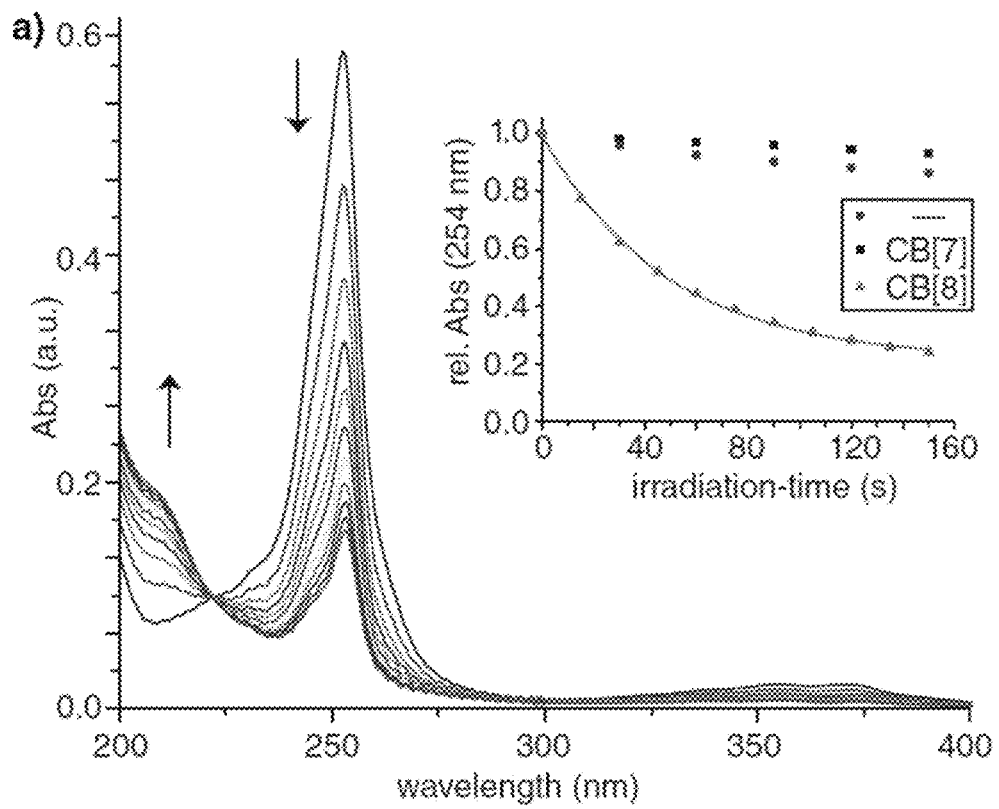
Figure 20:
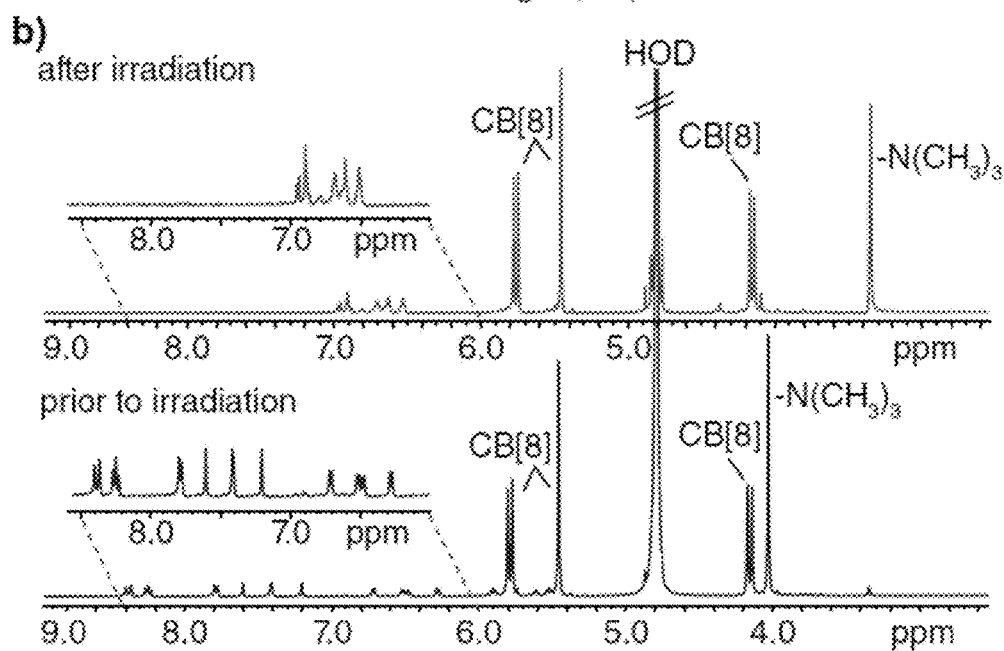

FIG. 20 (*a*) is a UV/vis spectra of a 1a (10 µM) in presence of 0.5 equiv. CB[8] in $H_2O$ upon photoirradiation with a 350 nm light source, spectra taken 15 sec apart. The inset shows the kinetic data in comparison to the control experiments in the absence of the CB[8] host, and in the presence of CB[7]. The solid line shows the best monoexponential fit of the kinetic data. FIG. 20 (*b*) is a $^1$H NMR spectrum of CB[8]•1a₂ (500 µM in $D_2O$) prior to (bottom) and after (top) photoirradiation for 15 minutes. The insets show the aromatic peak region.

Figure 21:
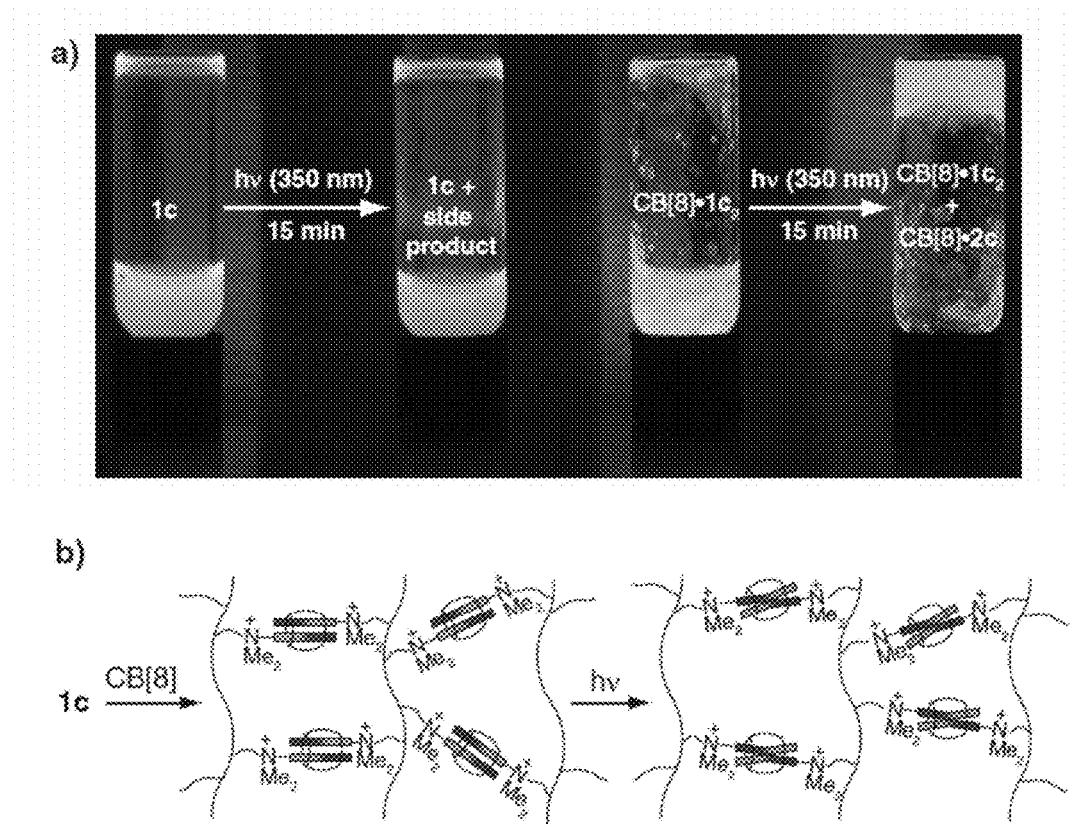

FIG. 21(*a*) is a series of photographs of 1c at 1.0 wt % in $H_2O$. From left to right: 1c prior to photoirradiation; after photoirradiation at 350 nm for 15 minutes; 1c in the presence of CB[8] (0.5 equiv. per anthracene moiety); after photoirradiation at 350 nm for 15 minutes.

FIG. 21(*b*)) is a schematic representation of non-covalent network formation (gelation) upon addition of CB[8] to 1c followed by photocrosslinking through anthracene dimerisation.

Figure 22:
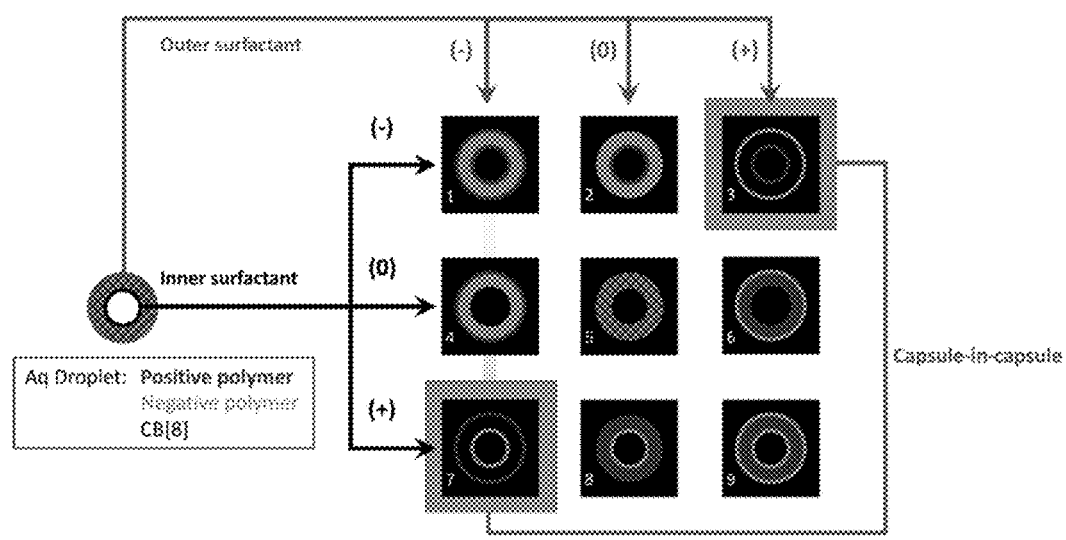

FIG. 22 is a schematic showing the possible capsule structures that may be formed using charged building blocks (+ and −) and charged (+ and −) and uncharged (0) surfactants. It is possible to prepare nested capsules of the invention by selective attraction of building blocks to the solvent interfaces of nested droplets.

Figure 23:
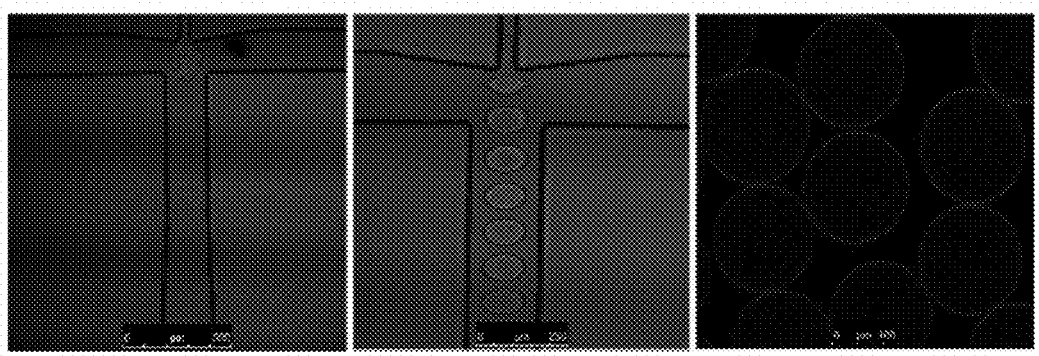

FIG. 23 is a series of three laser scanning confocal micrographs of droplet generation, demonstrating the rapid diffusion of a positively-charged polymer (rhodamine-tagged) to the oil-water interface after droplet generation in the presence of a negatively-charged surfactant in the oil continuous phase. After traveling less than 4 mm within the microfluidic channel, the diffusion to the interface was complete (right image).

Figure 24:
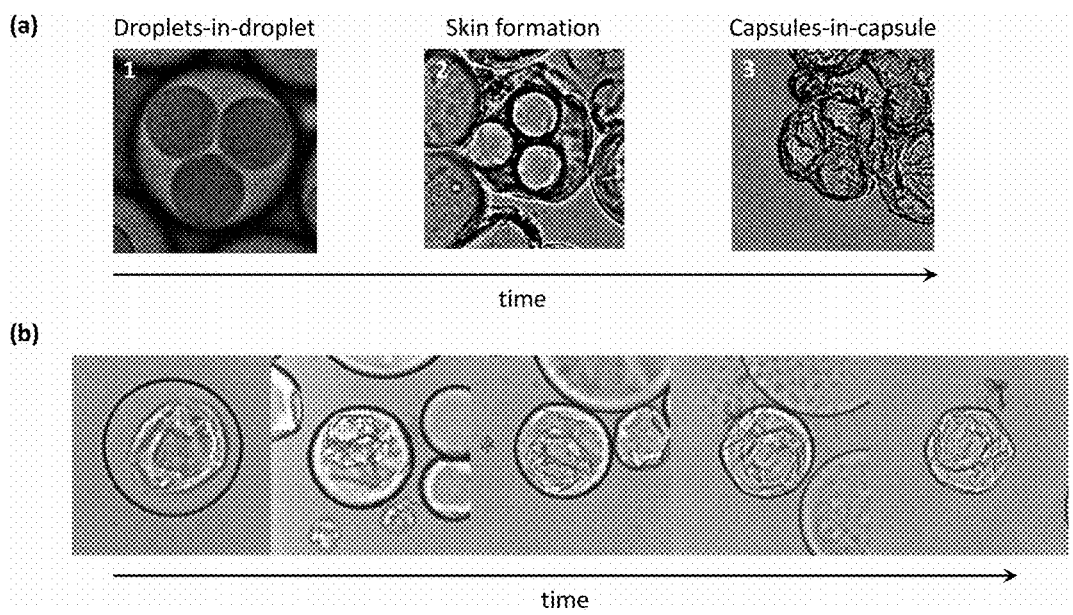

FIG. 24 is a series of micrographs showing the formation of nested microdroplets in an (a) oil-water-oil and (b) chloroform-water-oil system. The micrographs show the subsequent formation of a nested capsule from the nested microdroplets upon complexation of a CB[8] host with polymeric molecules having suitable guest functionality (RC-PVA-Rhod-MV and RC-PVA-Rhod-Stil).

Figure 25:
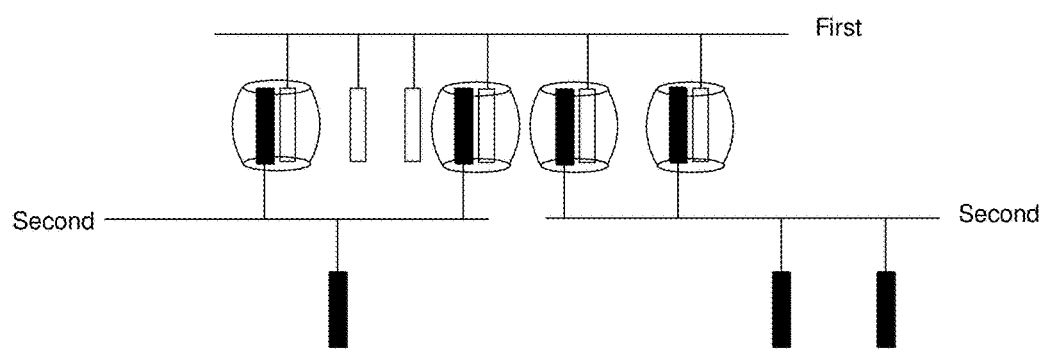
Figure 26:
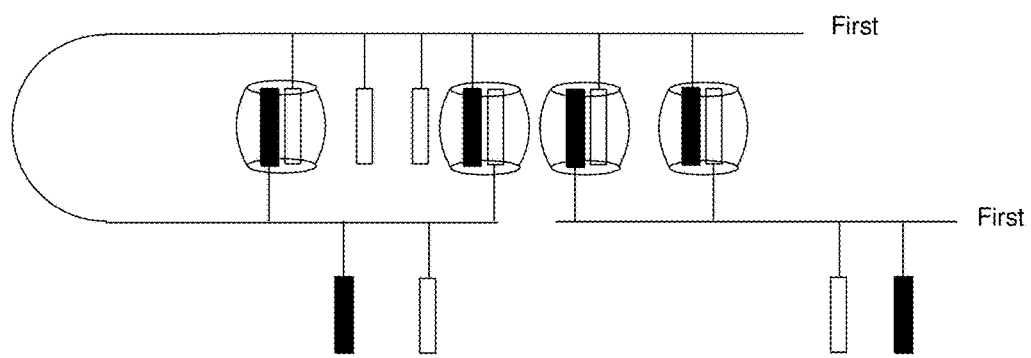

FIG. 25 is a schematic representation of some of the first guest molecules (unshaded rectangles) of the first building block are in complex with the hosts (barrels) and second guest molecules (shaded rectangles) of the second building blocks FIG. 26 is a schematic representation of a basic network formed between a host and two single first building blocks each having a plurality of first and second guest molecules.

Figure 27:
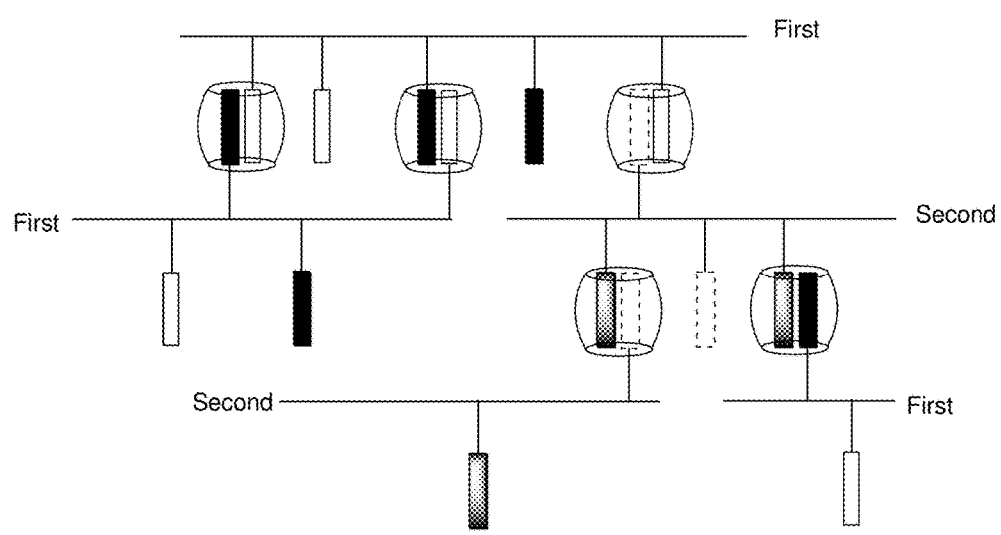
Figure 28:
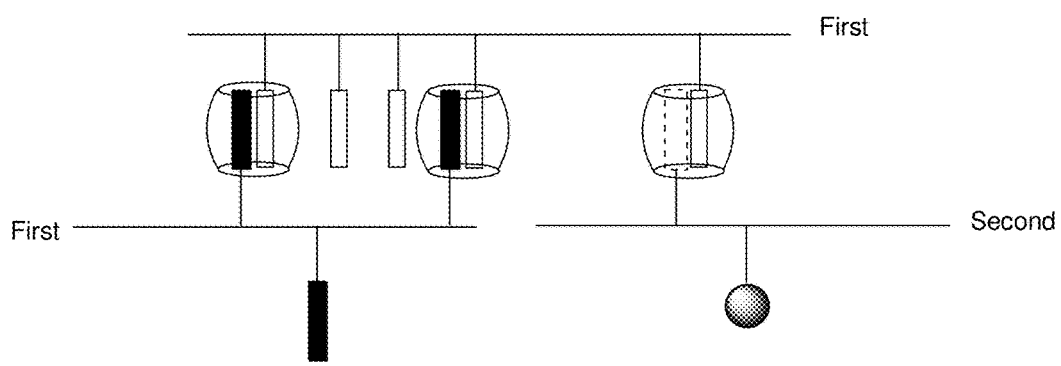

FIG. 27 is a schematic representation of a basic network formed between the host, three single first building blocks each having a plurality of first and second guest molecules, and two second building blocks each having a plurality of third and fourth guest molecules FIG. 28 is a schematic representation of a basic network formed between cucurbituril, two single first building blocks each having a plurality of first and second guest molecules, and also including a single second building block, which is covalently linked to one fourth guest molecule, and a detectable label.

Figure 29:
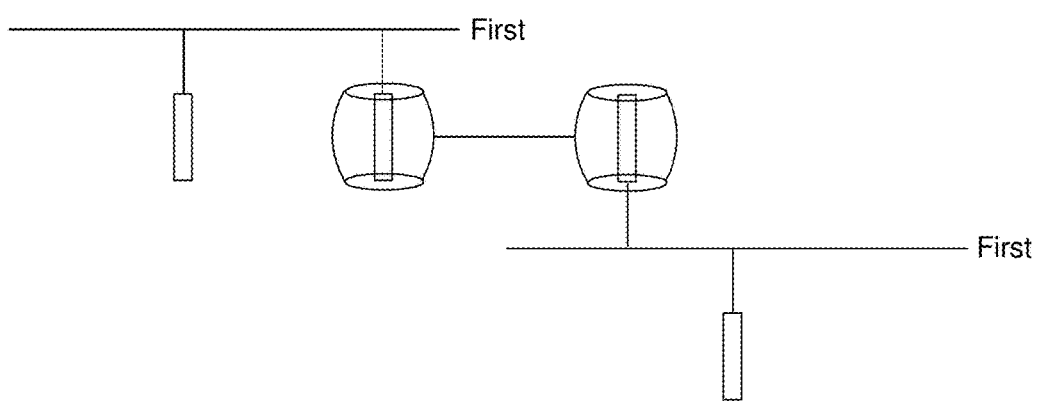

FIG. 29 is a schematic representation of a basic network formed between a plurality of covalently linked hosts and two single first building blocks each having a plurality of first guest molecules.

Figure 30:
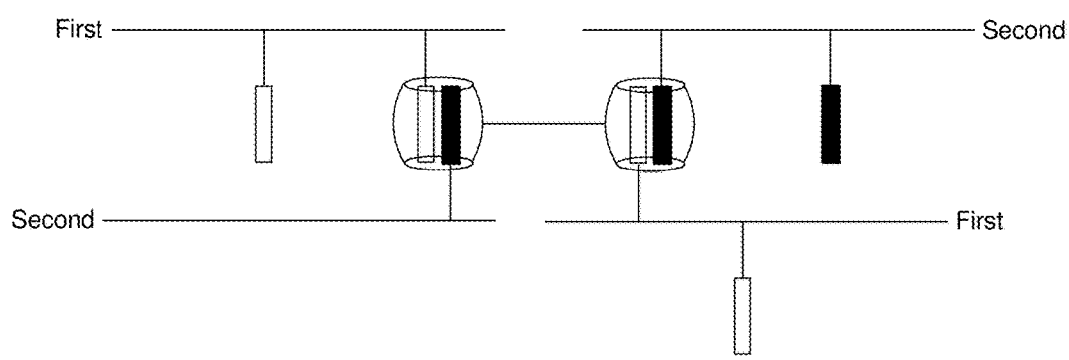
Figure 31:
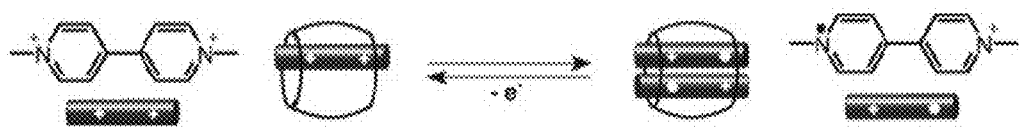

FIG. 30 is a schematic representation of a basic network formed between a plurality of covalently linked hosts, two single first building blocks each having a plurality of first guest molecules, and two single second building blocks each having a plurality of second guest molecules, FIG. 31 is a schematic representation the formation of a 2:1 $[(MV^{+\bullet})_2 \subset CB[8]]$ complex consisting of CB[8] and two molecules of methyl viologen cationic radical $(MV^{+\bullet})$.

Figure 32:
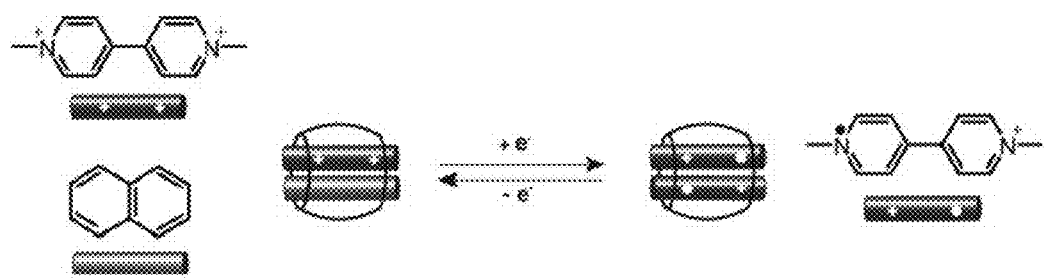

FIG. 32 is a schematic representation the preferential formation of the 2:1 $[(MV^{+\bullet})_2 \subset CB[8]]$ inclusion complex over the $[(MV^{2+})(naphthol) \subset CB[8]]$ ternary complex in the presence of a reducing agent.

DETAILED DESCRIPTION OF THE INVENTION

The present invention provides a nested capsule comprising a first capsule held within a second capsule, and each of the first and second capsules has a shell of material that is a supramolecular cross-linked network. The supramolecular cross-linked network includes a non-covalent complex of a host, such as cucurbituril, and one or more building blocks comprising suitable guest functionality.

Figure 1:
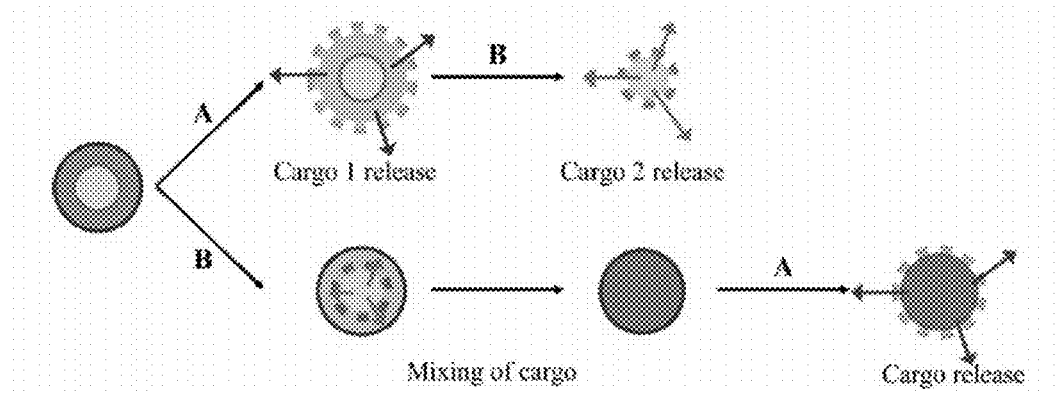
FIG. 1 is a schematic of two alternative release mechanisms for a nested capsule having a first capsule held by a second capsule according to an embodiment of the invention. Each of the capsules holds an encapsulant (cargo). The encapsulants may be released sequentially from the nested capsule (top route) or the encapsulants may be permitted to interact prior to their release, by degradation of the first (inner) capsule prior to the degradation of the second capsule (bottom route)

The application of supramolecular host-guest chemistry to a nested capsule provides a system that is dynamic, with a range of stimuli offering the potential to degrade the capsule shell, thereby to release the capsule contents (or cargo). Examples of release stimuli include light, pH, redox chemistry, temperature and competitive molecules. With the capsule-in-capsule morphology, the multi-component nature of such storage offers the advantages of more elaborate release mechanisms, including but not limited to multi-stage triggered release, pre-mixing before release, and dual-parameter release whereby several conditions must all be met before release occurs. Examples of such release mechanisms are illustrated in FIG. 1, whereby the sequential exposure to stimuli A and B can lead to either the step-wise triggered release of two cargoes held in first and second capsules, or to the mixing of the two cargoes within the capsule prior to release. This second pathway also offers the opportunity for the study of interactions between the different cargoes whilst they are still confined to the localised capsule environment.

Some of the inventors have described in WO 2009/071899 the preparation of polymer systems where a polymer molecule is linked to another component by cucurbituril host-guest chemistry. This publication does not describe or suggest the formation of a capsule having a shell that is a supramolecular cross-linked network. There is no suggestion that a nested capsule, such as described herein, could or should be formed.

US 2008/0199519 describes multilayer microcapsules, where an outer capsule encapsulates an inner capsule. The inner capsule is a mixture of crosslinked polymer (e.g. alginate) and cells. The polymer is not a supramolecular network and there is no mention of guest-host linkages to hold the capsule material together. Furthermore it does not clear that the inner capsule is a capsule having an internal space. The inner capsule is held within a larger, outer capsule of crosslinked polymer. The outer capsule appears to be completely filled with material (additional polymer and the inner microcapsule). There is no suggestion that the each capsule could or should have a shell that is a supramolecular cross-linked network.

Hoog et al. (*Soft Matter* 2012, 8, 4552) is a review article describing self-assembled architectures with multiple aqueous compartments. The authors discuss the use of multiple emulsion systems (amongst many other systems) for the preparation of liquid multicompartments. There is no suggestion that it would be useful to prepare nested capsules having shells that are supramolecular cross-linked networks.

Nested Capsules

The present invention provides a system of nested capsules. Thus, in a basic arrangement, a first capsule is held with a second capsule. Each of the capsules has a shell that is a supramolecular network. The nested capsule of the invention is suitable for holding and storing encapsulants (a cargo), and delivering those encapsulants to a chosen location for release at a preferred time.

The capsule shell material is stable, allowing for material encapsulated within each of the capsules to be transferred and stored. Moreover, the nested arrangement of capsules allows encapsulated material to be held apart, and therefore prevented from interacting. The capsule shells may be disrupted as required to release encapsulated material.

A nested capsule system is attractive for it provides compartmentalisation within the second capsule. An encapsulant (cargo) held within the first capsule may be prevented from exiting the first capsule and entering the remaining internal space of the second capsule. Similarly, an encapsulant held within the internal space of the second capsule (but not within the first capsule) may be prevented from entering into the first capsule space.

In this way the nested capsule can be viewed as having zones, where each zone has an encapsulant that is prevented from moving into another, neighbouring zone by the shell.

The first capsule is not covalently bonded to the second capsule. It will be appreciated that the second capsule is not provided as a layer on the surface of the first capsule. Thus, the first and second capsules together do not form a multi-layered material.

The first and second capsules may differ only in size. Thus, the second capsule must be capable of holding the first capsule. The capsules may differ in the composition of the shell material. The capsule shells have pores and the pore sizes of the first and second capsules may be the same or different.

In the light of the worked experiments described herein and the cited prior art, it is clear that variations of the basic arrangement are possible. Thus, in a further embodiment of the invention, a plurality of first capsules is held within the second larger capsule. Each of the first capsules may be the same or they may be diffident.

The term different is used to denote any difference between the first capsules. Thus, the first capsules may differ in size, in composition of the shell material, and/or the first capsules may differ in relation to the encapsulant (the cargo) held.

In a further embodiment of the invention, the second capsule is itself held within a third larger capsule. The relationship between the second and third capsules is the same as the relationship between the first and second capsules. Further outer capsules may be provided, such as fourth, fifth, tenth, twentieth or more capsules, with each capsule holding a series of lower order capsules.

The formation of nested capsules is made possible by recent developments in fluidic chemistry. The formation of double and triple emulsions by fluidic techniques (for example) forms the basis for allowing the preparation of nested capsules, as described herein.

In one embodiment, the invention provides a nested capsule wherein a first capsule is held within a second capsule. The shell of the first and second capsules may be the same or different. It is preferred that the shells of the first and second capsules are different, as this allows the shells to be manipulated in an orthogonal manner.

In one embodiment, the invention provides a nested capsule wherein a plurality, such as two, three, four or five, or more, of first capsules held within a second capsule. Here, the shell of each of the first capsules may be the same or different. The shells of each of the first capsules may be the same, allowing all the first capsules to be manipulated in similar manner. It will be appreciated that the shells of individual first capsules from the plurality of first capsules may be different to allow the first shells to be manipulated in an orthogonal manner.

As described below in relation to encapsulants, individual first capsules from the plurality of first capsules may hold the same or different encapsulants. Whilst the first encapsulants may be different, the shell material of each of the first capsules may be the same. This would allow, for example, all the different encapsulants to be released from the first capsules at the same time. It may be the case that the first encapsulants are different, and the shell material of each of the first capsules may be different. This would allow, for example, all the different encapsulants to be released sequentially from the first capsules.

In one embodiment, the invention provides a nested capsule wherein a first capsule is held within a second capsule, and the second capsule is held within a third capsule. The second and first capsules may be such capsules as described above.

As will be apparent from the above, each capsule comprises a shell of material which is a supramolecular network that is formed from the complexation of a host with building blocks covalently linked to appropriate guest molecules i.e. molecules that are capable of forming a non-covalent complex with the host.

Each shell defines an internal space, which may be referred to as a hollow space. The hollow space of the second capsule is suitable for holding one or more first capsules and optionally one or more encapsulants also. The hollow space of the first capsule is suitable for holding one or more encapsulants. Thus, in the present invention a reference to a capsule is not a reference to a particle having no internal space. The internal space of a capsule may be referred to as a domain.

Thus, in one embodiment, the capsules of the invention extend to those capsules encapsulating a component within the shell. The shell may form a barrier limiting or preventing the release of material encapsulated within.

A shell has pores. Typically these pores are sufficiently small to prevent the encapsulant from being released. The network making up a shell may be disrupted (at least partly disassembled) in response to disruption conditions, thereby permitting release of encapsulant from within a shell. Any pores may be enlarged through a disruption of the host-guest complex. Such decomplexation therefore creates pores through which encapsulated components may be released from within the shell. In some embodiments of the invention, the shell material may subsequently be reformed by reassembly of the shell components.

The pores may be of a certain size to permit small components, such as solvent and competitor molecules, to pass into and out of a capsule.

In one embodiment, the capsule holds a solvent, such as water, within a shell. The solvent may be an organic solvent, such as chloroform, or an oil, such as fluorinated oil. The solvent may be a solution or suspension comprising one or more of the reagents that are for use in the preparation of the supramolecular shell i.e. unreacted reagents. Within the shell there may also be present a network that is formed from the complexation of the reagents that have been used to generate the shell. The solvent is typically the fluid that is the main carrier in the fluid flow that is used to prepare the capsule.

A solvent is not an encapsulant within the meaning of the present case.

Where a capsule is said to encapsulate a component, it is understood that that this encapsulated component may be present within the internal space defined by the shell. In one embodiment, the encapsulant is also present, at least partially, within the pores of the shell.

The presence of a component within the shell and/or within the pores of the shell may be determined using suitable analytical techniques which are capable of distinguishing the shell material and the encapsulant. For example, each of the shell material and the component may have a detectable label or suitable functionality that is independently detectable (orthogonal) to the label or functionality of the other. In one embodiment, each of the shell and the component has an orthogonal fluorescent label. For example, one has a rhodamine label and the other has a fluorescein label. Laser scanning confocal microscopy techniques may be used to independently detect the fluorescence of each label, thereby locating each of the shell and encapsulant. Where the component signals are located at the same point as the signals from the shell, it is understood that the component resides within a pore of the shell.

As explained herein, the capsule shells may be labelled. In one embodiment, the first and second capsule shells may be differentially labelled.

The general shape of the shell, and therefore the shape of the capsule, is not particularly limited. In practice however, the shape of the capsule may be dictated by its method of preparation. In the preparation methods described herein, a capsule shell may be prepared using fluidic droplet formation techniques. Typically, the shell material is formed at the boundary of a discrete (or discontinuous) phase in a continuous phase. For example, one phase may be an aqueous phase, and the other may be a water immiscible phase. The discrete region may be a droplet, having a substantially spherical shape. The shell formed is therefore also substantially spherical.

In certain embodiments, a nested capsule may be obtained when the outer shell, such as the shell of the second capsule, has a substantially spherical shape. This capsule may be subjected to a drying step, which reduces the amount of solvent (for example, water) in and around the capsule. As a result of this step, the capsule shrinks in size. At first the shell maintains a substantially spherical shape. After further drying, a capsule sphere may partially or fully collapsed in on itself. The structural integrity of the capsule is maintained and the shell simply distorts to accommodate changes in the internal volume. Thus, the capsules of the invention include those capsules where the shell of the second capsule and/or the first capsule is an at least partially collapsed sphere.

Given the formation of the capsule shell at the boundary of the discrete region (for example, a droplet), references to the dimensions of a droplet may also be taken as references to the dimension of the capsule. The capsule shell may form prior to a drying step.

The inventors have established that nested capsules that have been shrunk, for example by desolvation, may subsequently be returned to their original substantially spherical shape, by, for example, resolvating the capsule.

The shape of a nested capsule may be determined by simple observation of the formed capsule using microscopy, such as bright field microscopy, scanning electron microscopy or transmission electron microscopy. Where the shell material comprises a label, the detection of the label through the shell will reveal the capsule shape. For example, where the label is a fluorescent label, laser scanning confocal microscopy may be used to locate the shell material and its shape.

The size of the nested capsule is not particularly limited, in one embodiment, the nested capsule is a nested microcapsule and/or a nested nanocapsule.

In one embodiment, the outer capsule of the nested capsule, such as the second capsule, has an average size of at least 0.1, 0.2, 0.5, 0.7, 1, 5, 10, 20, 30, 40, 50, 100 or 200 µm in diameter.

In one embodiment, the outer capsule of the nested capsule, such as the second capsule, has an average size of at most 400, 200, 100, 75 or 50 µm in diameter.

In one embodiment, the nested capsule size is in a range where the minimum and maximum diameters are selected from the embodiments above. For example, the nested capsule size is in range from 10 to 100 µm in diameter.

Average size refers to the numerical average of measured diameters for a sample of capsules. Typically, at least 5 capsules in the sample are measured. A cross section measurement is taken from the outmost edges of the shell.

In one embodiment, the outer capsule is the second capsule. In one embodiment, the diameter of the second capsule is at least 1.5, 2, 5, 10 or more times the diameter of the second capsule. Similar relationship applies to a third, fourth, fifth, tenth or twentieth capsule with respect to the capsule of a lower generation.

The cross-section of a capsule within the nested capsule may be determined using simple microscopic analysis of the formed nested capsules. For example, the formed nested capsules may be placed on a microscope slide and the capsules analysed. Alternatively, the capsule size may be measured during the preparation process, for example as the nested capsules are formed in a channel of a fluidic device (i.e. in line).

The measurement of the cross section may also be achieved using techniques related to the detection of a detectable label or functionality present within the shell material. As mentioned above in relation to detection and location of the encapsulated component, the shell material may comprise a fluorescent label which may be detected by laser scanning confocal microscopy techniques. The presence of multiple labels within and around a capsule shell allows the cross-sectional shape to be determined, and the largest cross-section measured.

In the preparation method described herein a nested capsule is prepared using a fluidic droplet generation technique. Each capsule shell is formed at a droplet interface, which is created in a channel of a fluidic droplet generating device, at the boundary of the droplet phase with the continuous phase. The size of a capsule is therefore substantially the same as that of the droplet in which it is formed.

The present inventors have established that each of the capsules in the nested capsule may be prepared with a low size distribution. This is particularly advantageous, as a large number of capsules may be prepared, each with predictable physical and chemical characteristics.

In one embodiment, each capsule diameter has a relative standard deviation (RSD) of at most 0.5%, at most 1%, at most 1.5%, at most 2%, at most 4%, at most 5%, at most 7%, or at most 10%.

The relative standard deviation is calculated from the standard deviation divided by the numerical average and multiplied by 100. The size of the capsule refers to the largest cross section of the capsule, in any section. The cross-section of a substantially spherical capsule is the diameter.

The shell defines an internal cavity which is suitable for encapsulating a component. The size of the internal space will generally correspond to the size of the capsule itself. Thus, the dimension, for example the diameter, of the internal space may be selected from any one of the diameter values given above for the shell itself.

Where the size of the capsule is measured, the diameter refers to the distance from the outermost edge to outmost edge of the shell material of two opposing points, as mentioned above. Where the size of the internal space is measured, the diameter refers to the distance from the innermost edge to innermost edge of the shell material of two opposing points The inventors have established techniques that allow the shell outer and inner edges to be determined. For example, the presence of a detectable label within the shell material allows the outermost and innermost edges of the shell to be determined. If these edges can be detected, the thickness of the shell may be determined.

Typically, the diameter as measured from outermost to outermost edge is not significantly different to the diameter as measure from innermost to innermost edge. The difference is the thickness of the shell at the two opposing points.

In one embodiment, the shell has a thickness of at least 0.02, at least 0.05, at least 0.1, at least 0.5, at least 1.0, at least 2.0 or at least 5.0 µm.

As previously noted, a capsule shell has pores. The pores are typically of a size that is too small to permit passage of encapsulants therethrough. For example, components encapsulated within the capsule may be prevented from passing through the pores of the shell, and therefore cannot be released from the capsule. Such material may be released from the capsule by, for example, disrupting the host-guest complexes that hold the shell together. Disruption of the shell in this way creates larger pores through which material may pass.

It is believed that the pore size may be increased upon solvation of a previously desolvated capsule. As the capsule shrinks, the porosity of the capsule may decrease as the shell material folds over, thereby at least partially blocking some of the pores.

The size of a pore may be gauged experimentally using a range of encapsulated components each having a different cross-section, such as a different diameter. The cross-section may be known or may be predicted based on an understanding of the likely configuration of the component. The pore size may be determined based on which components are released from the capsule and which are not.

The cross-section, typically diameter, of a component may be predicted based on the calculated radius of gyration for each encapsulated component. Such calculations are most suitable for determining the size of small globular particles, and may be used in relation to polymeric systems, such as polypeptides, polynucleotides and polysaccharides. Methods for the calculation of radius of gyration are described in Andrieux et al. Analytical Chemistry 2002, 74, 5217, which is incorporated by reference herein.

A nested capsule comprising an encapsulated component may be prepared using the methods described herein. Once the capsule (with encapsulant) is prepared, the capsule and its aqueous surroundings may be analysed for loss of material from within the shell out to the external phase (which may be the internal phase of a larger capsule, e.g. the second capsule, or the external environment of the nested capsule). The encapsulated compounds may have an analytical label to aid detection. Suitable labels include fluorescent labels which are detectable using standard fluorescence microscopy techniques.

In one embodiment, dextran compounds of differing molecular weight may be used as test compounds to determine the pore size of a formed capsule. The dextran may be labelled, and preferably with a fluorescent label.

Dextran compounds of differing molecular weight are readily available from commercial sources, including, for example. Sigma Aldrich. Dextrans having an average molecular weight of from 1,000 to 500,000 are available. Dextran with a molecular weight of 70 kDa has a radius of gyration of approx. 8 nm, whilst dextran with a molecular weight of 150 kDa has a radius of gyration of approx. 11 nm (see Granath Journal of Colloid Science 1958, 13, 308). Dextran compounds having a fluorescent label, such as fluorescein isothiocyanate, are also available from commercial sources, including, again, Sigma Aldrich.

In one embodiment, the pore size is at most 20, at most 15, at most 10, at most 5, at most 1 or at most 0.5 μm.

In one embodiment, the pore size is at most 500, at most 200, at most 100, at most 50, or at most 20 nm.

In one embodiment, the pore size is at least 0.5, at least 1, or at least 5 nm.

In one embodiment, the pore size is in a range where the minimum and maximum pore sizes are selected from the embodiments above. For example, the pore size is in range 1 to 20 nm.

As an alternative to dextran, protein standards may be used instead. As an alternative to the labelled compounds described above, it also possible to detect the compound released from the capsule using mass spectroscopy, or protein gel electrophoresis (for protein standards).

Surface area, porosity and pore size may also be determined experimentally using BET gas absorption techniques.

As expected, the shell pore size is influenced by the amount of cucurbituril present in the complexable composition from which the capsule may be prepared. Increasing the amount of cucurbituril present in the complexable composition is believed to increase the amount of crosslinking with the network, thereby reducing the size of the pores in the formed shell material.

As expected, the shell pore size is influenced by the amount of host, such as cucurbituril, present in the complexable composition from which the capsule may be prepared. Increasing the amount of host present in the complexable composition is believed to increase the amount of crosslinking with the network, thereby reducing the size of the pores in the formed shell material.

As discussed above, a shell material may include detectable labels or detectable functionalities. As noted previously, the shells of the first and second capsules may be labelled and they may be differentially labelled.

A detectable functionality is functionality of a capsule shell component having a characteristic that is detectable over and above the characteristics that are present in other components of the capsule, or even other functionalities of the same component. The detectable functionality may refer to a particular chemical group that gives rise to a unique signal in, for example, IR, UV-VIS, NMR or Raman analysis. The functionality may be a radioactive element.

Typically a part of the shell material or the encapsulant is provided with a detectable label, as the introduction of a chosen label allows the use of techniques that are most appropriate for the property that is to be measured. Described herein are building blocks having fluorescent detectable labels. Also described herein are building blocks that are capable of providing a surface enhanced resonance effect.

A shell may have additional functionality on its inner and/or outer surfaces. Described herein are building blocks having functionality to improve solubility, to aid detection, reactive functionality for later elaboration of the shell, and catalysts, amongst others. Such functionality may be provided on the first and/or second capsule of the nested capsules.

In one embodiment, the outer shell of the nested capsule, such as the second capsule, is provided with functionality on its outer surface for connection of the nested capsule to a surface.

The capsule shells are stable and may be stored without loss of the shell structure. The integrity of the shell therefore allows the capsule to be used as a storage vessel for an encapsulant. The capsules of the invention are thermally stable and the shell is known to maintain its integrity at least up to 50° C., and higher for certain complexes. The capsules of the invention are also stable at reduced pressures (i.e. below ambient pressure). A capsule shell is known to maintain its integrity down to at least 20 Pa.

The capsules of the invention have a long shelf life. The present inventors have confirmed that structural integrity is maintained for at least 10 months.

The structural integrity of the shell is in part due to the strength of the cucurbituril guest-host complex, which is described in more detail below.

The description of the nested capsules of the invention makes reference to a second capsule holding a first capsule. As explained above, in further embodiment, the nested capsule may be provided with a third capsule that holds one or more second capsules, and similarly fourth and further capsules may be provided, with each capsule holding one or more capsules of a lower generation. References to the relationship between the second capsule and the first capsule may be applied to the relationship between the third capsule and the second capsule, and the fourth capsule and the third capsule as so on, as appropriate.

It will be appreciated that the nested capsules of the invention may have a multiple series of capsules within capsules. The description of the invention makes reference to a basic nested capsule with a first capsule provided in a second capsule. The nested capsules of the invention extend to nested capsules having, for example, 3, 4, 5, 10, 20 or more generations of capsules within capsules.

It is noted above that the first and second capsules may differ in certain respects. The building blocks present in the shells of the first and second capsules may differ. Where the first and second shells each contain a polymeric molecule building block, the polymer may differ.

In one embodiment, a shell of one of the first and second capsules contains groups that are positively charged, and the other shell of one of the first and second capsules contains groups that are negatively charged. Thus, a shell may be regarded as having positive or negative charge as appropriate. The charge of the shell may be provided by groups present on the building blocks making up the shell and/or the guest molecules (and not the host). In one embodiment, the charge of the shell is provided by a polymeric molecule building block. Thus, the polymeric molecule may include positively charged groups or negatively charged groups. The worked examples in the present case demonstrate the use polymeric molecules having positively and negatively charges groups in the formation of a capsule shell. For example, the polymer RC-PVA-Rhod-MV carries positive charges on the methyl viologen and rhodamine groups. The polymer PHEAm-FITC-Azo carrier carries negative charges on the fluorescin moiety.

Complex

Each capsule shell comprises a network that is held together by a supramolecular handcuff. The complex that forms this supramolecular handcuff is based on a host, such as cucurbituril, hosting one guest (binary complex) or two guests (ternary complex). The host forms a non-covalent bond to each guest. The present inventors have established that host-guest complexes are readily formed under mild conditions and provide robust non-covalent linkages between building blocks. The formation of the non-covalent complex is tolerant of many functionalities within the building blocks. One of the present inventors has demonstrated that polymer networks may be prepared using a cucurbituril handcuff. However, until now, the formation of precise polymer structures, such as nested capsules, using hosts such as cucurbituril has not been described.

In one embodiment, a shell of a capsule is a network having a plurality of complexes, wherein each complex comprises a host hosting a first guest molecule and a second guest molecule. The first and second guest molecules are covalently linked to a first building block, or to a first building block and a second building block.

Where the complex comprises two guests within the cucurbituril cavity, the association constant, $K_a$, for that complex is at least $10^3$ $M^{-2}$, at least $10^4$ $M^{-2}$, at least $10^5$ $M^{-2}$, at least $10^6$ $M^{-2}$, at least $10^7$ $M^{-2}$, at least $10^8$ $M^{-2}$, at least $10^9$ $M^{-2}$, at least $10^{10}$ $M^{-2}$, at least $10^{11}$ $M^{-2}$, or at least $10^{12}$ $M^{-2}$.

Where a host non-covalently holds hosts two guest molecules, the guest molecules may be the same or they may be different. A host that is capable of hosting two guest molecules may also be capable of forming a stable binary complex with a single guest. The formation of a ternary guest-host complex is believed to proceed via an intermediate binary complex. Within the shell, there may be present a binary complex formed between a guest molecule and a host. The binary complex may be regarded as a partially formed ternary complex that has not yet formed a non-covalent bond to another guest molecule.

In one embodiment, a shell is a network having a plurality of complexes, wherein each complex comprises a host hosting one guest molecule, and each host is covalently linked to at least one other host. The guest molecules are covalently linked to a first building block, or to a first building block and a second building block.

Where the complex comprises one guest within the cucurbituril cavity, the association constant, $K_a$, for that complex is at least $10^3$ $M^{-1}$, of at least $10^4$ $M^{-1}$, of at least $10^5$ $M^{-1}$, of at least $10^6$ $M^{-1}$, of at least $10^7$ $M^{-1}$, of at least $10^8$ $M^{-1}$, of at least $10^9$ $M^{-1}$, of at least $10^{10}$ $M^{-1}$, of at least $10^{11}$ $M^{-1}$, or of at least $10^{12}$ $M^{-1}$.

In one embodiment, the guest is a compound capable of forming a complex which has an association constant in the range $10^4$ to $10^7$ $M^{-1}$.

The formation of the complex is reversible. The decomplexation of the complex to separate the guest or guests may occur in response to an external stimulus, including, for example, a competitor guest compound. Such decomplexation may be induced in order to provide additional or larger pores in the capsule through which an encapsulated material may pass.

As noted above in relation to the capsule shell, the complex of the host with one or two guests is the non-covalent link that links and/or interlinks the building blocks to from a supramolecular network of material. The complex is generally stable long term at ambient temperatures and does not separate at reduced pressure, as explained for the shell.

A shell may include a mixture of binary and ternary complexes as described above. The first and second capsules may make use of different complexes, or they may make use of the same complexes.

Network

The formation of a supramolecular complex serves to link and/or interlink building blocks, thereby forming a network of material. This is the capsule shell.

Two types of network may be used in a shell. The first type is based on the formation of a plurality of ternary complexes, each complex comprising a host with a first guest molecule and a second guest molecule. The second type is based on the formation of a plurality of binary complexes, each complex comprising a host with a first guest molecule. In this second type, each host is covalently linked to a least one other host. These types of network may be combined with a shell.

Where a building block is provided with a plurality of guest molecules, all of the guest molecules need not participate in a complex with a host. Where the network is based on linking between ternary structures, a guest molecule of a building block may be in a binary complex with a host. The binary complex may be regarded as a partially formed ternary complex that has not yet combined with a further guest molecule to generate the ternary form.

Throughout the description references are made to a building block, a first building block and a second building block. It is understood that a reference to such is a reference to a collection of the individual molecules, particles, polymers etc. that are the building blocks. Where a reference is intended to an individual building block molecule, particle etc. the term single is used in reference to the building blocks e.g. a single first building block.

The networks described below are the basic networks that are obtainable from the compositions described. It is understood that the present inventions extends to more complex networks that are obtainable from compositions comprising further building blocks.

Network of Ternary Complexes

This network is obtainable from the assembly of a first guest molecule and a second guest molecule together with a host. The guest molecules may be provided on one or two (or more) building blocks as described below.

In one embodiment, a network is obtainable or obtained from the complexation of a composition comprising a host, a first building block covalently linked to a plurality of first guest molecules and a second building block covalently linked to a plurality of second guest molecules, wherein a first guest molecule and a second guest molecule together with the host are suitable for forming a ternary guest-host complex.

The ternary complex serves to non-covalently link the first and second building blocks. A single first building block may form a plurality of non-covalent links to a plurality of second building blocks. Similarly, a single second building block may form a plurality of non-covalent links to a plurality of first building blocks. In this way, a network of material is established.

It is noted that in some embodiments, the first and second guest molecules may be identical. Therefore the first and second building blocks may differ in their compositions. In some embodiments, the first and second building blocks may be identical. In this case, the first and second guest molecules are different.

FIGS. 25-30 a schematic structure of a basic network formed between a host, a single first building block and two single second building blocks. In FIGS. 25-30, the guest molecules are depicted as rectangles which are covalently linked (vertical line) to a building block (horizontal line). The vertical line may depict a direct covalent bond or a linker to the building block. The building block may be a polymeric molecule, a particle or the like, as described herein.

As shown in FIG. 25, some of the first guest molecules (unshaded rectangles) of the first building block are in complex with the hosts (barrels) and second guest molecules (shaded rectangles) of the second building blocks.

It is apparent that not all guest molecules present participate in a complex in the final network. Each of the first and second building blocks may form complexes with other second and first building blocks respectively. The guest molecules are shaded for ease of understanding. However, as explained herein, the guest molecules of the first and second building blocks may be the same.

In an alternative embodiment, a network is obtainable or obtained from the complexation of a composition comprising a host and a first building block covalently linked to a plurality of first guest molecules and a plurality of second guest molecules, wherein a first and a second guest molecule together with the host are suitable for forming a ternary guest-host complex.

The ternary complex serves to non-covalently link and/or interlink the first building block. A single first building block may form a plurality of non-covalent links to a plurality of other first building blocks. Additionally, or alternatively, a single first building block may form a plurality of non-covalent interlinks with itself, thereby to crosslink the single first building block.

As before, the first and second guest molecules may be identical.

FIG. 26 depicts a schematic structure of a basic network formed between a host and two single first building blocks each having a plurality of first and second guest molecules. Some of the first guest molecules (unshaded rectangles) of the first building block are in complex with the hosts (barrels) and second guest molecules (shaded rectangles) of another first building block. It can be seen from the network illustrated that a first building block may form intramolecular complexes, thereby crosslinking a single first building block.

It is apparent that not all guest molecules present need participate in a complex in the final network. Each of the first building blocks may form complexes with other first building blocks, or with other parts of the same building block. As explained herein, the first and second guest molecules may be the same.

Optionally, the composition further comprises a second building block covalently linked to one or more third guest molecules, one or more fourth guest molecules or both, wherein a third and a fourth molecule together with the host are suitable for forming a ternary guest-host complex, or the first and fourth guest molecules together with the host are suitable for forming a ternary guest-host complex, or the second and third guest molecules together with the host are suitable for forming a ternary guest-host complex.

Where the second building block is provided with a plurality of third and fourth guest molecules, the ternary complex serves to non-covalently link and/or interlink the second building block. A single second building block may form a plurality of non-covalent links to a plurality of other second building blocks. Additionally, or alternatively, a single second building block may form one or more non-covalent interlinks with itself, thereby to crosslink the single second building block.

The third and fourth guest molecules may be suitable for forming complexes with the first and second guest molecules of the first building block. In one embodiment, the first and third guest molecules are the same. In one embodiment the second and fourth guest molecules are the same. Here, the ternary complex serves to non-covalently link the first and second building blocks, for example through a complex of the first and fourth guest molecules and/or through a complex of the second and third guest molecules.

Thus, a single first building block may form a plurality of non-covalent links to a plurality of second building blocks. Similarly, a single second building block may form a plurality of non-covalent links to a plurality of first building blocks. In this way, a network of material is established. The building blocks may also form intermolecular non-covalent bonds as described previously.

Where a second building block is covalently linked to one or more third guest molecules or one or more fourth guest molecule, the first and fourth molecules together with the host are suitable for forming a ternary guest-host complex, and the second and third molecules together with the host are suitable for forming a ternary guest-host complex. Thus, the ternary complex serves to non-covalently link the second building block to the first building block.

FIG. 27 depicts a schematic structure of a basic network formed between the host, three single first building blocks each having a plurality of first and second guest molecules, and two second building blocks each having a plurality of third and fourth guest molecules. Some of the first guest molecules (unshaded rectangles) of the first building block are in complex with the hosts (barrels) and second guest molecules (shaded rectangles) of another first building block. Some of the third guest molecules (partially shaded rectangles) of the second building block are in complex with the hosts (barrels) and fourth guest molecules (dashed rectangles) of another second building block. A first guest molecule of the first building block is in complex with a host and a fourth guest molecule (dashed rectangles) of a second building block. A second guest molecule of the first building block is in complex with a host and a third guest molecule of a second building block.

The first and third guest molecules may be the same. The second and fourth guest molecules may be the same.

A second building block may be covalently linked to one guest molecule (which may be a third or a fourth guest molecule). In this embodiment, the second building block is not capable of forming a plurality of links to other building blocks. As such, the building block would not contribute to the formation of a cross links within the network. However, the second building block may be provided in order to introduce into the network a particular physical or chemical characteristic that is possessed by the second building block. For example, the second building block may comprise a detectable label or a functional group, such as a solubilising group. The incorporation of the second building block into the network therefore allows the modification of the physical or chemical characteristics of the overall network.

FIG. 28 depicts a schematic structure of a basic network formed between cucurbituril, two single first building blocks each having a plurality of first and second guest molecules, and also including a single second building block, which is covalently linked to one fourth guest molecule, and a detectable label. Some of the first guest molecules (unshaded rectangles) of the first building block are in complex with cucurbituril hosts (barrels) and second guest molecules (shaded rectangles) of another first building block. A first guest molecule of the first building block is in complex with a cucurbituril host and a fourth guest molecule. The detectable label (partially shaded circle) may be provided in order to allow identification of the resulting network.

Network of Binary Complexes Based on a Plurality of Covalently Linked Hosts

This network is obtainable from the assembly of a first guest molecule together with a host, which host is covalently linked to one or more other hosts. The guest molecules may be provided on one, or two (or more) building blocks as described herein.

The covalently linked hosts serve to link building block molecules through the plurality of complexes that are formed within each of the covalently linked hosts.

FIG. 29 depicts a schematic structure of a basic network formed between a plurality of covalently linked hosts and two single first building blocks each having a plurality of first guest molecules. Some of the first guest molecules (unshaded rectangles) of each of the single first building block are in a binary complex with cucurbituril hosts (barrel). The hosts are linked, thereby to form a link between each of the first building blocks.

It is apparent that not all guest molecules present need participate in a complex in the final network. Each of the single first building blocks may form complexes with other first building blocks respectively, or may form an intramolecular crosslink with another portion of the same building block. As explained herein, the guest molecules of the first and second building blocks may be the same. In FIG. 29, one of the first building blocks may be replaced with a second building block which is covalently linked to a second guest molecule.

The second guest molecule is one that is capable of forming a binary complex with the host. The second guest molecule may be the same as the first guest molecule.

In FIG. 29, two hosts are shown linked together. The present invention encompasses the use of systems where more than two hosts are linked together. For example multiple hosts may be pendant to a polymeric molecule.

Network of Ternary Complexes Based on a Plurality of Covalently Linked Hosts

It will be apparent from the description of the networks above, that each of the hosts in the plurality of covalently linked hosts may be suitable for forming ternary complexes. Thus, the plurality of covalently linked hosts may be used in place of the host described for use in the network of ternary complexes.

FIG. 30 depicts a structural schematic of a basic network formed between a plurality of covalently linked hosts, two single first building blocks each having a plurality of first guest molecules, and two single second building blocks each having a plurality of second guest molecules. Some of the first guest molecules (unshaded rectangles) of the first building block are in tertiary complex with a host (barrel) and the second guest molecules (shaded rectangles) of the second building block The hosts are linked, thereby to form a link between each of the first and second building blocks.

As before, the first and second guest molecules may be the same. Each of the first and second building blocks may form complexes with other second and first building blocks respectively. Other permutations are possible, for example, where the plurality of covalently linked hosts has greater than two hosts.

Other Networks

Described above are the basic networks of the invention that are obtained or obtainable from the compositions described. It will be clear to one of skill in the art that the compositions described may include further building blocks, for example third and fourth building blocks, each linked to one or more guest molecules. The present invention also covers capsules where the shell comprises a mixture of any one of the networks described above. Such are obtainable from compositions comprising an appropriate selection of host, covalently linked hosts, first building block and second building block as appropriate.

The invention also relates to a capsule having a shell that is a network comprising different hosts. Different hosts may be chosen in order to obtain a network that is based on ternary and binary complexes. Different hosts may be chosen in order to generate networks that result from the selective complexation of each host for different guest molecules, which may be present on the same or different building blocks.

Complexation

In one embodiment, a shell is obtainable from the complexation of (a) a composition comprising a host and (1) or (2); or (b) a composition comprising a plurality of covalently linked hosts and (1), (2) or (3).

In one embodiment, the shell is obtainable from the complexation of a composition comprising a host and (1) or (2).

In one embodiment, the shell is obtainable from the complexation of a composition comprising a host and (1).

In one embodiment, the shell of each capsule in the nested capsule is obtainable from the complexation of a composition comprising a host and (1) or (2).

In one embodiment, the shell of one of the first or second capsule in the nested capsule is obtainable from the complexation of a composition comprising a host and (1), and the shell of the other of the first or second capsule in the nested capsule is obtainable from the complexation of a composition comprising a host and (2).

(1) comprises a first building block covalently linked to a plurality of first guest molecules and a second building block covalently linked to a plurality of second guest molecules, wherein a first guest molecule and a second guest molecule together with the host are suitable for forming a ternary guest-host complex.

(2) comprises a first building block covalently linked to a plurality of first guest molecules and a plurality of second guest molecules, wherein a first and a second guest molecule together with the host are suitable for forming a ternary guest-host complex. Optionally the composition further comprises a second building block covalently linked to one or more third guest molecules, one or more fourth guest molecules or both, wherein a third and a fourth molecule together with the host are suitable for forming a ternary guest-host complex, and/or the first and fourth molecules together with the host are suitable for forming a ternary guest-host complex, and/or the second and third molecules together with the host are suitable for forming a ternary guest-host complex;

(3) comprises a first building block covalently linked to a plurality of first guest molecules, wherein the first guest molecule together with the host are suitable for forming a binary guest-host complex. Optionally the composition further comprises a second building block covalently linked to one or more second guest molecules, wherein the second guest molecule together with the host are suitable for forming a binary guest-host complex.

In one embodiment, the capsule is a microcapsule.

In one embodiment, the capsule encapsulates a component.

Suitable hosts, such as cucurbituril as described below.

It will be appreciated that the first and second guests may be the same, where such guests are capable of forming a ternary host complex.

Host

Described herein are capsules having a shell that is obtainable from the supramolecular complexation of a host with building blocks covalently linked to appropriate guest molecules.

In one embodiment the host is cucurbituril.

Other guest-host complexes may be used, in the alternative to the cucurbituril guest-host complex or in addition to the cucurbituril guest-host complex. For example, in one the host is selected from cyclodextrin, calix[n]arene, crown ether and cucurbituril, and the one or more building blocks have suitable host guest functionality for the cyclodextrin, calix[n]arene, crown ether or cucurbituril host respectively.

In one embodiment, the host is selected from cyclodextrin, calix[n]arene, and crown ether, and the one or more building blocks have suitable host guest functionality for the cyclodextrin, calix[n]arene, or crown ether respectively.

The present invention therefore encompasses the use of a guest that is capable of non-covalently hosting one or two guests, thereby to crosslink the building blocks to which the guests are covalently bound.

The use of cucurbituril is preferred owing to the high binding constants that available and the ease through which complexes, and capsules, may be assembled.

In one embodiment, the networks of the first and second capsules make use of the same host in the non-covalent complexes.

In one embodiment, the networks of the first and second capsules make use of different hosts in the non-covalent complexes.

Cucurbituril

The present invention provides use of cucurbituril as a supramolecular handcuff to link and/or crosslink building blocks. The cucurbituril may be used to form ternary complexes with first and second guest molecules present on one or more building blocks. The formation of such complexes links individual building blocks thereby to form a network of material. This network is the shell of the capsule.

Additionally, or alternatively, a plurality of covalently linked cucurbiturils is provided and each cucurbituril may be used to form binary complexes with a guest molecule present on one or more building blocks. The formation of a binary complex with each of the covalently linked cucurbiturils thereby forms a network of material. This network is the shell of the capsule.

In one embodiment, the cucurbituril is capable of forming a ternary complex. For example, CB[8], is capable of forming a ternary complex.

In one embodiment, the cucurbituril is capable of forming a binary complex. For example, CB[7], is capable of forming a binary complex.

In one embodiment, the cucurbituril is capable of forming ternary and binary complexes.

For example, CB[8], is capable of forming a ternary or a binary complex, depending upon the nature of the guest.

In one embodiment, the cucurbituril is a CB[5], CB[6], CB[7], CB[8], CB[9], CB[10], CB[11] or CB[12] compound.

In one embodiment, the cucurbituril is a CB[6], CB[7], or CB[8] compound.

In one embodiment, the cucurbituril is a CB[8] compound.

In one embodiment, references to a cucurbituril compound are references to variants and derivatives thereof.

Cucurbituril compounds differ in their water solubility. The methods of capsule preparation may be adapted to take into account this solubility, as described later. Therefore the choice of cucurbituril compound is not limited by its aqueous solubility.

In one embodiment, the cucurbituril compound has a solubility of at least 0.01 mg/mL, at least 0.02 mg/mL, at least 0.05 mg/mL, or at least 0.10 mg/mL.

In one embodiment, the solubility refers to aqueous solubility (i.e. an aqueous phase).

In one embodiment, the solubility refers to solubility in a water immiscible phase, such as an oil phase or an organic phase.

Cucurbit[8]uril (CB[8]; CAS 259886-51-6) is a barrel shaped container molecule which has eight repeat glycoluril units and an internal cavity size of 479 Å$^3$ (see structure below). CB[8] is readily synthesised using standard techniques and is available commercially (e.g. Sigma-Aldrich, MO USA).

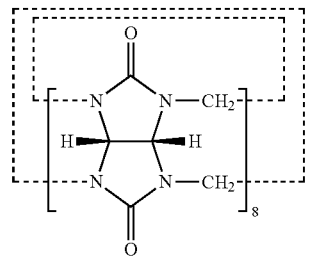

In other aspects of the invention, CB[8] variants are provided and find use in the methods described herein.

A variant of CB[8] may include a structure having one or more repeat units that are structurally analogous to glycoluril. The repeat unit may include an ethylurea unit. Where all the units are ethylurea units, the variant is a hemicucurbituril. The variant may be a hemicucurbit[12]uril (shown below, see also Lagona et al. *Angew. Chem. Int. Ed.* 2005, 44, 4844).

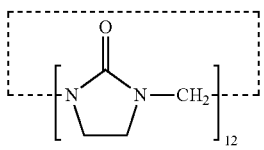

In other aspects of the invention, cucurbituril derivatives are provided and find use in the methods described herein. A derivative of a cucurbituril is a structure having one, two, three, four or more substituted glycoluril units. A substituted cucurbituril compound may be represented by the structure below:

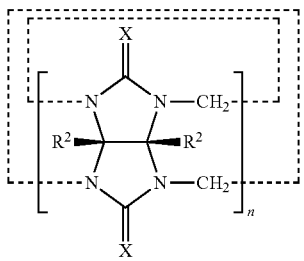

wherein:
n is an integer of at least 5;
and for each glycoluril unit
each X is O, S or NR$^3$, and
—R$^1$ and —R$^2$ are each independently selected from —H and the following optionally substituted groups: —R$^3$, —OH, —OR$^3$, —COOH, —COOR$^3$, —NH$_2$, —NHR$^3$ and —N(R$^3$)$_2$ where —R$^3$ is independently selected from C$_{1-20}$alkyl, C$_{6-20}$carboaryl, and C$_{5-20}$heteroaryl, or where —R$^1$ and/or —R$^2$ is —N(R$^3$)$_2$, both —R$^3$ together form a C$_{5-7}$ heterocyclic ring; or together —R$^1$ and —R$^2$ are C$_{4-6}$alkylene forming a C$_{6-8}$carbocyclic ring together with the uracil frame.

In one embodiment, one of the glycoluril units is a substituted glycoluril unit. Thus, —R$^1$ and —R$^2$ are each independently —H for n−1 of the glycoluril units In one embodiment, n is 5, 6, 7, 8, 9, 10, 11 or 12.
In one embodiment, n is 5, 6, 7, 8, 10 or 12.
In one embodiment, n is 8.
In one embodiment, each X is O.
In one embodiment, each X is S.
In one embodiment, R$^1$ and R$^2$ are each independently H.
In one embodiment, for each unit one of R$^1$ and R$^2$ is H and the other is independently selected from —H and the following optionally substituted groups: —R$^3$, —OH, —OR$^3$, —COOH, —COOR$^3$, —NH$_2$, —NHR$^3$ and —N(R$^3$)$_2$. In one embodiment, for one unit one of R$^1$ and R$^2$ is H and the other is independently selected from —H and the following optionally substituted groups: —R$^3$, —OH, —OR$^3$, —COOH, —COOR$^3$, —NH$_2$, —NHR$^3$ and —N(R$^3$)$_2$. In this embodiment, the remaining glycoluril units are such that R$^1$ and R$^2$ are each independently H.

Preferably —R$^3$ is C$_{1-20}$alkyl, most preferably C$_{1-6}$alkyl. The C$_{1-20}$alkyl group may be linear and/or saturated. Each group —R$^3$ may be independently unsubstituted or substituted. Preferred substituents are selected from: —R$^4$, —OH, —OR$^4$, —SH, —SR$^4$, —COOH, —COOR$^4$, —NH$_2$, —NHR$^4$ and —N(R$^4$)$_2$, wherein —R$^4$ is selected from C$_{1-20}$alkyl, C$_{6-20}$carboaryl, and C$_{5-20}$heteroaryl. The substituents may be independently selected from —COOH and —COOR$^4$.

In some embodiments, —R$^4$ is not the same as —R$^3$. In some embodiments, —R$^4$ is preferably unsubstituted.

Where —R$^1$ and/or —R$^2$ is —OR$^3$, —NHR$^3$ or —N(R$^3$)$_2$, then —R$^3$ is preferably C$_{1-6}$alkyl. In some embodiments, —R$^3$ is substituted with a substituent —OR$^4$, —NHR$^4$ or —N(R$^4$)$_2$. Each —R$^4$ is C$_{1-6}$alkyl and is itself preferably substituted.

In some embodiments of the invention there is provided the use of a plurality of covalently linked cucurbiturils. Such covalently linked cucurbiturils are suitable for forming networks based on the complexation of the cucurbituril with guest molecules of a building block. The complexes formed may be ternary or binary complexes.

A cucurbituril may be covalently linked to another cucurbituril via a linker group that is a substituent at position R$^1$ or R$^2$ at one of the glycoluril units in the cucurbituril as represented in the structure shown above. There are no particular limitations on the covalent link between the cucurbiturils. The linker may be in the form of a simple alkylene group, a polyoxyalkylene group or a polymer, such as a polymeric molecule described herein for use in the building block. Where the linker is a polymeric molecule, the cucurbiturils may be pendant to that polymer.

Cucurbituril Guests

As noted above, a cucurbituril guest is a compound that is capable of forming a guest-host complex with a cucurbituril. The term complexation therefore refers to the establishment of the guest-host complex.

In some embodiments of the invention, the guest host complex is a ternary complex comprising the cucurbituril host and a first guest molecule and a second molecule. Typically such complexes are based around CB[8] and variants and derivatives thereof.

In some embodiments of the invention, the guest host complex is a binary complex comprising the cucurbituril host and a first guest molecule. Typically such complexes are based around CB[5] or CB[7], and variants and derivatives thereof. In the present invention, binary complexes are obtainable from a plurality of covalently linked cucurbiturils. CB[8], and variants and derivatives thereof, may also form binary complexes.

In principal, any compound having a suitable binding affinity may be used in the methods of the present invention. The compound used may be selected based on the size of the moieties that are thought to interact with the cavity of the cucurbituril. The size of these moieties may be sufficiently large to permit complexation only with larger cucurbituril forms.

Cucurbituril guest molecules are well known in the art. Examples of guest compounds for use include those described in WO 2009/071899, Jiao et al. (Jiao et al. *Org. Lett.* 2011, 13, 3044), Jiao et al. (Jiao et al. *J. Am. Chem. Soc.* 2010, 132, 15734) and Rauwald et al. (Rauwald et al *J. Phys. Chem.* 2010, 114, 8606).

Described below are guest molecules that are suitable for use in the formation of a capsule shell. Such guest molecules may be connected to a building block using standard synthetic techniques.

A cucurbituril guest molecule may be derived from, or contain, a structure from the table below:

| Guest Molecules |
|---|
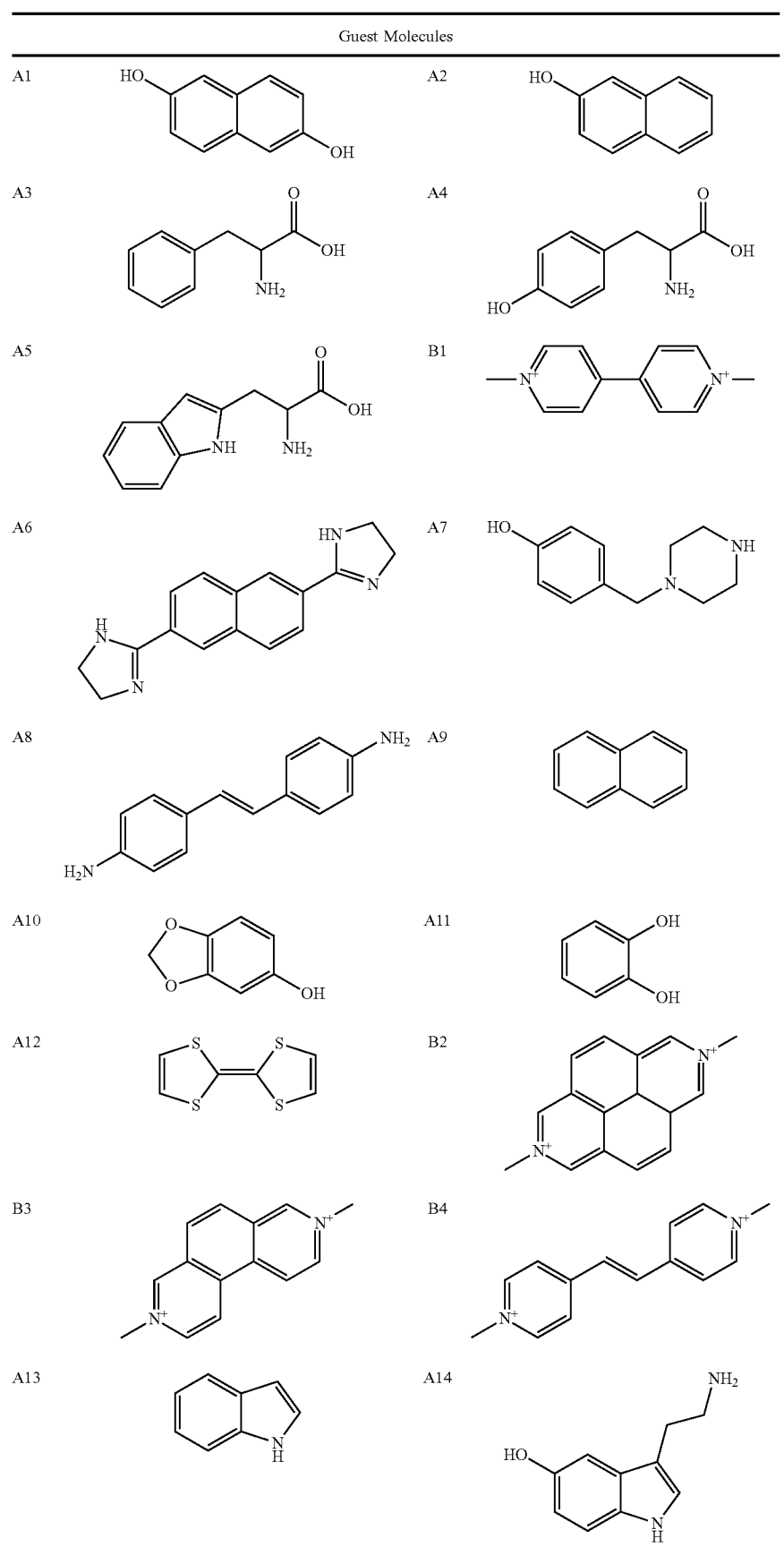

-continued
| | Guest Molecules | | |
|---|---|---|---|
| A15 | 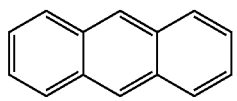 [SMILES: c1ccc2cc3ccccc3cc2c1] | A16 | 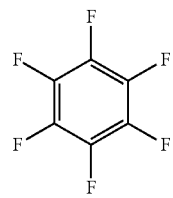 [SMILES: Fc1c(F)c(F)c(F)c(F)c1F] |
| A17 | 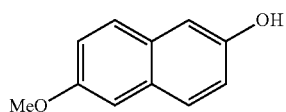 [SMILES: COc1ccc2cc(O)ccc2c1] | A18 | 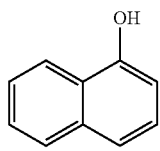 [SMILES: Oc1cccc2ccccc12] |
| A19 | 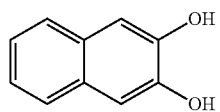 [SMILES: Oc1cc2ccccc2cc1O] | A20 | 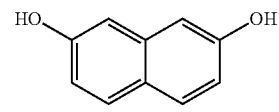 |
| A21 | 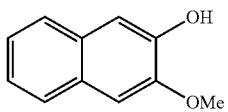 | A22 | 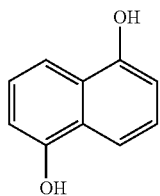 [SMILES: Oc1cccc2c(O)cccc12] |
| A23 | 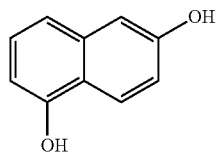 [SMILES: Oc1ccc2c(O)cccc2c1] | A24 | 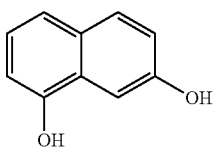 [SMILES: Oc1ccc2cccc(O)c2c1] |
| A25 | 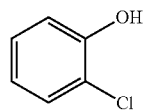 | A26 | 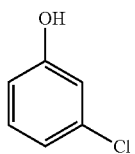 |
| A27 | 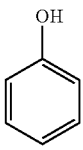 | A28 | 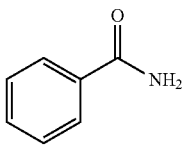 |
| A29 | 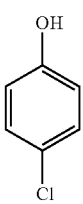 | A30 | 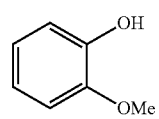 |
| A31 | 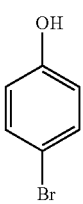 | A32 | 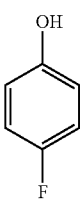 |

| | Guest Molecules | | |
|---|---|---|---|
| A33 | 4-iodophenol | A34 | 3-methoxyphenol |
| A35 | 3-cyanophenol | A36 | resorcinol (1,3-dihydroxybenzene) |
| A37 | 2-cyanophenol | A38 | 4-methoxyphenol |
| A39 | 1,4-dimethoxybenzene | A40 | hydroquinone (1,4-dihydroxybenzene) |
| A41 | phloroglucinol (1,3,5-trihydroxybenzene) | A42 | 4-cyanophenol |
| A43 | 1H-benzotriazole | A44 | azobenzene |
| A45 | 2-naphthalenethiol | A46 | 1-adamantanamine | where the structure may be a salt, including protonated forms, where appropriate. In one embodiment, the guest molecules are guest molecules for CB[8].

In one embodiment, the guest molecule is, or is derived from, or contains, structure A1-A43, A46 or B1-B4, in the table above.

In one embodiment, the guest molecule is, or is derived from, or contains, structure A1, A2, or A13 in the table above.

In one embodiment, the guest molecule is, or is derived from, or contains, structure B1.

Additionally, the guest molecule is or is derived from, or contains, adamantane, ferrocene or cyclooctane (including bicyclo[2.2.2]octane). Such are described by Moghaddam et al. (see *J. Am. Chem. Soc.* 2011, 133, 3570).

In some embodiments, first and second guest molecules form a pair which may interact within the cavity of cucurbituril to form a stable ternary host-guest complex. Any guest pair that fits within the cavity of the cucurbituril may be employed. In some embodiments, the pair of guest molecules may form a charge transfer pair comprising an electron-rich and an electron-deficient compound. One of the first and second guest molecules acts as an electron acceptor and the other as an electron donor in the CT pair. For example, the first guest molecule may be an electron deficient molecule which acts an electron acceptor and the second guest molecule may be an electron rich molecule which acts as an electron donor or vice versa. In one embodiment, the cucurbituril is CB[8].

Suitable electron acceptors include 4,4'-bipyridinium derivatives, for example N,N'-dimethyldipyridyliumylethylene, and other related acceptors, such as those based on diazapyrenes and diazaphenanthrenes. Viologen compounds including alkyl viologens are particularly suitable for use in the present invention. Examples of alkyl viologen compounds include N,N'-dimethyl-4,4'-bipyridinium salts (also known as Paraquat).

Suitable electron donors include electron-rich aromatic molecules, for example 1,2-dihydroxybenzene, 1,3-dihydroxybenzene, 1,4-dihydroxybenzene, tetrathiafulvalene, naphthalenes such as 2,6-dihydroxynaphthalene and 2-naphthol, indoles and sesamol (3,4-methylenedioxyphenol). Polycyclic aromatic compounds in general may find use as suitable electron donors in the present invention. Examples of such compounds include anthracene and naphthacene.

Amino acids, such as tryptophan, tyrosine and phenylalanine may be suitable for use as electron donors. Peptide sequences comprising these amino acids at their terminus may be used. For example, a donor comprising an amino acid sequence N-WGG-C, N-GGW-C or N-GWG-C may be used.

In some embodiments, the guest molecules are a pair of compounds, for example first and second guest molecules, where one of the pair is an A compound as set out in the table above (e.g. A1, A2, A3 etc.), and the other of the pair is a B compound as set out in the table above (e.g. B1, B2, B3 etc.). In one embodiment, the A compound is selected from A1-A43 and A46. In one embodiment, the B compound is B1.

Other suitable guest molecules include peptides such as WGG (Bush, M. E. et al *J. Am. Chem. Soc.* 2005, 127, 14511-14517).

An electron-rich guest molecule may be paired up with any electron-deficient CB[8] guest molecule. Examples of suitable pairs of guest molecules for example first and second guest molecules, for use as described herein may include:
 viologen and naphthol;
 viologen and dihydroxybenzene;
 viologen and tetrathiafulvalene;
 viologen and indole;
 methylviologen and naphthol;
 methylviologen and dihydroxybenzene;
 methylviologen and tetrathiafulvalene;
 methylviologen and indole;
 N,N'-dimethyldipyridyliumylethylene and naphthol;
 N,N'-dimethyldipyridyliumylethylene and dihydroxybenzene;
 N,N'-dimethyldipyridyliumylethylene and tetrathiafulvalene;
 N,N'-dimethyldipyridyliumylethylene and indole;
 2,7-dimethyldiazapyrenium and naphthol;
 2,7-dimethyldiazapyrenium and dihydroxybenzene;
 2,7-dimethyldiazapyrenium and tetrathiafulvalene; and
 2,7-dimethyldiazapyrenium and indole.

In particular, suitable pairs of guest molecules for use as described herein may include 2-naphthol and methyl viologen, 2,6-dihydroxynaphthalene and methyl viologen and tetrathiafulvalene and methyl viologen.

In one embodiment, the guest pair is 2-naphthol and methyl viologen.

In one embodiment, the guest pair is a reference to a pair of guest molecules suitable for forming a ternary complex with CB[8].

In one embodiment, the guest molecule is preferably an ionic liquid. Typically, such guests are suitable for forming a complex with CB[7]. However, they may also form complexes with CB[8] in either a binary complex, or in a ternary complex together with another small guest molecule or solvent (see Jiao et al. *Org. Lett.* 2011, 13, 3044).

The ionic liquid typically comprises a cationic organic nitrogen heterocycle, which may be an aromatic nitrogen heterocycle (a heteroaryl) or a non aromatic nitrogen heterocycle. The ionic liquid also typically comprises a counter-anion to the cationic organic nitrogen heterocycle. The nitrogen heteroaryl group is preferably a nitrogen $C_{5-10}$heteroaryl group, most preferably a nitrogen $C_{5-6}$heteroaryl group, where the subscript refers to the total number of atoms in the ring or rings, including carbon and nitrogen atoms. The non-aromatic nitrogen heterocycle is preferably a nitrogen $C_{5-6}$heterocycle, where the subscript refers to the total number of atoms in the ring or rings, including carbon and nitrogen atoms. A nitrogen atom in the ring of the nitrogen heterocycle is quaternised.

The counter-anion may be a halide, preferably a bromide. Other counter-anions suitable for use are those that result in a complex that is soluble in water.

The guest is preferably a compound, including a salt, comprising one of the following groups selected from the list consisting of: imidazolium moiety; pyridinium moiety; quinolinium moiety; pyrimidinium moiety; pyrrolium moiety; and quaternary pyrrolidine moiety.

Preferably, the guest comprises an imidazolium moiety. An especially preferred guest is 1-alkyl-3-alkylimidazolium, where the alkyl groups are optionally substituted.

1-Alkyl-3-alkylimidazolium compounds, where the alkyl groups are unsubstituted, are especially suitable for forming a complex with CB[7].

1-Alkyl-3-alkylimidazolium compounds, where the alkyl groups are unsubstituted, are especially suitable for forming a complex with CB[6]

1-Alkyl-3-alkylimidazolium compounds, where an alkyl group is substituted with aryl (preferably napthyl), are especially suitable for forming a complex with CB[8].

The 1-alkyl and 3-alkyl substituents may the same or different. Preferably, they are different.

In one embodiment, the 3-alkyl substituent methyl, and is preferably unsubstituted.

In one embodiment, the 1-alkyl substituent ethyl or butyl, and each is preferably unsubstituted.

In one embodiment, the optional substituent is aryl, preferably $C_{5-10}$aryl. Aryl includes carboaryl and heteroaryl. Aryl groups include phenyl, napthyl and quinolinyl.

In one embodiment, the alkyl groups described herein are linear alkyl groups.

Each alkyl group is independently a $C_{1-6}$alkyl group, preferably a $C_{1-4}$alkyl group.

The aryl substituent may itself be another 1-alkyl-3-substituted-imidazolium moiety (where the alkyl group is attached to the 3-position of the ring).

In another embodiment, the compound preferably comprises a pyridinium moiety.

The ionic liquid molecules describe above are particular useful for forming binary guest-host complexes. Complexes comprising two ionic liquid molecules as guests within a cucurbituril host are also encompassed by the present invention.

A cucurbituril may be capable of forming both binary and ternary complexes. For example, it has been previously noted that CB[6] compounds form ternary complexes with short chain 1-alkyl-3-methylimidazolium guest molecules, whilst longer chain 1-alkyl-3-methylimidazolium guest molecules form binary complexes with the cucurbituril host.

Preferred guests for use in the present invention are of the form $H^+X^-$, where $H^+$ is one of the following cations,

| Cation | Structure |
|---|---|
| A | 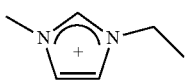 |
| B | 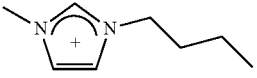 |
| C | 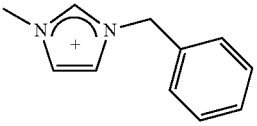 |
| D | 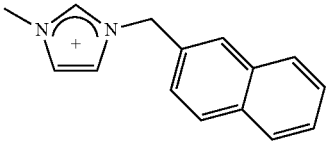 |
| E | 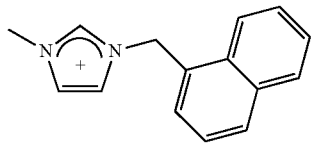 |
| F | 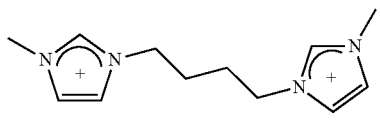 |
| G | 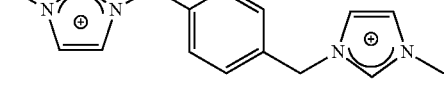 |
| H | 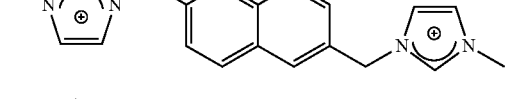 |
| I | 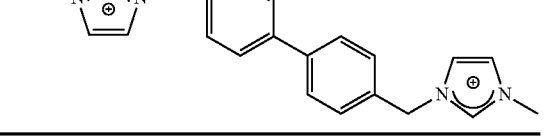 | and $X^-$ is a suitable counter-anion, as defined above. A preferred counter anion is a halide anion, preferably $Br^-$.

In a preferred embodiment, cation A or cation B may be used to form a complex with CB[7] or CB[6].

In a preferred embodiment, cation D or cation E may be used to form a complex with CB[8].

Cations A and B may be referred to as 1-ethyl-3-methylimidazolium and 1-butyl-3-methylimidazolium respectively.

Cations D and E may be referred to as 1-naphthalenylmethyl-3-methylimidazolium, where D is 1-naphthalen-2-ylmethyl-3-methylimidazolium and E is 1-naphthalen-1-ylmethyl-3-methylimidazolium.

Alternatively or additionally, the guest compounds may be an imidazolium salt of formula (I);

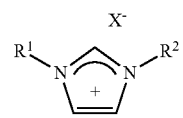

wherein $X^-$ is a counter anion;
$R^1$ is independently selected from H and saturated $C_{1-6}$ alkyl;
$R^2$ is independently $C_{1-10}$ alkyl which may optionally contain one or more double or triple bonds, and may be optionally interrupted by a heteroatom selected from —O—, —S—, —NH—, and —B—, and may be optionally substituted.

In one embodiment, $X^-$ is independently selected from the group consisting of $Cl^-$, $Br^-$, $I^-$, $BF_4^-$, $PF_6^-$, $OH^-$, $SH^-$, $HSO_4^-$, $HCO_3^-$, $NTf_2$, $C_2N_5O_4$, $AlCl_4^-$, $Fe_3Cl_{12}$, $NO_3^-$, $NMeS_2^-$, $MeSO_3^-$, $SbF_6^-$, $PrCB_{11}H_{11}^-$, $AuCl_4^-$, $HF_2^-$, $NO_2^-$, $Ag(CN)_2^-$, and $NiCl_4^-$. In one embodiment, $X^-$ is selected from $Cl^-$, $Br^-$, and $I^-$.

In one embodiment, $R^1$ is selected from H and linear saturated $C_{1-6}$ alkyl.

In one embodiment, $R^2$ is linear $C_{1-10}$ alkyl, which may optionally contain one or more double bonds, and may be optionally interrupted by a heteroatom selected from —O—, —S—, —NH—, and —B—, and may be optionally substituted.

In one embodiment, $R^2$ is linear $C_{1-10}$ alkyl, which may optionally contain one or more double bonds, and may be optionally substituted.

In one embodiment, where a double or triple bond is present, it may be conjugated to the imidazolium moiety. Alternatively, the double or triple bond may not be conjugated to the imidazolium moiety.

In one embodiment, the optional substituents are independently selected from the group consisting of halo, optionally substituted $C_{5-20}$ aryl, —$OR^3$, —$OCOR^3$, =O, —$SR^3$, =S, —$BR^3$, —$NR^3R^4$, —$NR^3COR^3$, —$N(R^3)CONR^3R^4$, —$COOR^3$, —$C(O)R^3$, —$C(=O)SR^3$, —$CONR^3R^4$, —$C(S)R^3$, —$C(=S)SR^3$, and —$C(=S)NR^3R^4$, where each of $R^3$ and $R^4$ is independently selected from H and optionally substituted saturated $C_{1-6}$ alkyl, $C_{5-20}$ aryl and $C_{1-6}$ alkylene-$C_{5-20}$ aryl.

or $R^3$ and $R^4$ may together may form an optionally saturated 5-, 6- or 7-membered heterocyclic ring which is optionally substituted with a group —$R^3$.

In one embodiment, the optional substituents are independently selected from the group consisting of halo, optionally substituted $C_{5-20}$ aryl, —$OR^3$, —$OCOR^3$, —$NR^3R^4$, —$NR^3COR^3$, —$N(R^3)CONR^3R^4$, —$COOR^3$, —$C(O)R^3$, and —$CONR^3R^4$, where $R^3$ and $R^4$ are defined as above.

Each $C_{5-20}$ aryl group may be independently selected from a $C_{6-20}$ carboaryl group or a $C_{5-20}$ heteroaryl group.

Examples of $C_{6-20}$ carboaryl groups include phenyl and napthyl.

Examples of $C_{5-20}$ heteroaryl groups include pyrrole (azole) ($C_5$), pyridine (azine) ($C_6$), furan (oxole) ($C_5$), thiophene (thiole) ($C_5$), oxazole ($C_5$), thiazole ($C_5$), imidazole (1,3-diazole) ($C_5$), pyrazole (1,2-diazole) ($C_5$), pyridazine (1,2-diazine) ($C_6$), and pyrimidine (1,3-diazine) ($C_6$) (e.g., cytosine, thymine, uracil).

Each $C_{5-20}$ aryl is preferably selected from optionally substituted phenyl, napthyl and imidazolium.

Each $C_{5-20}$ aryl group is optionally substituted. The optional substituents are independently selected from halo, $C_{1-6}$ alkyl, —$OR^3$, —$OCOR^3$, —$NR^3R^4$, —$NR^3COR^3$, —$N(R^3)CONR^3R^4$, —$COOR^3$, —$C(O)R^3$, and —$CONR^3R^4$, where $R^3$ and $R^4$ are defined as above.

In one embodiment, each $C_{5-20}$ aryl group is optionally substituted with $C_{1-6}$ alkyl.

Where the $C_{5-20}$ aryl group is an imidazolium, such is preferably substituted at nitrogen with a group $R^1$ (thereby forming a quaternary nitrogen).

The compound of formula (I) comprises an imidazolium moiety having a substituent $R^2$ at the 1-position and a substituent $R^1$ at the 3-position. In a further aspect of the invention, the compound of formula (I) may be optionally further substituted at the 2-, 4- or 5-position with a group $R^4$, wherein $R^4$ has the same meaning as $R^1$.

The embodiments above are combinable in any combination, as appropriate.

Other Hosts and Guests

In some embodiments, a host is selected from cyclodextrin, calix[n]arene, and crown ether, and the one or more building blocks have suitable host guest functionality for the cyclodextrin, calix[n]arene, or crown ether respectively.

In one embodiment, the host is cyclodextrin and the one or more building blocks have suitable cyclodextrin guest functionality.

The host may form a binary complex with a guest. In such cases, the host will be covalently linked to one or more other guest molecules to allow the formation of crosslinks between building blocks.

In one embodiment, a host is cyclodextrin. Cyclodextrin compounds are readily available from commercial sources. Many guest compounds for use with cyclodextrin are also known. Cyclodextrin is a non-symmetric barrel shaped cyclic oligomers of D-glucopyranose. Typically, the cyclodextrin is capable of hosting hydrophobic uncharged guests. For example, guests include those molecules having hydrocarbon and aromatic functionalities such as adamantane, azobenzene, and stilbene derivatives. Other guest molecules for cyclodextrin include biomolecules such as xylose, tryptophan, estrial, esterone and estradiol.

In one embodiment, the cyclodextrin is an α-, β- or γ-cyclodextrin. In one embodiment, the cyclodextrin is a β- or γ-cyclodextrin. Typically larger guests are used together with a γ-cyclodextrin.

The cyclodextrin has a toroid geometry, with the secondary hydroxyl groups of the D-glucopyranose located at the larger opening, and the primary hydroxyl groups at the smaller opening. One or more of the hydroxy groups, which may the secondary or the primary hydroxy groups, may be functionalised. Typically, the primary hydroxyl groups are functionalised. In one embodiment, references to a cyclodextrin compound are references to derivatives thereof. For example, one or two primary hydroxyl groups of the cyclodextrin is functionalised with a alkylamine-containing sub-sistent. In another example one, two or three of the hydroxyl groups within each D-glucopyranose unit is replaced with an alkyl ether group, for example a methoxy group. A plurality of covalently linked cyclodextrins may be connected via the hydroxyl groups.

Examples of unfunctionalised and functionalised cyclodextrins are set out in Chart 1 of Rekharsky et al. (*Chem. Rev.* 1998, 98, 1875), and examples of compounds for use as guests are set out over Tables 1 to 3 and Chart 2. Rekharsky et al. is incorporated by reference herein.

In the methods of preparation, the cyclodextrin may be present in the second phase, for example in an aqueous phase, as described herein.

In one embodiment, the host is calix[n]arene. Calix[n]arenes compounds are readily available from commercial sources, or may be prepared by condensation of phenol, resorcinol and pyrogallol aldehydes, for example formaldehyde.

Many guest compounds for use with calix[n]arenes are known. Typically, the calix[n]arene is capable of hosting amino-containing molecules. Piperidine-based compounds and amino-functionalised cyclohexyl compounds may find use as guests. Further examples of guests include atropine, crytand, phenol blue, and anthrol blue amongst others.

Examples of unfunctionalised and functionalised cyclodextrins are set out in Chart 1 of Danil de Namor et al. (*Chem. Rev.* 1998, 98, 2495-2525), which is incorporated by reference herein. Examples of compounds for use as guests are set out over Tables 2, 3, 5 and 10 of Danil de Namor et al.

In one embodiment, the calix[n]arene is a calix[4]arene, calix[5]arene or calix[6]arene. In one embodiment, the calix[n]arene is a calix[4]arene.

Suitably functionalised calix[n]arenes may be prepared through use of appropriately functionalised hydroxy aryl aldehydes. For example, the hydroxyl group may be replaced with an alkyl ether-containing group or an ethylene glycol-containing group. A plurality of covalently linked calix[n]arenes may be connected via the hydroxyl groups.

In the methods of preparation, the calix[n]arene may be present in the second phase, for example in an aqueous phase or a water immiscible phase, as described herein.

In one embodiment, the host is a crown ether. Crown ether compounds are readily available from commercial sources or may be readily prepared.

Many guest compounds for use with crown ether are also known. For example, cationic guests such as amino- and pyridinium-functionalized molecules may be suitable guest molecules.

Examples of unfunctionalised and functionalised cyclodextrins are set out throughout Gokel et al. (*Chem. Rev.* 2004, 104, 2723-2750), which is incorporated by reference herein. Examples of compounds for use as guests are described throughout the text.

In one embodiment, the crown ether is selected from the groups consisting of 18-crown-6, dibenzo-18-crown-6, diaza-18-crown-6 and 21-crown-7. In the present invention, larger crown ethers are preferred. Smaller crown ethers may have be capable of binding small metal ions only. Larger crown ethers are capable of binding functional groups and molecules.

In some embodiments, the host is a guest having crown ether and calix[n]arene functionality. Such hosts are referred to as calix[n]crowns.

In the methods of preparation, the crown ether may be present in the second phase, for example in a water immiscible phase, as described herein.

Other guest-host relationships may be used as will be apparent to a person of skill in the art. Other guest-host complexes for use in the present invention include those highlighted by Dsouza et al. (*Chem. Rev.* 2011, 111, 7941-7980) which is incorporated by reference herein, and in particular those hosts set out in Schemes 6 and 7, which includes cucurbituril, cyldoextrin, and calixerane as well as cyclophane AVCyc, calixpyridine C4P and squarimide SQAM.

The use of cyclodextrin is preferred over crown ether and calix[n]arene hosts.

Building Blocks

The host is used as a supramolecular handcuff to join together one or more building blocks. The formation of a complex of the host with suitable guest components that are linked to the building blocks forms a network of material. This material provides a capsule shell. The complex non-covalently crosslinks the building block or non-covalently links the building block to another building block.

It is understood from the above that a building bock is an entity that serves to provide structure to the formed network. The building block also serves as the link between a plurality of guest molecules, and it may therefore also be referred to as a linker. In some embodiments, a building block is provided for the purpose of introducing a desirable physical or chemical characteristic into the formed network. As mentioned above in relation to the network, a building block may include a functionality to aid detection and characterisation of the shell. Such building blocks need not necessarily participate in a crosslink.

A building block, such as a first building block, may be covalently linked to a plurality of host guest molecules, such as cucurbituril guest molecules. A building block will therefore non-covalently link to a plurality of hosts, which hosts will non-covalently link to other building blocks, thereby to generate a network of material.

A building block, such as a first building block or a second building block, may be covalently linked to a plurality of guest molecules. In one embodiment, a building block is covalently linked to at least 3, at least 4, at least 5, at least 10, at least 20, at least 50, at least 100, at least 500, at least 1,000, at least 2,000, at least 5,000 or at least 10,000 guest molecules.

In certain embodiments, building blocks covalently linked to one or more cucurbituril guest molecules may be used. However, such building blocks are used only in combination with other building blocks that are covalently linked to at least two guest molecules.

In one embodiment, there is provided a first building block covalently linked to a plurality of first guest molecules and a second building block covalently linked to a plurality of second guest molecules. Each of the first and second building blocks may be covalently linked to at least the number of guest molecules described above.

In one embodiment, there is provided a first building block covalently linked to a plurality of first guest molecules and covalently linked to a plurality of second guest molecules.

The first building block may be covalently linked to at least the number of guest molecules described above, which numbers may refer independently to the number of first guest molecules and the number of second guest molecules.

In one embodiment, there is provided a second building block covalently linked to one or more third guest molecules and/or covalently linked to a one or more fourth guest molecules. In one embodiment, the second building block is covalently linked to at least the number of guest molecules described above, which numbers may refer independently to the number of third guest molecules and the number of fourth guest molecules. Such a second building block may be used together with the first building block described in the paragraph above.

Throughout the description, references are made to first and second building blocks. In some embodiments, the first and second building blocks may be distinguished from each other owing to differences, at least, in the structure of the building blocks themselves. In some embodiments, the structures of the first and second building blocks are the same. In this case, the building blocks may be distinguished from each other owing to differences, at least, in the guest molecules that are covalently linked to each of the first and the second guest molecules. Thus the terms first and second are intended to convey a difference between the first building block together with its guest molecules and the second building block together with its guest molecules.

The nested capsule of the invention has a first capsule held in a second capsule. Each capsule has a shell of material that is a supramolecular cross-linked network having a non-covalent complex of a host, such as cucurbituril, and one or more building blocks comprising suitable guest functionality. As described herein, the network for each capsule may be include first or second building blocks, and optionally further building blocks, with each building block provided with suitable guest functionality.

A building block present in the shell of the first capsule may be present in the shell of the second capsule.

A building block present in the shell of the first capsule may not be present in the shell of the second capsule.

The shell of the first capsule may have one or two building blocks.

The shell of the second capsule may have one or two building blocks.

The building blocks are not particularly limited, and the building block includes compounds and particles, and may encompass assemblies of either of these. The guest molecules are covalently linked to some portion of the building block.

At its simplest a building block is a linker for the connection of guest molecules.

In one embodiment the building block is a polymeric molecule or a particle.

Advantageously, a building block may be provided with certain functionality to aid the formation of the capsule shell, or to improve its physical or chemical properties.

In one embodiment, the building block is provided with functionality to alter, or preferably improve, water solubility. The functionality may take the form of a solubilising group, such as a group comprising polyethylene glycol functionality. Other examples include groups comprising amino, hydroxy, thiol, and carboxy functionality.

In one embodiment, the building block is provided with functionality to aid detection or analysis of the building block, and to aid detection or analysis of the formed shell. Advantageously, such functionality may also aid the detection of material encapsulated within the shell. The functionality may take the form of a detectable label, such as a fluorescent label.

In one embodiment, a building block is anionic or cationic.

In one embodiment, one of the first and second capsules has a building block that is anionic, and the other of first and second capsules has a building block that is cationic.

In one embodiment, one of the first and second capsules has two anionic building blocks.

In one embodiment, one of the first and second capsules has two cationic building blocks.

In preferred methods of synthesis, it is useful for a building block to be positively or negatively charged. Charge attractions may be usefully used in the preparation methods to ensure the distribution of the building block to a desired interphase boundary (droplet edge).

The guest molecules may have functional groups that are positively or negatively charged.

A reference to an anionic or cationic building block may also include a reference to a building block that is linked to guest molecules having functional groups that are positively or negatively charged, as appropriate.

Additionally or alternatively, the building block itself may have groups that are positively or negatively charged. Where the building block is a polymeric molecule, the positively or negatively charged groups may be present within the side chains of the monomer units. The backbone of the polymeric molecule itself may also carry positively or negatively charged groups.

The present case includes as an example the polymer RC-PVA-Rhod-MV carries positive charges on methyl viologen groups (the guest molecule) and rhodamine groups. The polymer PHEAm-FITC-Azo carries negative charges on the fluorescein group. Here, the Azo guest molecule is not charged. RC-PHEAm-AmAm-FITC-Azo also carries negative charges on the fluorescein group.

In one embodiment, the building block is provided with reactive functionality for use in the later elaboration of the shell material. The reactive functionality may be protected for the shell forming reactions, then later deprotected to reveal the functionality. The functionality may be a group comprising amino, hydroxy, thiol, and carboxy functionality.

Where the building block is provided with reactive functionality is provided, this functionality may be suitable for linking the building block (and therefore the formed capsule) to a surface. In one embodiment, the building block is provided with a catalyst for later use in the catalysis of a reaction at or near the shell surface. The catalyst may be provided at the inner or outer edges of the shell thereby to catalyse internal and/or external reactions.

In one embodiment, the building block is chosen for its ability to influence the opticoelectronic properties of the encapsulant. Additionally or alternatively, the building block may be chosen for its ability to be influenced by the encapsulant. The building block may be suitable for transferring signals from the encapsulant to outside environment.

In one embodiment a building block is capable of providing a surface enhanced resonance effect.

Where functionality is provided it may be located at the outer side of, the inner side of and/or within the shell. Thus, the functionality may be provided in connection with the improvements related to the environment outwith the shell, within the internal space (the space for holding an encapsulant) of the shell and/or within the shell (within the network of shell material).

For the purposes of the methods described herein, the building block, together with the guest molecules to which it is covalently linked, should be soluble, for example in a fluid phase.

In one embodiment, the building block has a solubility of at least 0.01 mg/mL, at least 0.02 mg/mL, at least 0.05 mg/mL, or at least 0.10 mg/mL.

In one embodiment, the solubility refers to aqueous solubility (i.e. an aqueous phase).

In one embodiment, the solubility refers to solubility in a water immiscible phase, such as an oil phase or an organic phase.

A building block is linked to a cucurbituril guest molecule or guest molecules by covalent bonds. The covalent bond may be a carbon-carbon bond, a carbon-nitrogen bond, a carbon-oxygen bond. The bond may be part of a linking group such as an ester or an amide, and/or part of a group comprising an alkylene or an alkoxylene functionality.

Each guest molecule may be linked to the building block using routine chemical linkage techniques. For example, guest molecules may be linked to the building block by: alkylation of a building block bearing an appropriate leaving group; esterification reactions; amidation reactions; ether forming reactions; olefin cross metathesis; or small guest molecule initiated reactions in which a polymer chain is grown off an initiating guest molecule.

In one embodiment, the average molecular weight of a building block, optionally together with any guest molecules, is at least 1,000, at least 5,000, at least 10,000, or at least 20,000. In one embodiment, the average molecular weight of a building block, optionally together with any guest molecules, is at most 30,000, at most 50,000, at most 100,000, at most 200,000, at most 500,000, at most 1,000,000, or at most 2,000,000.

The average molecular weight may refer to the number average molecular weight or weight average molecular weight.

In one embodiment, the average molecular weight of a building block is in a range where the minimum and maximum amounts are selected from the embodiments above. For example, the average molecular weight is in the range 1,000 to 100,000.

In one embodiment, a building block is capable of providing a surface enhanced resonance effect. Typically, such capability is provided by a particle, and most particularly a metal-containing particle. Suitable particles are such as those described herein. Most suitable are those particles that are capable of providing a surface enhanced effect for surface enhanced Raman spectroscopy.

Described below are building blocks that are based on polymeric molecules and particles, including nanoparticles.

In one embodiment, where the network is obtainable from a composition comprising first and second building blocks, the first building block is a polymeric molecule and the second building block is a particle or a polymeric molecule. In one embodiment, where the network is obtainable from a composition comprising first and second building blocks, the first building block is a polymeric molecule and the second building block is a particle.

In one embodiment, where the network is obtainable from a composition comprising a first building block, the first building block is a polymeric molecule.

In one embodiment, each of the first and second capsules has a building block that is a polymeric molecule.

In one embodiment, the first capsule has one or two building blocks, where each building block is a polymeric molecule.

In one embodiment, the second capsule has one or two building blocks, where each building block is a polymeric molecule.

Polymeric Molecule

In one embodiment, a building block is a polymeric molecule.

Polymeric compounds that are covalently linked to cucurbituril guest molecules are known from WO 2009/071899, which is incorporated by reference herein.

Polymeric molecules comprise a plurality of repeating structural units (monomers) which are connected by covalent bonds. Polymeric molecules may comprise a single type of monomer (homopolymers), or more than one type of monomer (co-polymers). Polymeric molecules may be straight or branched. Where the polymeric molecule is a co-polymer, it may be a random, alternating, periodic, statistical, or, block polymer, or a mixture thereof. The co-polymer may also be a graft polymer.

A building block may have has 2, 3, 4 or 5 repeat units. For convenience, such a building block may be referred to as an oligomer.

The polymeric molecule has at least 8, at least 15, at least 100, or at least 1,000 monomer units. The number of units may be an average number of units.

In other embodiment, the polymeric molecule has an average number of monomer units in a range selected from 10-200, 50-200, 50-150 or 75-125.

The number of guest molecules per polymeric molecule building block is as set out above. Alternatively, the number of guest molecules may be expressed as the percentage of monomers present in the polymer that are attached to guest molecules as a total of all the monomers present in the polymeric molecule. This may be referred to as the functionality percentage.

In one embodiment, the functionality of a polymeric molecule is at least 1%, at least 2% or at least 5%.

In one embodiment, the functionality of a polymeric molecule is at most 50%, at most 40%, at most 20%, at most 15 or at most 10%.

In one embodiment, the functionality is in a range where the minimum and maximum amounts are selected from the embodiments above. For example, the functionality is in the range 5 to 40%.

The functionality percentage may be determined from proton NMR measurements of a polymer sample.

In one embodiment, the polymeric molecule has a molecular weight (Mw) of greater than 500, greater than 1000, greater than 2000, greater than 3000 or greater than 4000. The molecular weight may be the weight average molecular weight or the number average molecule weight. The number average and weight average molecular weights of a polymer may be determined by conventional techniques.

In one embodiment, the polymer is a synthetic polydisperse polymer. A polydisperse polymer comprises polymeric molecules having a range of molecular masses. The polydispersity index (PDI) (weight average molecular weight divided by the number average molecular weight) of a polydisperse polymer is greater than 1, and may be in the range 5 to 20. The polydispersity of a polymeric molecule may be determined by conventional techniques such as gel permeation or size exclusion chromatography.

Suitable for use in the present invention are polymeric molecules having a relatively low polydispersity. Such polymeric molecules may have a polydispersity in the range selected from 1 to 5, 1 to 3, or 1 to 2. Such polymers may be referred to as low- or monodisperse in view of their relatively low dispersity.

The use of low- or monodisperse polymeric molecules is particularly attractive, as the reactively of individual molecules is relatively uniform, and the products that result from their use may also be physically and chemically relatively uniform, and may be relatively low- or monodisperse. Methods for the preparation of low- or monodisperse polymers are well known in the art, and include polymerisation reactions based on radical initiated polymerisation, including RAFT (reversible addition-fragmentation chain transfer) polymerisation (see, for example, Chiefari et al. *Macromolecules* 1998, 31, 5559). An example synthesis of a polymer having a low dispersity is also provided herein.

Many polymeric molecules are known in the art and may be used to produce shell material as described herein. The choice of polymeric molecule will depend on the particular application of the capsule. Suitable polymeric molecules include natural polymers, such as proteins, oligopeptides, nucleic acids, glycosaminoglycans or polysaccharides (including cellulose and related forms such as guar, chitosan chitosan, agarose, and alginate and their functionalised derivatives), or synthetic polymers, such as polyethylene glycol (PEG), cis-1,4-polyisoprene (PI), poly(meth)acrylate, polystyrene, polyacrylamide, and polyvinyl alcohol. The polymer may be a homo or copolymer.

The polymeric molecule may comprise two or more natural and/or synthetic polymers. These polymers may be arranged in a linear architecture, cyclic architecture, comb or graft architecture, (hyper)branched architecture or star architecture.

Suitable polymeric molecules include those polymeric molecules having hydrophilic characteristics. Thus, a part of the polymer, which part may refer to, amongst others, a monomer unit, the backbone itself, a side chain or a grafted polymer, is hydrophilic. In one embodiment, the polymeric molecule is capable of forming hydrogen bonds in a polar solvent, such as water. The polymeric molecule is soluble in water to form a continuous phase.

In one embodiment, the polymeric molecule is amphiphilic.

Where two or more building blocks are provided, such as a first and a second building block, each building block may be independently selected from the polymeric molecules described above. In one embodiment, the first and second building blocks are different. In one embodiment, the first and second building blocks are the same. In this latter case, the building blocks themselves differ only with respect to the guest molecules that are covalently attached to each.

In one embodiment, the polymeric molecule is or comprises a poly(meth)aryclate-, a polystyrene- and/or a poly(meth)acrylamide polymer.

In one embodiment, the polymer is or comprises a poly(meth)aryclate polymer, which may be or comprise a polyacrylate polymer The acrylate functionality of the (meth)aryclate may be the site for connecting desirable functionality, for example, for connecting a solubilising group or a detectable label.

In one embodiment, the polymeric molecule is obtained or obtainable from a polymerisable composition comprising:
  (i) monomer, such as a (meth)aryclate or a styrene, which is attached to a cucurbituril guest molecule;
  and optionally further comprising:
  (ii) a monomer, such as a (meth)aryclate or a styrene, which is attached to a detectable label; and/or
  (iii) a monomer, such as a (meth)aryclate or a styrene, which is attached to a solubilising group, such as an aqueous solubilising group.

In one embodiment, each monomer is a (meth)aryclate monomer.

In one embodiment, each monomer is a styrene monomer.

Where (i) is present with other components, such as (ii) or it is present in the polymerisable composition in at least 1, at least 5, at least 10 or at least 20 mole %.

Where (i) is present with other components, such as (ii) or (iii), it is present in the polymerisable composition in at most 90, at most 50, at most 40 or at least 30 mole %.

In one embodiment, the amount of (i) present is in a range where the minimum and maximum amounts are selected from the embodiments above. For example, the amount present in the range 10 to 50 mole %.

In one embodiment, (i) is present at a level sufficient to provide a polymeric molecule having a plurality of cucurbituril guest molecules linked to each single polymer molecule.

In one embodiment, (i) is present at a level sufficient to provide a polymeric molecule having a single cucurbituril guest molecules linked to each single polymer molecule.

In one embodiment, (i) is present at a level sufficient to provide a polymeric molecule having the functionality % described above.

Where (ii) is present, it is present in the polymerisable composition in at least 0.5, at least 1, or at least 2 mole %.

Where (ii) is present, it is present in the polymerisable composition in at most 20, at most 10, or at most 5 mole %.

In one embodiment, the amount of (ii) present is in a range where the minimum and maximum amounts are selected from the embodiments above. For example, the amount present in the range 1 to 5 mole %.

Where (iii) is present, it is present in the polymerisable composition in at least 0.5, at least 1, at least 2, at least 5, at least 10, at least 20, or at least 50 mole %.

Where (iii) is present, it is present in the polymerisable composition in at most 90, at most 80, or at most 70 mole %.

In one embodiment, the amount of (iii) present is in a range where the minimum and maximum amounts are selected from the embodiments above. For example, the amount present in the range 10 to 80 mole %.

Where a reference is made to mole %, this is a reference to the amount of a component present with respect to the total amount, in moles, of (i), and (ii) and (iii), where present, and any other polymerisable monomers, where present. The component referred to may be one of (i), (ii), (iii), or any other polymerisable monomers.

In one embodiment, the composition further comprises one or more additional (meth)acrylate monomers. One monomer may be a (meth)acrylate monomer. One or more monomers may be a (meth)acrylate monomer which is substituted at the ester group.

Where a reference is made to mole %, this is a reference to the amount of a component present with respect to the total amount, in moles, of (i), and (ii) and (iii), where present, and any other polymerisable monomers, where present. The component referred to may be one of (i), (ii), (iii), or any other polymerisable monomers. The component referred to may be a chain transfer agent or a radical initiator, as described below.

The term attached refers to the connection of the acrylate (ester), group or the phenyl group of the styrene, either directly or indirectly to the group specified. Where there is an indirect connected it is understood that a linker group may form the connection between the acrylate and the group specified. In one embodiment, the linker may comprise a (poly)ethylene glycol (PEG) group.

In one embodiment, the detectable label is a fluorescent label. The fluorescent label may be a fluorescein or rhodamine label. The "colour" of the label is not particularly restricted, and green, red, yellow, cyan and orange labels are suitable for use.

In one embodiment, the aqueous solubilising group is a PEG group. The PEG group may have at least 2, 3, 4, 5 or 10 repeat ethylene glycol units. The PEG group may have at most 50, 40, 20, or 15 repeat ethylene glycol units.

In one embodiment, the aqueous solubilising group is or comprises amino, hydroxy, carboxy, or sulfonic acid.

In one embodiment, the amino group is a quaternary amino group, for example a trimethylamino group.

In one embodiment, the composition further comprises a chain transfer agent.

In one embodiment, the chain transfer agent is a thiocarbonylthio compound.

Where a chain transfer agent is present, it is present in the polymerisable composition in at least 0.1, at least 0.5, or at least 1 mole %.

Where a chain transfer agent is present, it is present in the polymerisable composition in at most 10, at most 5, or at most 2 mole %.

In one embodiment, the amount of a chain transfer agent present is in a range where the minimum and maximum amounts are selected from the embodiments above. For example, the amount present in the range 0.5 to 2 mole %.

In one embodiment, the composition further comprises a radical initiator.

Where a radical initiator is present, it is present in the polymerisable composition in at least 0.01, at least 0.05, at least 0.1 mole %.

Where a radical initiator is present, it is present in the polymerisable composition in at most 5, at most 2, at most 1, or at most 0.5 mole %.

In one embodiment, the amount of a radical initiator present is in a range where the minimum and maximum amounts are selected from the embodiments above. For example, the amount present in the range 0.1 to 0.5 mole %.

In one embodiment, the radical initiator is selected from the group consisting of AIBN (azobisisobutyronitrile), ACPA (4,4'-azobis(4-cyanopentanoic acid)) and ACVA (4,4'-Azobis(4-cyanovaleric acid).

In one embodiment, the polymeric molecule is obtained or obtainable from the polymerisation of a composition comprising (i) and optionally (ii) and/or (iii) using the change transfer agent and/or radical initiator described.

In one embodiment, the polymeric molecule is obtainable or obtained from a composition described herein using a radical polymerisation process. In one embodiment, the In one embodiment, the polymerisation reaction is performed at elevated temperature. The reaction may be performed at a temperature of at least 30, at least 40 or at least 50° C. The reaction may be performed at a temperature of at most 100, at most 90 or at most 80° C. In one embodiment, the polymerisation reaction is performed in an organic solvent. The original solvent may be an ether solvent, for example 1,4-dioxane, or an alkyl alcohol solvent, for example ethanol. The polymerisation reaction may be performed at reflux temperature.

The concentration of the polymerisable mixture in the organic solvent may be at most 5.0, at most 2.0, or at most 1.5 M.

The concentration of the polymerisable mixture in the organic solvent may be at least 0.05, at least 0.1, at least 0.5 M, or at least 1.0 M.

In one embodiment, the concentration is in a range where the minimum and maximum amounts are selected from the embodiments above. For example, the concentration is in the range 1.0 to 2.0 M.

In one embodiment, the polymerisation reaction is performed for at least 1, at least 5 or at least 10 hours.

In one embodiment, the polymerisation reaction is performed for at most 72, or at most 48 hours.

The polymerisation reaction may be stopped using techniques familiar to those in the art.

Steps may include reaction mixture dilution and/or temperature reduction.

In one embodiment, the polymerisation reaction is performed for a time sufficient to obtain a polymeric molecule having a molecular weight as described herein.

In one embodiment, the polymerisation reaction is performed for a time sufficient to obtain a polymeric molecule having a plurality of guest molecules.

In one embodiment, the polymerisation reaction is performed for a time sufficient to obtain a polymeric molecule having one guest molecule.

The concentration of the polymerisable mixture refers to the total amount of monomer present (which includes (i), and (ii) and (iii), where present, and any other polymerisable monomers, where present) in moles, in unit volume of organic solvent (i.e. per liter).

In one embodiment, the polymer may be formed as a particle.

Particle

In one embodiment, the building block is a particle. The type of particle for use in the present invention is not particularly limited.

In one embodiment, the particle is a first building block and the particle is linked to a plurality of cucurbituril guest molecules.

In one embodiment, the particle is a second building block and the particle is linked to one or more cucurbituril guest molecules.

In one embodiment, the particle is a second building block and the particle is linked to a plurality of cucurbituril guest molecules.

Typically, the particle has a size that is one, two, three or four magnitudes smaller than the size of the capsule.

In one embodiment, the particle is a nanoparticle. A nanoparticle has an average size of at least 1, at least 5, or at least 10 nm in diameter. A nanoparticle has an average size of at most 900, at most 500, at most 200, or at most 100 nm in diameter.

In one embodiment, the nanoparticle has an average size in the range 1-100 nm or 5 60 nm in diameter.

The average refers to the numerical average. The diameter of a particle may be measured using microscopic techniques, including TEM.

In one embodiment, the particles have a relative standard deviation (RSD) of at most 0.5%, at most 1%, at most 1.5%, at most 2%, at most 4%, at most 5%, at most 7%, at most 10%, at moist 15%, at most 20% or at most 25%.

In one embodiment, the particle has a hydrodynamic diameter of at least 1, at least 5, or at least 10 nM in diameter.

In one embodiment, the particle has a hydrodynamic diameter of at most 900, at most 500, at most 200, or at most 100 nM in diameter.

The hydrodynamic diameter may refer to the number average or volume average. The hydrodynamic diameter may be determined from dynamic light scattering (DLS) measurements of a particle sample.

In one embodiment, the particle is a metal particle.

In one embodiment, the particle is a transition metal particle.

In one embodiment, the particle is a noble metal particle.

In one embodiment, the particle is or comprises copper, ruthenium, palladium, platinum, titanium, zinc oxide, gold or silver, or mixtures thereof.

In one embodiment, the particle is or comprises gold, silver particle, or a mixture thereof.

In one embodiment, the particle is a gold or a silver particle, or a mixture thereof.

In one embodiment, the particle is a gold nanoparticle (AuNP).

In one embodiment, the particle is or comprises silica or calcium carbonate.

In one embodiment, the particle is a quantum dot.

In one embodiment, the particle is or comprises a polymer. The polymer may be a polystyrene or polyacrylamide polymer. The polymer may be a biological polymer including for example a polypeptide or a polynucleotide.

In one embodiment, the particle comprises a material suitable for use in surface enhanced Raman spectroscopy (SERS). Particles of gold and/or silver and/or other transition metals are suitable for such use.

Gold and silver particles may be prepared using techniques known in the art. Examples of preparations include those described by Coulston et al. (Chem. Commun. 2011, 47, 164) Martin et al. (Martin et al. Langmuir 2010, 26, 7410) and Frens (Frens Nature Phys. Sci. 1973, 241, 20), which are incorporated herein by reference in their entirety.

The particle is linked to one or more guest molecules, as appropriate. Typically, where the particle is a first building block, it is provided at least with a plurality of guest molecules. Where, the particle is a second building block, it is provided at one or more guest molecules.

In one embodiment, a guest molecule may be covalently linked to a particle via a linking group. The linking group may be a spacer element to provide distance between the guest molecule and the particle bulk. The linker may include functionality for enhancing the water solubility of the combined building block and guest molecule construct. The linker is provided with functionality to allow connection to the particle surface. For example, where the particle is a gold particle, the linker has thiol functionality for the formation of a connecting gold-sulfur bond.

Alternatively, a guest molecule may be attached directly to the particle surface, through suitable functionality. For example, where the particle is a gold particle, the guest molecule may be attached to the gold surface via a thiol functionality of the guest molecule.

In one embodiment, the particle comprises solubilising groups such that the particle, together with its guest molecules, is soluble in water or is soluble in a water immiscible phase.

The solubilising groups are attached to the surface of the particle. The solubilising group may be covalently attached to the particle through suitable functionality. Where the particle is a gold particle, the solubilising group is attached through a sulfur bond to the gold surface. The solubilising group may be, or comprise, polyethylene glycol or amine, hydroxy, carboxy or thiol functionality.

In one embodiment, the building block is obtained or obtainable from a composition comprising:
  (i) a gold particle;
  (ii) a guest molecule together with a linking group that has thiol functionality; and
  (iii) a solubilising molecule having thiol functionality; and optionally further comprising (iv) a further guest molecule, together with a linking group that has thiol functionality.

In one embodiment, the amount of guest molecule present in the composition is at least 1, at least 5, at least 10 or at least 15 mole %.

In one embodiment, the amount of guest molecule present in the composition is at most 80, at most 50, or most 25 mole %.

A reference to mole % is a reference to the amount of guest molecule present as a percentage of the total amount of (ii) and (iii), and (iv) where present, in the composition.

The amount of (ii) present in the composition may be such to allow the preparation of a particle building block having a plurality of guest molecules.

Encapsulant

The nested capsule of the invention may be used to encapsulate a component (the encapsulant). In one embodiment there is provided a nested capsule comprising an encapsulant. The nested capsule is suitable for storing a component, and this component may be later released as required at a chosen location.

In one embodiment the first capsule holds an encapsulant (a first encapsulant).

In one embodiment the second capsule holds an encapsulant (a second encapsulant). Such an encapsulant is not held within the first capsule and is held in the remaining internal space that is not occupied by the first capsule. It will be appreciated that the first encapsulant is also held by the second capsule, except that the first encapsulant must also be present within the first capsule.

A third or any further additional encapsulant is an encapsulant provided within a third or additional capsule. A third encapsulant is not held within the second capsule and is held in the remaining internal space that is not occupied by the second capsule.

The term encapsulant is not intended to encompass a supramolecular capsule, such as a first capsule described herein. A reference to a second capsule holding an encapsulant is a reference to a second capsule holding a component that is in addition to a first capsule.

It is understood that a reference to an encapsulated component is not a reference to a solvent molecule. For example, the encapsulated component is not water or is not an oil or an organic solvent. It is also understood that a reference to an encapsulated component is not a reference to a host or a building block for use in the preparation of the capsule shell. Otherwise, the component is not particularly limited.

In one embodiment, each of the capsules in the nested capsule holds a solvent. The solvent may be water or oil, and the solvent may be phase used to prepare the microdroplet from which the capsule shell was formed. The solvent may be an organic solvent, such as chloroform.

The encapsulant is therefore a component of the capsule that is provided in addition to solvent that may be present within a shell.

In the methods of the invention the capsule shell is prepared from a composition comprising a host and one or more building blocks, as appropriate. Not all the host and one or more building blocks may react to form shell material. Additionally, the host and one or more building blocks may react to form a network, but this network may be not be included in the shell that forms the capsule. These unreacted or partially reacted reagents and products may be contained within the shell, and may be contained in addition to the encapsulant. Thus, the encapsulant is a component of the capsule that is provided in addition to unreacted or partially reacted reagents and products that may be present within the shell.

In one embodiment, an encapsulant has a molecular weight of at least 100, at least 200, at least 300, at least 1,000, at least 5,000 (1 k), at least 10,000 (10 k), at least 50,000 (50 k), at least 100,000 (100 k) or at least 200,000 (200 k).

In one embodiment, an encapsulant is a therapeutic compound.

In one embodiment, an encapsulant is a biological molecule, such as a polynucleotide (for example DNA and RNA), a polypeptide or a polysaccharide.

In one embodiment, an encapsulant is a polymeric molecule, including biological polymers such as those polymers mentioned above.

In one embodiment, an encapsulant is a cell.

In one embodiment, an encapsulant is an ink.

In one embodiment, an encapsulant is a carbon nanotube.

In one embodiment, an encapsulant is a particle. The particle may be a metal particle.

The size of a capsule is selected so as to accommodate the size of the encapsulant. Thus, the internal diameter (the distance from innermost wall to innermost wall) is greater than the greatest dimension of the encapsulant. The methods of the invention are adaptable to allow the size of each capsule in the nested capsule to be prepared at a desired size.

The size of the second capsule may be selected so as to accommodate a second encapsulant (where present) and one or more first capsules.

In one embodiment, the encapsulant has a detectable label. The detectable label may be used to quantify and/or locate the encapsulant. The label may be used to determine the amount of encapsulant contained with the capsule.

In one embodiment, the detectable label is a luminescent label. In one embodiment, the detectable label is a fluorescent label or a phosphorescent label.

In one embodiment, the detectable label is a visible.

In one embodiment, the fluorescent label is a rhodamine or fluorescein label.

In one embodiment, the encapsulant is selected from the group consisting of toxic molecules (such as nerve agents and heavy metals), hormones, herbicides, pesticides, antibodies, pathogens (such as viruses), adjuvants, gels, nanoparticles (including metal or non-metal particles), polymers (including synthetic and natural polymers), catalysts (organic, inorganic, and organometallic), adhesives and sealants.

A pathogen is an agent that is capable of causing disease in a host. The pathogen may be a virus, a bacterium, a fungus, or a prion.

In one embodiment, the encapsulants a virus.

The virus may be virus selected from a family selected from the group consisting of adenoviridae (e.g. adenovirus), herpesviridae (e.g. Herpes simplex, type 1 and type 2, and Epstein-barr), papillomaviridae (e.g. human papillomavirus), hepadnaviridae (e.g. Hepatitis B), flaviviridae (e.g. Hepatitis C, yellow fever, dengue, West Nile), retroviridae (e.g. immunodeficiency virus (HIV)), orthomyxoviridae (e.g. Influenza), paramyxoviridae (e.g. measles, mumps), rhabdoviridae (e.g. rabies), and reoviridae (e.g. rotavirus).

In one embodiment, the encapsulant is a microorganism

As noted above, in one embodiment, the encapsulant is a cell. The cell may be a prokaryotic or a eukaryotic cell.

The cell may be a mammal cell, such as a human cell, a rodent cell (e.g., a guinea pig, a hamster, a rat, a mouse) a lagomorph cell (e.g., a rabbit), an avian cell (e.g., a bird), a canine cell (e.g., a dog), a feline cell (e.g., a cat), an equine cell (e.g., a horse), a porcine cell (e.g., a pig), an ovine cell (e.g., a sheep), a bovine cell (e.g., a cow), a simian cell (e.g., a monkey or ape), a monkey cell (e.g., marmoset, baboon), an ape cell (e.g., gorilla, chimpanzee, orangutan, gibbon), or an ornithorhynchidae cell (e.g. platypus).

The cell may be a tumour cell, which may be a benign or malignant tumour cell.

Examples of eukaryotic cells include epithelial, endothelial, neural, skeletal, and fibroblast cells, amongst others.

In one embodiment, the encapsulant is a bacterium, such as a gram positive bacterium and a gram negative bacterium.

Examples of gram positive bacteria include *Corynebacterium, Mycobacterium, Nocardia, Streptomyces, Staphylococcus* (such as *S. aureus*), *Streptococcus* (such as *S. pneumoniae*), *Enterococcus* (such as *E. faecium*), *Bacillus, Clostridium* (such as a dill) and *Listeria.*

Examples of gram negative bacteria include *Hemophilus, Klebsiella, Legionella, Pseudomonas, Escherichia* (such as *E. coli*), *Proteus, Enterobacter, Serratia, Helicobacter* (such as *Helicobacter pylori*), and *Salmonella.*

In one embodiment, the encapsulant is an antibody.

The term "antibody" herein is used in the broadest sense and specifically covers monoclonal antibodies, polyclonal antibodies, dimers, multimers, multispecific antibodies (e.g., bispecific antibodies), and antibody fragments, so long as they exhibit the desired biological activity. Antibodies may be murine, human, humanized, chimeric, or derived from other species. An antibody is a protein generated by the immune system that is capable of recognizing and binding to a specific antigen. A target antigen generally has numerous binding sites, also called epitopes, recognized by CDRs on multiple antibodies. Each antibody that specifically binds to a different epitope has a different structure. Thus, one antigen may have more than one corresponding antibody. An antibody includes a full-length immunoglobulin molecule or an immunologically active portion of a full-length immunoglobulin molecule, i.e., a molecule that contains an antigen binding site that immunospecifically binds an antigen of a target of interest or part thereof, such targets including but not limited to, cancer cell or cells that produce autoimmune antibodies associated with an autoimmune disease. The immunoglobulin can be of any type (e.g. IgG, IgE, IgM, IgD, and IgA), class (e.g. IgG1, IgG2, IgG3, IgG4, IgA1 and IgA2) or subclass of immunoglobulin molecule. The immunoglobulins can be derived from any species, including human, murine, or rabbit origin.

"Antibody fragments" comprise a portion of a full length antibody, generally the antigen binding or variable region thereof. Examples of antibody fragments include Fab, Fab', F(ab')2, and Fv fragments; diabodies; linear antibodies; fragments produced by a Fab expression library, anti-idiotypic (anti-Id) antibodies, CDR (complementary determining region), and epitope-binding fragments of any of the above which immunospecifically bind to cancer cell antigens, viral antigens or microbial antigens, single-chain antibody molecules; and multispecific antibodies formed from antibody fragments.

The term "monoclonal antibody" as used herein refers to an antibody obtained from a population of substantially homogeneous antibodies, i.e. the individual antibodies comprising the population are identical except for possible naturally occurring mutations that may be present in minor amounts. Monoclonal antibodies are highly specific, being directed against a single antigenic site. Furthermore, in contrast to polyclonal antibody preparations which include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method, or may be made by recombinant DNA methods. The monoclonal antibodies may also be isolated from phage antibody libraries.

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity In one embodiment, the antibody is an antibody-drug conjugate (ADC).

The antibody may be suitably labelled for detection and analysis, either whilst held in the capsule, of for later use, when the antibody is released.

In one embodiment, the encapsulant is a hormone. The hormone may a peptidic hormone, such as insulin or growth hormone, or a lipid hormone, such as a steroid hormone, for example prostaglandin and estrogen.

In one embodiment, the encapsulant is a polypeptide. In one embodiment, the polypeptide is a protein. In one embodiment the protein has catalytic activity, for example having ligase, isomerase, lyase, hydrolase, transferase or oxidoreductase activity.

In one embodiment, the encapsulant is a polymer. In some embodiments, the capsule shell of the present invention includes a building block that is a functionalised polymer. Where such a building block is present, a polymer that is an encapsulant differs from the building block. In one embodiment, the encapsulant polymer is not suitable for forming a non-covalent link with a cucurbituril.

In one embodiment, the encapsulant is a metal particle.

In one embodiment, the nanoparticle is or comprises a noble metal.

In one embodiment, the nanoparticle is or comprises a transition metal.

In some embodiments, the capsule shell of the present invention includes a building block that is a functionalised particle. Where such a building block is present, a particle that is an encapsulant differs from the building block. In one embodiment, the encapsulant particle is not suitable for forming a non-covalent link with a cucurbituril.

In one embodiment, the nanoparticle is a gold nanoparticle (AuNP) or a silver nanoparticle (AgNP), or a nanoparticle comprising both silver and gold.

Generally, the particle is substantially spherical. However, particles having other shapes may be used, if appropriate or desirable.

In one embodiment, the nanoparticle has a diameter of at most 500 nm, at most 200 nm, at most 150 nm, at most 100 nm, at most 80 nm, or at most 70 nm.

In one embodiment, the nanoparticle has a diameter of at least 1 nm, at least 2 nm, at least 55 nm, at least 10 nm, at least 15 nm, at least 20 nm, at least 30 nm, or at least 40 nm.

In one embodiment, the diameter of the particle is in a range where the minimum and maximum rates are selected from the embodiments above. For example, the diameter is in the range 1 to 100 nm, or for example in the range 10 to 100 nm. For example, the diameter is in the range 2 to 500 nm In one embodiment, the nanoparticle has a diameter of about 20 nm.

The average refers to the numerical average. The diameter of a particle may be measured using microscopic techniques, including TEM.

The particles used in the present invention are sustainably monodisperse or have a very low dispersity. In one embodiment, the particles have a relative standard deviation (RSD) of at most 0.5%, at most 1%, at most 1.5%, at most 2%, at most 4%, at most 5%, at most 7%, at most 10%, at moist 15%, at most 20% or at most 25%.

In one embodiment, the particle has a hydrodynamic diameter of at least 5 nm, at least 10 nm, at least 15 nm, at least 20 nm, at least 30 nm, at least 40 nm.

In one embodiment, the particle has a hydrodynamic diameter of at most 500 nm, at most 200 nm, at most 150 nm, at most 100 nm, at most 80 nm, or at most 70 nm.

The hydrodynamic diameter may refer to the number average or volume average. The hydrodynamic diameter may be determined from dynamic light scattering (DLS) measurements of a particle sample.

The size of the particle and the composition of the particle may be selected to provide the most appropriate or beneficial surface enhanced effect.

Gold and silver particles may be prepared using techniques known in the art. Examples of preparations include those described by Coulston (Coulston et al *Chem. Commun.* 2011, 47, 164) and Martin (Martin et al. *Langmuir* 2010, 26, 7410) and Frens (Frens *Nature Phys. Sci.* 1973, 241, 20), which are incorporated herein by reference in their entirety.

In one embodiment, an encapsulant is a polymer. In one embodiment, the polymer is not a polymer that is present as building block in the capsule shell. Otherwise, the polymer is not particularly limited.

In one embodiment, an encapsulant is a fragrance compound or a fragrance composition. A fragrance compound or composition has suitable odorant properties for use in a perfume.

In one embodiment, an encapsulant is a flavourant compound or a flavourant composition.

A flavourant may be or include a flavour enhancer, such as a sweetener.

In one embodiment, an encapsulant is an oil, such as an essential oil. Examples of essential oils include those obtained or obtainable from sweet orange, peppermint, lemon and clove, amongst others.

In one embodiment, an encapsulant is itself a vehicle for holding an encapsulant within. For example, the encapsulant may be a liposome, micelle, or vesicle. The liposome, micelle, or vesicle may hold an encapsulant, such as one of the encapsulants described herein.

Suitably loaded liposomes, micelles, or vesicles may be prepared using standard techniques known in the art. The loaded liposome, micelle, or vesicle may then be encapsulated into the supramolecular capsules of the invention using the methods described herein.

A liposome, micelle, or vesicle is not a capsule, such as described herein. A liposome, micelle, or vesicle does not have a shell of material that that is a supramolecular cross-linked network.

As described herein the nested capsule of the invention is suitable for use as a reactor. The method of preparing the capsule as described herein allows for the compartmentalisation of a second capsule. Thus, a first encapsulant may be provided in a first capsule, and is kept apart from the second encapsulant, which is held in the second capsule. The shell of the first capsule provides a barrier between the first and second encapsulants. The first capsule may be degraded as described herein, thereby to allow the first encapsulant to exit the first capsule and enter into the larger second capsule space. Here, it is able to interact, such as react, with the second encapsulant, to form a product. This product may be later from the capsule by disruption of the second capsule shell.

Where the capsule is for use as a microreactor it is understood that the composition of the second capsule inner space will change over time as the reagents react to form a product, along with associated by-products, if any. As will be apparent, the amount of reagent will decrease as the reaction progresses.

Methods of Preparation—Nested Capsules

The preparation of a capsule having a shell of material that is a supramolecular cross-linked network is described by some of the present inventors in Zhang et al., *Science* 2012, 335, 690 and PCT/GB2012/051787, the contents of both of which are hereby incorporated by reference in their entirety.

The techniques for the formation of a single capsule may be adapted for use in the formation of the nested capsules describe herein.

The present inventors have established that supramolecular capsules, such as those previously described, may themselves be incorporated into a larger supramolecular capsules. Alternatively, supramolecular capsules may be prepared in order to hold, or encapsulate a cargo that is a smaller supramolecular capsule.

Thus, in one example, a nested capsule of the invention may be prepared by populating the flow streams in the work of Zhang et al. with appropriate components.

Zhang et al. describe the preparation of a capsule having a shell of material that is a network formed from the ternary complexation of CB[8] with a polymer building block having naphthol guest molecules (first guests) and a gold nanoparticle building block decorated with methyl viologen guest molecules (second guests). It will be appreciated that the gold nanoparticle may be replaced with another building block, such as a polymer building block. Similarly, the polymer building block may be provided with additional second guest molecules. Here the polymer may form intramolecular and intermolecular links thereby to generate a network.

The second building block is optional here.

Separate solutions of the building blocks and the CB[8] are brought into contact in a combined fluid flow. This combined flow is then contacted with an immiscible flow at a T-junction to generate a dispersion of the combined solution in the immiscible phase. The network is formed at the interface of the droplet with the immiscible phase.

Such techniques may be used to form a capsule, such as a first capsule, with appropriate adaptations for the building blocks, the guests, and the host.

Zhang et al. also describe the encapsulation of dextran into a capsule. Also described is the incorporation of *E. coli* cells into a capsule. The encapsulant is provided into the combined flow, and is present in the droplet with the capsule shell material forming around it. Thus, the techniques may be used to form a capsule, such as a first capsule, holding an encapsulant.

It will be appreciated that the encapsulant may itself be a capsule, such as a first capsule. Thus, a nested capsule may be formed in this method by the incorporation of a first capsule into a droplet with the second capsule material forming around it.

The first capsule may be prepared in a preliminary preparation using the techniques described by Zhang et al. The first capsules may be prepared and stored until required.

Alternatively, the first capsules may be developed in a flow system and then immediately delivered into a flow system for the preparation of the second capsule. This may be referred to as an in-line synthesis.

Where a first capsule is provided in a fluid flow that first capsule may hold a first encapsulant. This first capsule may be provided in a combined fluid flow with a second encapsulant, and the components for the formation of the second capsule. The second encapsulant is therefore present in a droplet with the second capsule shell material forming around it. Thus, the techniques may be used to form a second capsule holding a second encapsulant and a first capsule, which itself holds a first encapsulant. The relative flow rate and the concentration of the fluid flow comprising the first capsule may be altered thereby to allow the incorporation of a plurality of first capsules into the droplet, which in turn leads to the presence of a plurality of first capsules in each second capsule.

These techniques may be repeated as is apparent to provide a third capsule holding a second capsule, which itself holds a first capsule, with each capsule each holding a third, second and first capsules as appropriate.

The first capsule may be pre-formed. It may then be simply encapsulated into the second capsule during the formation of the second capsule shell.

The first capsule may be formed substantially simultaneously with the second capsule. Indeed, the first capsule may be formed after the second capsule is formed. In both scenarios, the reagents for the formation of the first capsule are encapsulated into the second capsule during the formation of the second capsule shell.

In principle, a nested capsule may be prepared by a simple bulk preparation method. Thus, rather than using fluid flows to bring together material and generate droplets, material may simply be dispersed by agitation techniques that mix phases.

The bulk preparation method is useful for generating product on a large scale. However, there is a great variety in terms of the products produced. Thus the capsules may differ greatly in terms of their size, and may differ greatly in terms of the material that each capsule holds, including for examples the amount of encapsulant held and the amount of smaller capsules held.

The flow system provides exquisite control to the user, and allows for the reproducible formation of capsules having a desired size (substantially monodisperse), composition and cargo. Modern flow systems also allow the production of droplets and double emulsions on a large scale.

The preparation of nested supramolecular capsules, as with the formation of supramolecular capsules, may be undertaken using microdroplet techniques, for example using adaptations of the methods described by Zhang et al., *Science* 2012, 335. The basic step for the formation of a single capsule is to disperse a first fluid as droplets in a continuous phase of a second fluid. The components for the formation of the shell material may be provided within the second solvent, and form the shell at the boundary between first and second solvents. Drying the droplets, such as to at least partially remove the first fluid by evaporation, may assist the formation of the shell at the solvent boundary.

The capsule that is formed in this basic step may itself be incorporated into a larger, second capsule, thereby to form a nested capsule of the invention. The formation of the larger capsule includes the step of dispersing the second fluid, including the dispersed first capsule (or dispersed first droplets) in a continuous phase of a third fluid. The components for the formation of the shell material may be provided within the second fluid, and form the shell at the boundary between second and third fluids. Again, drying the second droplets, such as to at least partially remove the second solvent by evaporation, may assist the formation of the shell at the solvent boundary.

The stage at which the capsule shell is formed may depend on the fluids (which may be referred to as solvents) used in the methods. The shell of the first (inner) capsule may form before encapsulation into a second capsule. The shell of the first (inner) capsule may form before the shell of the second (outer) capsule. The shell of the second (outer) capsule may form before the shell of the first (inner) capsule. Such is shown in the worked examples of the present case.

An encapsulant may be included in the first and second fluids, as necessary to yield nested capsules holding an encapsulant.

The first and the second fluids are immiscible. The second and the h d fluids are immiscible.

The first and third fluids may be the same, although this is not essential.

Typically, at least one of the first, second and third fluids is an aqueous solvent (water). The first or the second may be an aqueous solvent (water).

Each of the first, second and third fluids is a liquid.

The first solvent may have a boiling point that is lower than the boiling point of the second solvent. For example, the first solvent may be chloroform, or another low boiling organic solvent, and the second solvent may be water. Where this is the case, it is possible to preferentially from the first (inner) capsule before the second (outer) capsule.

The second solvent may have a boiling point that is lower than the boiling point of the third solvent. For example, the second solvent may be water, and the third solvent may be a fluorinated oil.

The first solvent may have a boiling point that is higher than the boiling point of the second solvent. For example, the first solvent may be water, and the second solvent may be chloroform, or another low boiling organic solvent, or the first solvent may be an oil, and the second solvent may be water. Where this is the case, it is possible to preferentially from the second (outer) capsule before the first (inner) capsule.

In one embodiment, at least one solvent is a fluorinated oil, such as a perfluorinated oil. The third fluid id typically an oil.

It follows from the above, that the nested capsules that are prepared according to the present invention may include capsules holding a solvent within their internal cavity. During the preparation process, the solvent within the capsule may be at least partially removed by e.g. drying the droplets and the capsules. It will be appreciated that an inner capsule, such as the first capsule, may hold a first solvent, whilst an outer capsule, such as the second capsules, may hold a second solvent, with an inner capsule dispersed within that second solvent. Thus, a nested capsule is capable of providing two alternative regions (or domains).

The methods of the invention may be used advantageously to prepare nested capsules where the first and second shells differ in their composition, for example, differ in the nature of the building block. The methods of the invention allow such nested capsules to be prepared.

The present inventors are able to control the formation of a capsule shell at the boundary between a dispersed first fluid (droplet) in a continuous second fluid. The present inventors have shown that it is possible to direct certain building blocks to this boundary, optionally to the exclusion of other building blocks. This control makes use of the physical and chemical characteristics of the building blocks. More specifically, the boundary is designed such that certain polymeric molecules will be attracted to that boundary, whilst other polymeric molecules will not, or will be repulsed. For example, charge interactions may be used as the basis for attracting (or repulsing) a polymeric molecule to (or from) the boundary.

For example, where a building block having charged functional groups is provided in a second fluid, it may be attracted to a boundary of the second fluid with a first fluid where the first fluid contains functional groups that are of opposite charge, or there are compounds present in the fluid that are of opposite charge. The reaction of the building block in a complexation reaction results in the formation of a shell at the boundary of the first and second fluid. Where the second solvent also contains other building blocks that are uncharged or oppositely charges, those building blocks are not expected to congregate at the boundary between the first and second fluids.

It will be appreciated that a building block having charged functional groups may be provided in the first fluid, and may be attracted to the boundary with the second fluid, where the second fluid has functional groups that are of opposite charge, or there are compounds present in the fluid that are of opposite charge.

A fluid may inherently possess suitable functionality to attract a building block (held in another fluid) to a boundary. For example, the solvent chloroform may be used (for example as a first fluid) to attract a building block having positively charged groups that is held in an aqueous solution (the second fluid) to the fluid boundary.

Charged surfactants may also be used to selectively draw building blocks to the fluid interface. Where one of the fluids, such as the second fluid, includes a surfactant, it will locate to the boundary of the first and second fluids during the droplet formation step. If that surfactant has positively charged groups, it will be capable of attracting negatively charged building blocks to the boundary, such as building blocks present in the first fluid. Similarly, if the surfactant has negatively charged groups, it will be capable of attracting negatively charged building blocks to the boundary. If a neutral surfactant is used, there is no selective draw of charged building blocks to the interface. As described herein, the inventors have been able to demonstrate the selective distribution of a building block across the interface of a dispersed droplet in a continuous phase.

References to charge interactions above, may also include references to other electrostatic interactions as appropriate.

The inventors have found that the movement of a charged building block within a droplet to a droplet boundary surface having an oppositely charged surfactant is very quick within the timescale of a microfluidic experiment. The inventors have also found that the attractive distribution of the building block across the interface is reversible removal of the surfactant causes the building block to disperse from that interface.

The location of the building blocks at the fluid interfaces ensures that a capsule can be formed. Where a building block is evenly distributed in a solvent, the complexation of that building block may lead to the formation of a hydrogel-like network rather than a capsule.

In one example, a nested capsule may be formed having a positively charged building block in the shell of the first capsule and a negatively charged building block in the shell of the second capsule. The method of preparation includes the step of dispersing a first fluid as droplets in a continuous phase of a second fluid. The first fluid contains a negatively charged surfactant. The second fluid contains the positively charge building block and the negatively charged building block. The second fluid (containing the first fluid as droplets) is dispersed as droplets in a continuous phase of a third fluid. The third fluid contains a positively charged surfactant.

The surfactant in the first fluid draws the positively charged building block to the interface of the first and second fluids. The surfactant in the third fluid draws the negatively charged building block to the interface of the second and third fluids. Accordingly, there is little or no building block dispersed in the second fluid the building blocks are located at the interfaces. Thus where a suitable host is provided, and the building blocks have suitable guest functionality, complexation of the building blocks provides a shell of material at the interfaces thereby leading to a nested capsule.

Altering the location of the charge surfactants will alter the location of the charged building blocks. To form a nested capsule having a negatively charged building block in the shell of the first capsule and a positively charged building block in the shell of the second capsule simply requires placing a positively charged surfactant in the first solvent and a negatively charged surfactant in the third fluid.

The formation of nested capsules in this way is shown schematically in FIG. 22.

In one aspect of the invention there is provided a method of synthesising a nested capsule, the method comprising the steps of:
  (i) forming a first droplet of a first fluid in a continuous phase of a second fluid;
  (ii) forming a second droplet of the second fluid in a continuous phase of a third fluid, wherein the second droplet contains the first droplet or a capsule obtained therefrom;
  (iii) providing a first building block having guest functionality at the interface of the first fluid and the second fluid, and permitting the first building block to complex with a host at the interface;
  (iv) providing a second building block having guest functionality at the interface of the second fluid and the third fluid, and permitting the first building block to complex with a host at the interface.

The host may be provided in the second fluid. It is therefore available to form complexes at the interfaces of the second fluid with the first and second fluids.

The formation of supramolecular complexes in step (iii) may occur before, after or simultaneously with the formation of supramolecular complexes in step (iv).

The first building block may be provided in the first or second fluids. The second building block may be provided in the second or third fluids.

The first and second building blocks are each provided at an interface of fluids at the time of complexation. A building block in a fluid may locate to the interface based on an attraction between the building block and the other fluid at the interface (e.g. hydrophilic-hydrophilic or hydrophobic-hydrophobic interactions), or a compound within the other fluid at the interface (e.g. a surfactant)

A building block is not dispersed in a solvent at the time of complexation. The building block is predominantly located at an interface. Thus, complexation forms a supramolecular network at the interface, thereby generating a shell of material. Where a polymer is dispersed in throughout a fluid, the complexation reaction will generate a gel of material, such as a hydrogel.

A building block may be attracted to an interface. For example, the building block may have an electrostatic interaction with a solvent at the interface, or a compound, such as a surfactant, that is located at the interface.

The first and second building blocks may be provided in the second fluid.

Additional building blocks having guest functionality may be provided at each interface.

The choice of fluids in the present case is not particularly limited. Clearly, the dispersed and continuous phases discussed above arise from the immiscibility of the fluids in question. Typically, one fluid, such as the first or second fluids is an aqueous phase. Thus, other phases are immiscible with this water phase. As noted previously there are benefits to selecting fluids (liquids) based on respective boiling points, as such may be used to control the order in which the capsule shells form.

A water immiscible phase may have an oil as a principal component. In one embodiment, the oil is a hydrocarbon-based oil. In one embodiment, the oil is a perfluorinated oil. In one embodiment, the oil is a silicone oil.

A water immiscible phase may have as a principal component an organic solvent. For example, the organic solvent is selected from chloroform and octane.

Other processing adaptation will be apparent from a combination of the teaching provided by the worked examples in the present case together with Zhang et al., *Science* 2012, 335, 690.

Use of Nested Capsules

The nested capsules of the invention may be used to hold one or more encapsulants. Each encapsulant may be held within an individual capsule, and prevented from interacting with an encapsulant held within another capsule of the nested capsule. In this way the nested capsule may be used to store and separate encapsulants that are inter-reactive. The nested capsules of the invention are stable and may be used to store encapsulants until required, which may be an hours, a day or a week after the nested capsules is prepared.

The nested capsules of the invention are suitable for use in transporting encapsulants to a desired location.

Thus in one aspect, the present invention provides a method of delivering an encapsulant to a location, the method comprising the steps of:
(i) providing a nested capsule of the invention, which comprises an encapsulant;
(ii) delivering the capsule to a location; and
(iii) permitting release of the encapsulant from the capsule at the location.

In a further aspect, the present invention provides a method of delivering a plurality of encapsulants to one or more locations, the method comprising the steps of:
(i) providing a nested capsule of the invention, the nested capsule comprising a first capsule held within a second capsule, and each of the first and second capsules having a shell of material that is a supramolecular cross-linked network, wherein the first capsule holds a first encapsulant and the second capsule holds a second encapsulant;
(ii) delivering the nested capsule to a location;
(iii) permitting release of the second encapsulant from the second capsule at a first location; and
(iv) subsequently permitting release of the first encapsulant from the first capsule at the first location or a second location.

In a related aspect, the present invention provides a method of delivering a plurality of encapsulants to a location, the method comprising the steps of:
(i) providing a nested capsule of the invention, the nested capsule comprising a first capsule held within a second capsule, and each of the first and second capsules having a shell of material that is a supramolecular cross-linked network, wherein the first capsule holds a first encapsulant and the second capsule holds a second encapsulant;
(ii) delivering the nested capsule to a location; and
(iii) permitting release of the second encapsulant from the second capsule at a first location and simultaneously permitting release of the first encapsulant from the first capsule, thereby to deliver the first and second encapsulants to the location.

In another aspect, the present invention provides a method of synthesis, the method comprising the steps of:
(i) providing a nested capsule of the invention, the nested capsule comprising a first capsule held within a second capsule, and each of the first and second capsules having a shell of material that is a supramolecular cross-linked network, wherein the first capsule holds a first encapsulant and the second capsule holds a second encapsulant;
(ii) permitting release of the first encapsulant from the first capsule into the second capsule, thereby to permit the first encapsulant to interact with the second encapsulant to yield a product; and
(iii) optionally permitting the release of the product from the second capsule.

In one embodiment, a location is in vivo.

In one embodiment, a location is ex vivo.

In one embodiment the release of an encapsulated component is in response to an external stimulus.

In one embodiment, the external stimulus is selected from the group consisting of competitor guest compound, light, temperature change, oxidising agent, and reducing agent.

In one embodiment the release of an encapsulated component is in response to a change in the local conditions.

In on embodiment, the change in local conditions may be a change in pH, a change in temperature, a change in oxidation level, change in concentration, or the appearance of a reactive chemical entity.

The release of encapsulant from a capsule in the nested capsule requires the disruption of the network of the capsule shell. The at least partial disruption of the network generates suitably large pores in the shell to allow an encapsulant to exit a capsule. Under appropriate conditions, the disruption of the network may be total, resulting in the complete disintegration of a shell and therefore the capsule. The release of an encapsulant from the nested capsule requires the disruption of the outer shell, such as the shell of the second capsule.

In one embodiment, the release of the encapsulant is achieved by disrupting the complex formed between the host and the guest molecule or molecules. In one embodiment, a compound covalently linked to a competitor guest molecule is provided at the release location. The competitor guest molecule displaces a guest molecule of a building block thereby to disrupt the network that forms the capsule shell. Such disruption may cause pores to appear in the shell, through which the encapsulated compound may pass through and be released. In one embodiment, the competitor guest molecule causes an extensive disruption of the capsule shell.

In preferred embodiments of the invention an encapsulant is a relatively large component, such as a biopolymer (such as a polynucleotide, polypeptide or polysaccharide) or a cell. The pores in the shell are typically of sufficient size to prevent such encapsulants from passing through a shell.

In some embodiments of the invention, the networks of the first and the second capsules may be identical or very similar, or at least the complex of the host and the guest/s may be identical, or very similar. Thus, the conditions necessary to cause a disruption of the network of the first capsule will also cause disruption of the network of the second capsule. Similarly, the conditions necessary to cause a disruption of the network of the second capsule will also cause disruption of the network of the first capsule. Thus, in one step the networks of all the capsules in the nested capsule may be disrupted, thereby to simultaneously release the encapsulant held by the first capsule and the second capsule. In this way, the encapsulants are released from the nested capsule at substantially the same time.

Capsules that are very similar are capsules having substantially the same reactivity to the disrupting conditions.

Alternatively, the networks of the first and the second capsules may be non-identical, for example the complex of the host and the guest/s may be non-identical, or more particularly the guest/s may be different. The first and second capsules will therefore have different reactivities and this may be exploited to allow the selective disruption of one capsule shell without causing the disruption of the other capsule shell. In this embodiment the capsules may be referred to as orthogonal.

As shown herein, different complexes have different responses to light, heat, redox conditions, and/or guest competition. These responses may be used advantageously to allow the sequential disruption of the first and second capsules. Consequently, this allows encapsulants to be released in sequence.

In one embodiment, the first capsule is disruptable in response to a disrupting condition selected from light, heat, redox conditions, or guest competition. In this embodiment, the second capsule is not disruptable to the selected disrupting condition.

In one embodiment, the second capsule is disruptable in response to a disrupting condition selected from light, heat, redox conditions, or guest competition. In this embodiment, the first capsule is not disruptable to the selected disrupting condition.

The first and second capsules may have different reactivities in response to one disrupting condition, but may have similar reactivities in response to another disrupting condition.

In one embodiment of the invention there is provided method for the sequential release of encapsulants from a nested capsule of the invention, where the first capsules holds a first encapsulant and the second capsule holds a second encapsulant, the method comprising the steps of (i) disrupting the shell of the second capsule thereby to release the second encapsulant; (ii) subsequently disrupting the shell of the first capsule thereby to release the first encapsulant.

Step (ii) may be performed as and when required. For example, step (ii) may be performed 5 minutes, 10 minutes, 15 minutes, 30 minutes, 1 hour, 12 hours, 1 day or 1 week after the release of the second encapsulant.

It is not necessary for the first and second encapsulant to be different, and they may be same. It may be useful to have the same encapsulant within each of the first and second capsules. The nested capsule allows the timed release of encapsulant. Thus, the same encapsulant may be released at chosen times at the same location, or alternatively an encapsulant may be released from the second capsule at one location, the remaining capsule may be taken to a further location, and encapsulant may be released from the first capsule (and ultimately from the second capsule also) at the further location.

In one embodiment of the invention there is provided method for the release of contents from a nested capsule of the invention, where the first capsules holds a first encapsulant and the second capsule holds a second encapsulant, the method comprising the steps of (i) disrupting the shell of the first capsule thereby to release the first encapsulant into the second capsule; (ii) subsequently disrupting the shell of the second capsule thereby to release the contents of the second capsule.

Step (i) may permit the first encapsulant to interact with the second encapsulant. For example, covalent or non-covalent bond may be formed between the first and second encapsulants to give rise to a new product. In another embodiment, one of the first and second encapsulants may be a catalyst for the reaction of the other of the It will be appreciated that one of the first and second capsules may be provided with a plurality of different encapsulants. These different encapsulants may be reactive only in the presence of an encapsulant supplied from the other capsule.

Step (ii) may be performed as and when required. For example, step (ii) may be performed 5 minutes, 10 minutes, 15 minutes, 30 minutes, 1 hour, 12 hours, 1 day or 1 week after the release of the second encapsulant. For example, the disruption of the second shell may be performed as and when a suitable quantity of product has been formed from the reaction of the first and second encapsulants.

As described herein, an encapsulant may be provided with a detectable label. The detectable label allows the location of the encapsulant to be determined, and may also be used to determine whether or not the encapsulant has reacted.

The distribution of a first or second encapsulant may indicate to the user whether a capsule shell has been disrupted. For example, prior to the disruption of the first capsule, the first encapsulant remains localised in a portion of the inner space of the second capsule. After disruption of the first capsule, the first encapsulant is able to distribute into the larger second capsule space. Similarly, the change in distribution of the second encapsulant may be indicative of the disruption of the first capsule.

Where the second capsule if disrupted, the distribution of the second encapsulant into the wider environment will be indicative of that disruption. Similarly, the distribution of the first encapsulant into the wider environment will be indicative of the second capsule disruption (and the first capsule disruption also).

It is not necessary for the encapsulants to be labelled in order to tell whether a capsule shell is disrupted. The capsule shells may be labelled, and the disruption of the shells may be determined from the loss of shell structure. The capsule disruption may also be visible by eye.

Covalent Links and Cross-Links

As described above, the shell of a capsule includes building blocks that are linked or cross-linked by non-covalent bonding. For example, a host such as CB[8] may be used as a handcuff to hold first and second guest molecules from the same or different building blocks.

As an alternative to, or in addition to, the non-covalent links, the building blocks may be linked or cross-linked by covalent bonding. The presence of covalent bonds within a network may provide a shell material having greater strength over those networks that are formed from non-covalent interactions only. In one embodiment, the covenant bonds are formed between the guest molecules of the building blocks.

The present inventors have found that the formation of the covalent bonds between building blocks may be achieved via a guest-host intermediate. Thus, in a first step a supramolecular polymer may be formed where a ternary complex having a host non-covalently holds first and second guest molecules from the same or different building blocks. The first and second guest molecules are permitted to react, thereby to form a covalent bond linking the building blocks. A supramolecular polymer is a polymer where two building blocks are held together by a non-covalent complex.

In preferred embodiments of the invention the host in the ternary complex has a cavity that is a through channel in the molecule. Thus, guest molecules may enter the cavity from one of a plurality of channel openings. For example, cucurbituril compounds such as CB[8] have two openings to a central cavity and each opening is accessible.

Hosts having such a through channel may accommodate two guests in a ternary complex in a head-to-tail or head-to-head arrangement. In the head-to-head arrangement the two guests have entered occupy the same opening. In the head-to-tail arrangement the two guests have entered different openings in the host.

In one embodiment, the guests are held in a head-to-tail arrangement within the cavity of the host. It follows that the formation of a covalent bond between the guests thereby traps the host on the conjoined building blocks. The host may continue to non-covalently bond to the guest formed from the reaction of the first and second guests.

The building blocks, such as the building block first and second guests, react in response to an external stimulus, such as light, heat or change in pH. In one embodiment, the reaction is initiated by light irradiation, for example UV light irradiation.

The first and second reagents may participate in a pericyclic reaction, thereby to form a covalent bond.

The first and second guest molecules may participate in a cycloaddition reaction, thereby to form a covalent bond. For example, the cycloaddition reaction may be a [4+4] or a [2+2] cycloaddition reaction.

In one aspect there is provided a method of covalently inking or cross-linking a building block, the method comprising the steps of:
(i) providing a non-covalently linked building block or building block, wherein the non-covalent linked is formed from a ternary complex of a host holding first and second guest molecules provided on the building blocks;
(ii) permitting the building blocks to react, thereby to form a covalent bond linking the building block or the building blocks.

Thus, in one embodiment, there is provided a method of preparing a capsule having a shell of material that is a cross-linked network, wherein the network is formed from the covalent crosslinking of a building block and/or the covalent linking of a building block to another building block, the method comprising the steps of:
(i) providing a capsule having a shell of material that is a supramolecular cross-linked network of a building block or building blocks, wherein the shell is obtainable from the ternary complexation of a host and first and second guest molecules provided on the building blocks;
(ii) permitting the building blocks to react hereby to form a covalent bond linking the building block or the building blocks.

In one embodiment, step (i) provides a nested capsule having a first capsule held within a second capsule, wherein one of the first and second capsules has a shell of material that is a supramolecular cross-linked network of a building block or building blocks, wherein the shell is obtainable from the ternary complexation of a host and first and second guest molecules provided on the building blocks. After step (ii) is performed, a nested capsule is produced where one of the first and second capsules has a shell that is a covalent cross-linked network.

In one embodiment, step (i) provides a nested capsule having a first capsule held within a second capsule, wherein each of the first and second capsules has a shell of material that is a supramolecular cross-linked network of a building block or building blocks, wherein the shell is obtainable from the ternary complexation of a host and first and second guest molecules provided on the building blocks. After step (ii) is performed, a nested capsule is produced where each of the first and second capsules has a shell that is a covalent cross-linked network.

In one embodiment, step (ii) in either of the methods above permits the first and second guest molecules to react, thereby to form a covalent bond linking the building block or the building blocks.

In one embodiment, the host in either of the methods above is a cucurbituril compound.

In one embodiment, the host in either of the methods above is CB[8].

In step (ii) it is not necessary for all the first and second building blocks to react. The product may retain some ternary complexes where the host holds first and second guest molecules.

In one embodiment, the first and second guest molecules are held in a head-to-tail arrangement in the cavity of the host.

In one embodiment, the first and second guest molecules are capable or participating in a cycloaddition reaction.

In one embodiment, each of the first and second guest molecules includes an anthracene moiety. As shown herein, two anthracene-containing guest molecules held by a host in a ternary complex may undergo a cycloaddition reaction, thereby to form a covalent link between the guest molecules. The product formed from the reaction of the first and second guest molecules may be referred to as the addition product.

In one embodiment, each of the first and second guest molecule includes a cinnamic acid moiety.

The addition product may become a guest that that is non-covalently held in a binary complex together with the host. Thus, the addition product may be retained within the cavity of the host.

It will be appreciated that the addition product and the host may separate (dissociate). This does not result in the loss of structural integrity to the network. The formation of the covalent bond between first and second guest molecules provides a link between building blocks.

The host is therefore no longer required to link together the building blocks.

The dissociation and movement of the host from the addition product may in practice be limited. The formation of the addition product effectively contains the host on the cross-linked building blocks, and its movement may be limited or prevented by structural and functional features of the addition product, or other features of the building block.

The formation of a covalent bond between first and second guest molecules yields a single guest, and a resulting complex may be referred to as a binary complex.

It is not necessary for the covalently linked first and second guest molecules to have a high association constant. Once the covalent link is made there is no requirement for the host to non-covalently bind to the addition product: the covalent bond provides a structural link between building blocks that will not dissociate, and the host is no longer required to maintain the integrity of the link between the building blocks.

In one embodiment, the reaction is a light- or a heat-initiated reaction.

Light may refer to UV or visible light. Heat refers to a reaction temperature that is above the reaction temperature for the preparation of the supramolecular cross-linked network. Heat may refer to a reaction temperature above room temperature. Heat may refer to a reaction temperature of 50° C. or above, 60° C. or above, or 70° C. or above.

The network is formed from the covalent crosslinking of a building block and/or the covalent linking of a building block to another building block thereby forming the network Other Preferences Each and every compatible combination of the embodiments described above is explicitly disclosed herein, as if each and every combination was individually and explicitly recited.

Various further aspects and embodiments of the present invention will be apparent to those skilled in the art in view of the present disclosure.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Unless context dictates otherwise, the descriptions and definitions of the features set out above are not limited to any particular aspect or embodiment of the invention and apply equally to all aspects and embodiments which are described.

Certain aspects and embodiments of the invention will now be illustrated by way of example and with reference to the figures described above.

% may refer to wt % or mol %, as context dictates.

Results and Discussion

Nested Capsules

Figure 2:
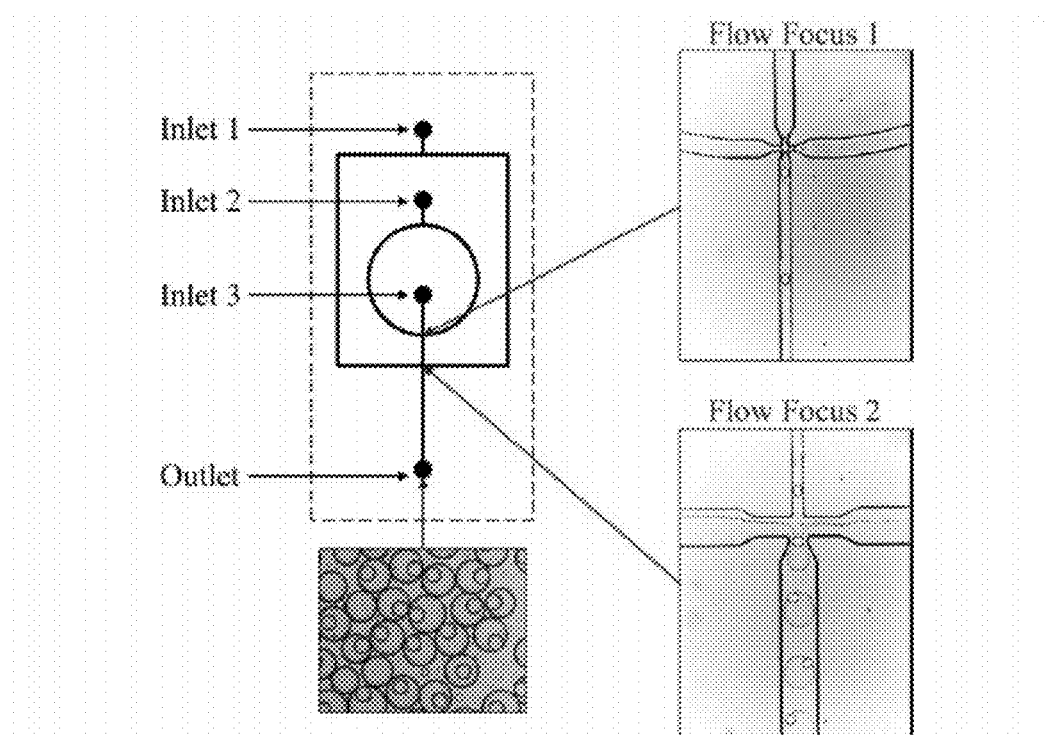
FIG. 2 is a schematic of a flow apparatus suitable for use in the preparation of a nested capsule. The flow apparatus has three inlets for the supply of three fluid flows, which may be used to prepare a double emulsion droplet, from which a nested capsule having a first capsule held within a second capsule may be formed. Inlet 3 supplies the fluid for the inner (first) droplet, inlet 2 supplies the fluid for the outer (second) droplet and inlet 1 supplies the fluid for the continuous phase.

As described herein, a basic nested capsule having a first capsule held by a second capsule may be prepared from microfluidic double emulsion droplets which are generated in a microfluidic platform, such as shown in FIG. 2. The phase that it intended to be the innermost part of the droplet, and therefore the innermost part of the capsule, is provided as a first fluid stream from an inlet, such as Inlet 3 in FIG. 2. This first fluid stream is permitted to flow into an immiscible second phase at a T-junction or a X-junction. The second phase is intended to be the middle part of the droplet. The second phase is provided from an inlet, such as Inlet 2. The introduction of the first fluid flow into the flow of the second phase results in the formation of droplets of the first phase (first droplets) in the second phase. The flow of the second phase, holding droplets of the first phase, is permitted to flow into an immiscible third phase a further T-junction or X-junction. The third phase is provided from an inlet, such as Inlet 1. The introduction of the second fluid flow into the flow of the third phase results in the formation of droplets of the second phase (second droplets) in the third phase. In this way, a droplet of a second phase holding a droplet of a first phase may be prepared in one fluid flow procedure.

Suitable hosts and building blocks with suitable guest functionality are provided in the phases, as appropriate. The supramolecular network making up a capsule shell is formed at each droplet interface. Thus the shell of the first capsule is formed at the interface of the first droplet with the second phase. The shell of the first capsule is formed at the interface of the second droplet with the third phase.

It is not necessary for the capsule shells to form immediately after the generation of a droplet, and the shells may form at a later time after collection of the double emulsion droplets, for example after drying of the double emulsion droplets.

As previously discussed by Zhang et al., fluidic preparation methods of this type generate monodisperse droplets, and therefore monodisperse capsules. It follows that the nested capsules produced by such methods will also be substantially monodisperse. Thus, in the basic arrangement of the nested capsule, the first and the second capsules will be substantially monodisperse.

The dimensions of the first and second capsules can be easily manipulated by varying the dimension of the original double emulsion droplets, for example by altering the respective flow rates of the three phases within the microfluidic channels.

Figure 3:
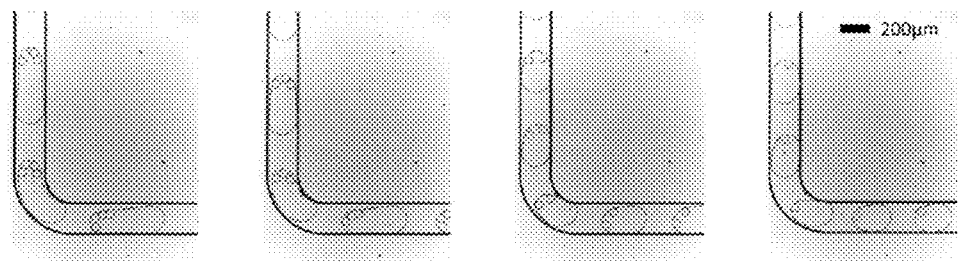
FIG. 3 shows images of double emulsion droplets in a fluid flow channel. Double emulsion droplets may be prepared where the second droplet holds four, three, two or one first droplets. From such droplets a nested capsule may be prepared where the second capsule holds four, three, two or one first capsules.

Similarly the population of first capsule within the second capsule can be controlled through the ratio of the flow rates of the three phases. Such changes allow the preparation of second droplets holding a desired number of first droplets. This is shown in FIG. 3, where the population of the first droplets in a second droplet can be increased from one to four independently from the second droplet dimension. Shell material may be formed at each droplet interface, as previously discussed, thereby to provide nested capsules where the second capsule holds a plurality of first capsules.

It is typical in the art to fabricate oil-water-oil double emulsion droplets. However, any combination of immiscible phases may be used. Suitable combinations include water-oil-water, water-water-oil and solvent-water-oil.

It is known from the art that aqueous solutions may be prepared that are immiscible with one another. For example, all aqueous compartmentalisation may be achieved using appropriate additives added to the respective aqueous phases, for example dextran in one aqueous phase and gelatin in another aqueous phase will provide two aqueous solutions that are immiscible (see Ziemecaks et al. Proceedings of the 3$^{rd}$ European Conference on Microfluidics—Miorofluidics 2012).

The general methodology above may be extended to the preparation of higher emulsion multiplicities (e.g. triple-emulsions) through the incorporation of additional junctions within the device. This allows for the preparation of a nested capsule having a third capsule which holds one or more second capsules, wherein each second capsules holds one or more first capsules. A triple emulsion is shown in FIG. 4(b).

The building blocks that are incorporated into the shell network are provided in the fluid flows, such as the first and second fluid flows. The building blocks typically diffuse to the droplet interface i.e. the interface between each phase of the emulsion. This may be readily seen using a labelled building block.

For example, an oil-water-oil double emulsion droplet was formed using the techniques described above, with a rhodamine-tagged polymer provided in the second aqueous phase. Fluorescence imaging of the double emulsion droplet showed the polymer to be located at the interfaces of the droplets. The rhodamine-tagged polymer is a polymer of structure PVA-Rhod-MV:

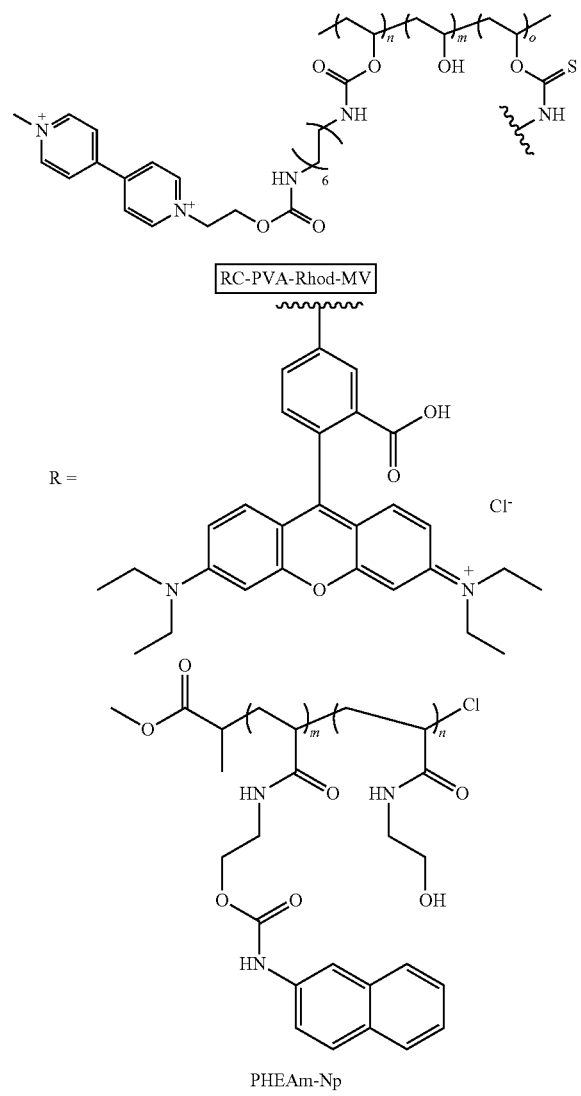

Nested microcapsules were prepared from double emulsion droplets using FC-40 oil (Fluorinert FC-40 perfluorinated oil) and water as the immiscible phases. The oil was used as the first and third phases, and water as the second phase.

The oil phase contained 2 wt % of the surfactant XL171 and 0.2 wt % of the commercial carboxylic acid surfactant Krytox 157 FS L.

The aqueous phase included equimolar quantities (60 μM, calculated for functional guest on polymer) of cucurbit[8]uril and the polymers PVA-Rhod-MV and PHEAm-Np (shown above). PVA-Rhod-MV is a rhodamine-tagged methyl viologen functionalised polyvinylalcohol and PHEAm-Np is a naphthol functionalised poly(2-hydroxyethyl acrylamide). The methyl viologen and naphthol guests are capable of forming a ternary complex with a CB[8] host, leading to the generation of a supramolecular cross-linked network. The rhodamine fluorescent tag is used to visualise the location of the polymer whilst in the droplet phase which allows the interfacial properties of the polymers to be predicted.

Figure 4:
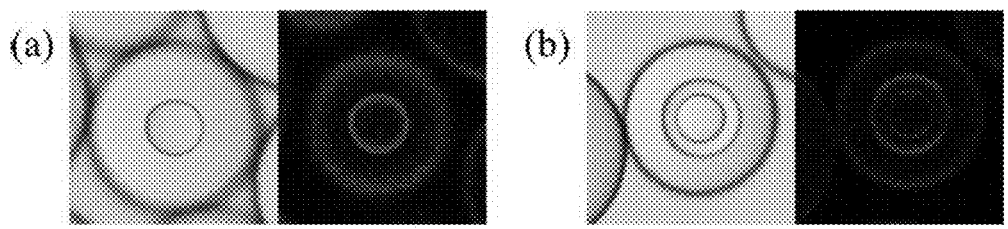
FIG. 4 shows confocal (left in each pair) and fluorescence (right in each pair) micrographs of (a) an oil-water-oil double emulsion microdroplet and (b) a water-oil-water-oil microdroplet triple emulsion (oil innermost phase). The source of the fluorescence is a rhodamine-tagged polymer which is localised at the interfaces of the droplet, where it is available to from a supramolecular network. The outer droplet has a diameter of around 100 µm.

In line with the general method discussed above, double emulsion droplets were generated by flowing the alternate oil and water phases through a series of flow focuses within a microfluidic device, generating the innermost droplet first; before collection within a second microfluidic chip containing a large 'reservoir' region for microscopic study. Triple emulsion droplets were formed by incorporation of a further inlet into the flow system. Such droplets are shown in FIG. 4, with images showing the location of the fluorescent polymer at the droplet interfaces.

Flow rates increase with addition of each sequential phase to compensate for the larger volume of fluid needed for each droplet and surface area of the final capsule, e.g. for the double emulsion flow rates for the three phases of 40/175/500 μLh$^{-1}$ is representative, with variations in the ratio of flow rates altering the number of first (inner) droplets within the second (outer) droplet. Changes in absolute flow rate used to alter the volume of a droplet, and therefore the volume of a capsule. The present inventors have prepared double emulsion droplets where the first droplet has a diameter of about 50 μm and the second droplet has a diameter of about 100 μm. The inventors have also prepared droplets having diameters considerably larger than this.

The size of the capsules in the resulting nested capsule is dictated by the size of the droplets from which each capsule is formed. Given that the capsule shell forms at the interface of a droplet, the size of the capsule will generally match that of the droplet. It will be appreciated that a capsule may be smaller than the droplet from which it was formed, for example as a consequence of the optional drying steps that are performed during and after the capsule preparation.

In an alternative preparation, the aqueous phase described above included 90 μM cucurbit[8]uril and the polymers PVA-Rhod-MV and PHEAm-Np (calculated with respect to the functional guest on polymer). The aqueous phase also included 2.5 μM of 500 kDa FITC-dextrin as a cargo for encapsulation. The FTIC is a fluorescein tag for detection of the cargo.

Figure 5:
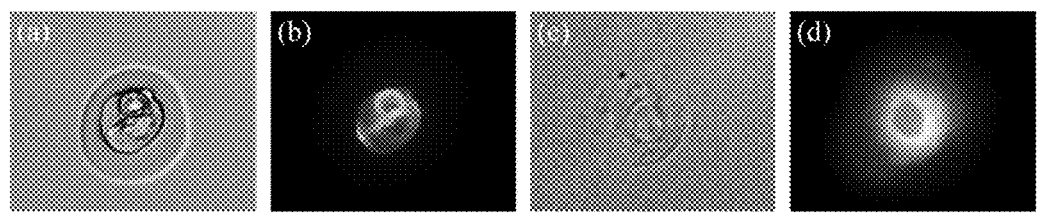
FIG. 5 shows micrographs of a dried nested capsule according to one embodiment of the invention, where a second capsule holds a first capsule and a fluorescently-labelled dextran encapsulant, and (a) is a micrograph of the nested capsule; (b) is the fluorescent micrograph of the nested capsule after drying, showing the encapsulant to be located in the second capsule; (c) is a micrograph of the nested capsule 10 minutes after rehydration, showing capsule swelling; and (d) is the fluorescent micrograph of the nested capsule after rehydration showing the encapsulant to be retained in the second capsule.

Double emulsion droplets were formed as described above, and collected on a perfluorinated-glass slide. The droplets were allowed to dry to form collapsed double emulsion microcapsules i.e. a nested capsule. These nested capsules are shown in FIG. 5 as described below. The nested capsules were then subsequently rehydrated with de-ionised water for 10 minutes. The double emulsion droplets were generated at flow rates of 35/240/250 μLh$^{-1}$. The first (inner) droplet had a diameter of around 50 μm and the second (outer) droplet had a diameter of around 100 μm. After dehydration the second (outer capsule) had a diameter in the range 20-30 μm, which increased to 40-60 μm upon rehydration.

FIG. 5 shows a micrograph (a) of the dried nested capsule, and a fluorescent micrograph (b) showing the location of the fluorescently tagged dextrin cargo within the second capsule. After rehydrating the capsule in water for 10 minutes the capsule was observed to swell, as shown in micrograph (c). The fluorescent cargo was found to remain within the outer capsule, as shown fluorescent micrograph (d), thus allowing the first (inner) capsule to be visualised.

The two distinct environments present within the nested capsule morphology allows for the isolated storage of multiple, chemically diverse or incompatible cargoes. These encapsulated cargoes are physically separated from each other and the external environment by the capsule wall, allowing for application in chemical or biological storage both in terms of improving the life-span of the encapsulant (protecting the encapsulant from the environment/other encapsulants) and in improving the handling properties of the encapsulant (protecting the environment from the encapsulant).

Figure 6:
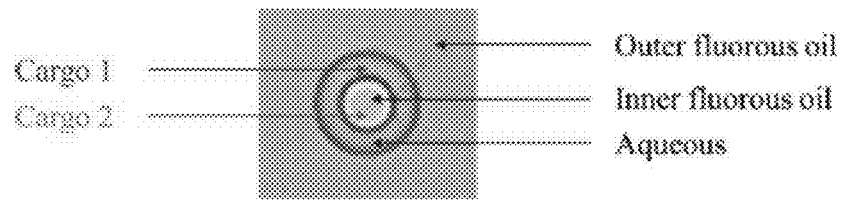
FIG. 6 is a schematic of an oil-water-oil double emulsion droplet for use in the preparation of a nested capsule. The double emulsion droplet holds cargoes (encapsulants) in the second (outer) droplet and the first (inner droplet).

FIG. 6 is an image of an exemplary oil-water-oil double emulsion microdroplet, showing the location of the compartmentalised encapsulants within each phase. The generation of a capsule from this droplet allows for chemically diverse or incompatible cargoes to be incorporated within each layer of the capsule independently of the other layers.

One approach to the preparation of orthogonal nested capsules consists of introducing a mixture of polymers to the second phase of a double emulsion microdroplet (the middle phase). By selecting the surfactants present in the first phase (inner phase) and the third phase (outer phase), the interfaces between the first and second phases, and the second and third phases can be made chemically distinct. Polymers may be selected for use in the second phase having a preference for one of the two interfaces. Thus, one polymer may selectively locate to the interface between the first and second phases, and another polymer may selectively locate to the interface between the second and third phases. The shells that are formed at each of these interfaces will therefore be different.

Figure 7:
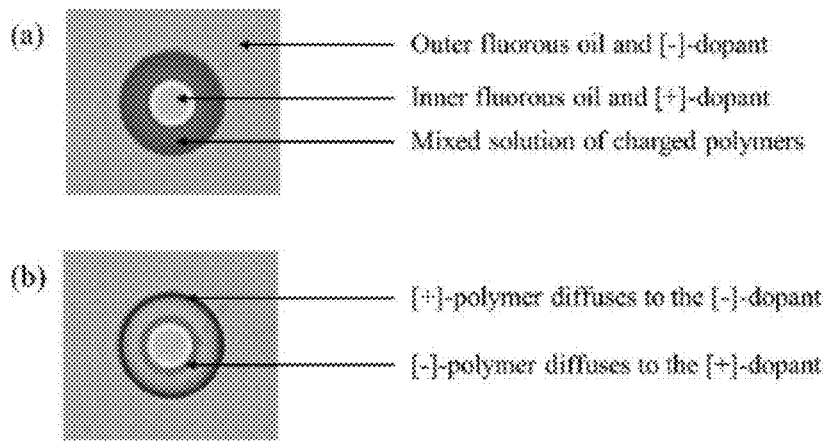
FIG. 7 is a schematic of an oil-water-oil double emulsion droplet for use in the preparation of a nested capsule, where the second (outer) droplet holds a mixture of negatively- and positively-charged polymers, the first (inner) droplet holds a positively-charged surfactant and the continuous phase holds a negatively-charged surfactant.

This is illustrated in FIG. 7, whereby oppositely charged dopants are introduced to the first (inner) and third (outer) oil phases of an oil-water-oil double emulsion microdroplet. The aqueous phase (the second or middle phase) contains a mixture of charged building blocks, such as charged polymers. The dopants within the oil phases will diffuse to the droplet interfaces, resulting in a localised surface charge that will attract oppositely charged building blocks in the aqueous phase. Building blocks having the same charge as the dopant will be destabilised at the interface, and will not generally be located there. With the appropriate combinations of building blocks and host, the discriminatory effect allows for the formation of disparate capsules within a nested capsule.

The discriminatory effect has been demonstrated experimentally through the use of carboxylic acid and amine-terminated hexfluoropropylene oxide oils (derived from DuPont Krytox 157 FS L) that within the oil phase form negatively (carboxylate) and positively charged (ammonium) droplet interfaces respectively.

This selective localisation of polymers to a droplet interface is illustrated was studied using a simple single emulsion droplet, such as those droplets described by Zhang et al. (*Science* 2012, 335, 690) in the preparation of capsules having a shell of material that is a cucurbituril cross-linked network.

Thus a range of aqueous droplets in a fluorous oil continuous phase was prepared. The interaction between differently charges surfactants in the oil and differently charged polymers in the aqueous phase was investigated.

The single emulsion droplets were prepared with a diameter of about 50 μm. The polymers in the aqueous phase were present are at 30 μM with respect to the concentration of the guest molecules (e.g. methyl viologen, $MV^{2+}$, or naphthol, Np).

The positive polymer was PVA-Rhod-MV (as shown above). The positive charge is found on the rhodamine group and the methyl viologen and $MV^{2+}$ guest. The negative polymer was PHEAm-FITC-Azo. The negative charge is found on the fluorescein (FITC) moiety. The PHEAm-FITC-Azo polymer is shown below. The polymer RC-PHEAm-AmAm-FITC-Azo, which is related to PHEAm-FITC-Azo, is shown below. RC-PHEAm-AmAm-FITC-Azo may be used in place of PHEAm-FITC-Azo. The AmAm group provides additional solubility.

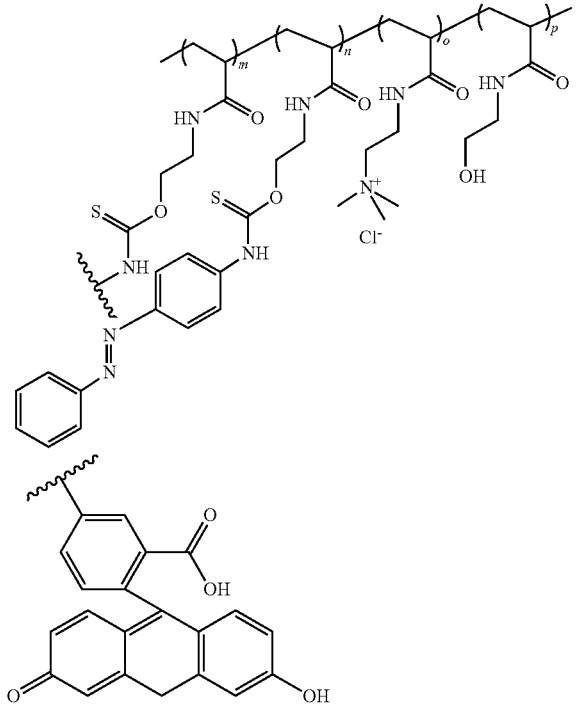

The polymer RC-PHEAm-AmAm-FITC-Azo has 10% AmAm, 10% Azo, 1% FITC, with the remainder HEAm.

The negative dopant for the oil phase was Krytox 157 FS L, which generates carboxylate (−) functionality in aqueous solution. The positive dopant for the oil phase was the amine terminated derivative of Krytox 157 FS L, which was prepared from Krytox 157 FS L, and generates ammonium (+) functionality in aqueous solution.

For both charged polymers, no preference for the interface is observed when just a neutral surfactant is used, however when a small amount of charged dopant is incorporated into this interface a clear trend is observed, with positively charged polymers attracted to negatively charged interfaces and vice-versa. When a mixed polymer system is used, the polymers respond consistently with the above trend, with no evidence for interaction between the polymers occurring due to charge minimisation or other factors.

Figure 8:
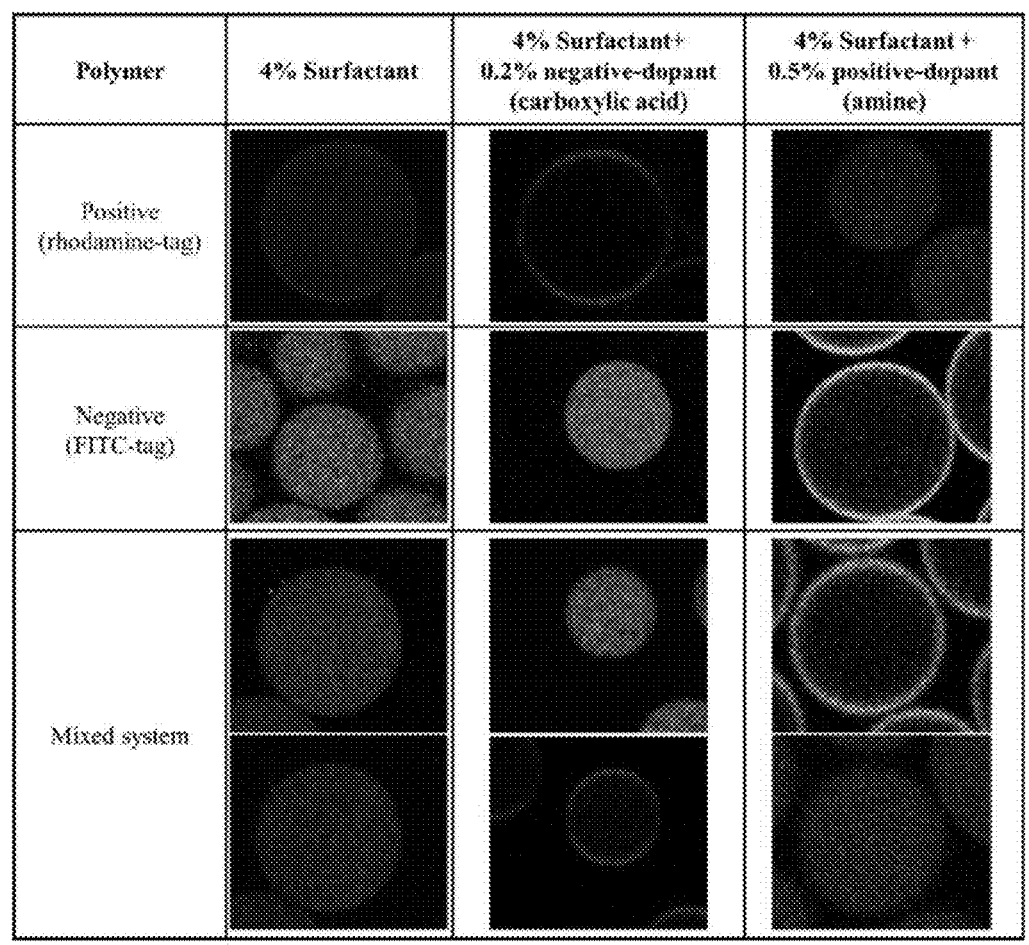
FIG. 8 is a collection of micrographs showing the distribution of a rhodamine-tagged positively charged polymer (PVA-Rhod-MV), a FITC-tagged negatively-charged (PHEAm-FITC-Azo) polymer, and a mixture of these polymers in a single emulsion droplet with 0.5 wt % of a positive dopant present in the continuous phase, 0.2 wt % of a negative dopant present in the continuous phase, and without a dopant in the continuous phase. The continuous phase is provided with 4 wt % surfactant in each case.

The polymers were attracted to oppositely charged droplet interfaces, and a mixed system experiment shows that this is favourable even when and oppositely charged polymer is also present. Confocal fluorescent images were collected sequentially and are not shown overlaid for the two dyes. For a neutral system neither polymer was stabilised (or destabilised) at the droplet interface. The micrograph images are shown in FIG. 8.

If cucurbit[8]uril is introduced into this mixed system, the polymers are suitably functionalised as to allow supramolecular complexation to occur. If third polymer that can act as a competitor is added to the system, it is found that the preference to form a complex with a polymer with the same interfacial properties is favoured irrespective of the charges on the polymer themselves. In the mixed system it was found that the preference to form a cross-linked hydrogel is greater than that of the additional stability introduced through diffusing to a charged interface, and in the surfactant scenarios exemplified in FIG. 8, polymer microspheres were formed rather than capsules.

A series of experiments were run, preparing aqueous droplets comprising A, B and B' in a fluorous oil continuous phase, with a cucurbituril host provided in certain experiments. The positively charged polymer A, in this case PVA-Rhod-MV, can cross-link through a supramolecular complex to either a negatively charged polymer B, PHEAm-FITC-Azo, or the weakly positively charged polymer B'. PVA-Rhod-Stil, which is effectively identical to PVA-Rhod-MV but with the $MV^{2+}$ guest replaced with a neutral stilbene moiety that can compete with the Azo guest of PHEAm-FITC-Azo to form a ternary complex with MV in the host CB[8]. The weakly positive PVA-Rhod-Stil is stabilised at the interface by the surfactant alone (it is believed that XL171 is very weakly negatively charged and this is sufficient to stabilise the interface here).

When a neutral droplet interface is present, polymers A and B will remain in the bulk, while polymer B' will diffuse to the interface. In the presence of CB[8], a polymer microsphere will form between polymers A and B. In contrast, if a negatively charged interface is generated (e.g. through the use of a carboxylate surfactant), polymers A and B' will be stabilised at the droplet interface with polymer B remaining in the droplet interior. In this second case, a microcapsule will form between A and B' with B effectively becoming a cargo (encapsulant) in the resulting capsule.

This trend is demonstrated in FIG. 9 both by the location of the fluorescently tagged polymers in the presence of CB[8], and by the contrasting appearances of the resultant supramolecular products, before and after rehydration Specifically, the use of an appropriate capsule-forming surfactant leads to larger, wrinkled product: indicative of a collapsed capsule, compared to the smooth, small microsphere-like particles formed with the surfactant alone. Upon rehydration with deionised water, the microcapsules swell to a much greater extent than microspheres, with the fluorescent micrographs indicating the presence of an outer capsule skin.

This experiments show that the MV-containing polymer, in the presence of CB[8], will form a ternary complex with whichever polymer is exhibiting the same interfacial properties, leading to either capsules or particles, depending on the inclusion of a surfactant. Thus, the geometry can be controlled by the choice of surfactant in the oil phase using simple considerations of charge, while the presence of a third polymer is shown to not interfere with complex formation.

In a mixed aqueous system with a negative surfactant present in the continuous oil phase (-ve interface), PVA-Rhod-MV and PVA-Rhod-Stil polymers will move to the interface where they can form a supramolecular network with an appropriate host. The formation of this network provides a shell which effectively contains the PHEAm-FITC-Azo polymer, which does not participate in the network. Without any droplet charging, the single polymer system predicts that PVA-Rhod-MV and PHEAm-FITC-Azo will form a solid microsphere. Microsphere and capsule morphologies are illustrated by the differences in appearance of the dried state, as noted above, and the differences in swelling upon rehydration.

Figure 10:
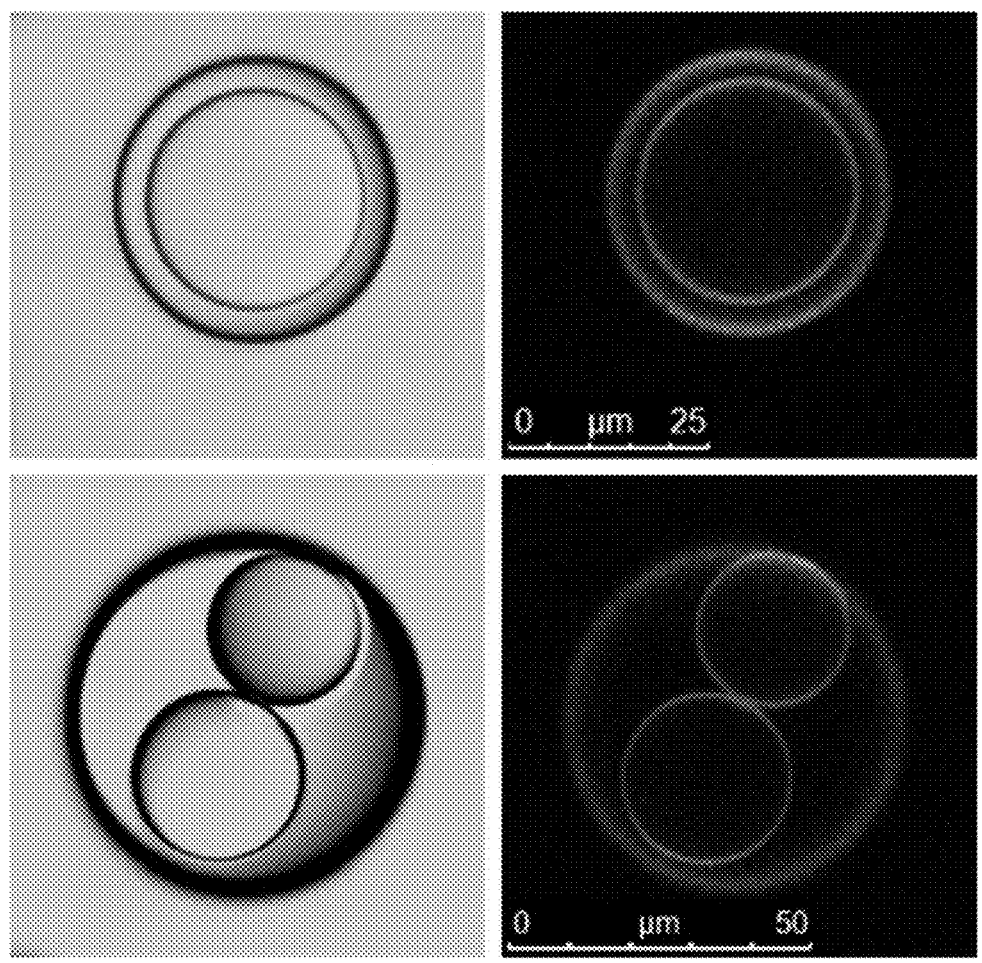
FIG. 10 is a series of bright-light and fluorescence micrographs of oil-water-oil double emulsion microdroplets containing a mixed polymer middle aqueous phase. Positively charged polymer (rhodamine-tagged) diffuses to the interface of the inner droplet due to the presence of the negatively charged carboxylate-terminated dopant in the inner oil phase (first droplet), while negatively charged polymer (fluorescene-tagged) diffuses to the interface of the outer droplet (second droplet) due to the presence of the positively charged amine-terminated dopant in the outer oil phase. The top images are of a second droplet holding a single first droplet, and the bottom images are of a second droplet holding two first droplets.

Within the double emulsion regime, the ability to control the interfacial properties of the polymers allows for the formation of disparate polymer capsules from a mixed aqueous phase. This is shown in FIG. 10, where double emulsion microdroplets comprising inner and outer droplets of different composition were fabricated from a single aqueous mixture, through use of oppositely charged droplet interfaces. Further, it is shown that this methodology will scale to a wider range of droplet geometries beyond the simple "1 in 1" double emulsion microdroplet motif.

FIG. 10 includes bright-light and fluorescence micrographs of double emulsion (oil-water-oil) microdroplets containing a mixed polymer middle aqueous phase. The aqueous system which provides the second droplet contained PVA-Rhod-MV and PHEAm-FITC-Azo. A host was not added to the aqueous phase at this stage, as the experiment was designed to study the distribution of the polymers to the droplet interfaces. The first (inner) droplet contained 4 wt % XL171 and 0.2 wt % Krytox in FC-40. This provided a negative interface and attracted positively charged PVA-Rhod-MV polymer. The outer (continuous) phase contained 4 wt % XL171 and 0.5 wt % amine-terminated Krytox derivative in FC-40. This provided a (positive interface and attracted positively charged PHEAm-FITC-Azo polymer. Double emulsion droplets having one or two first (inner) droplets were prepared.

FIG. 10 shows bright-light and fluorescence micrographs of double emulsion microdroplets containing the mixed polymer middle aqueous phase. Positively charged polymer (rhodamine-tagged) diffuses to the interface of the inner droplet due to the presence of the negatively charged carboxylate-terminated dopant in the inner oil phase, while negatively charged polymer (fluorescene-tagged) diffuses to the interface of the outer droplet due to the presence of the positively charged amine-terminated dopant in the outer oil phase.

Polymer Compositions

The compositions of the polymers described above, are set out in the Table below.

| Polymer | Polymer Backbone | Guest | $M_w$ | No. of monomer units per polymer | Percentage monomer in polymer |
|---|---|---|---|---|---|
| PVA-Rhod-MV | polyvinylalcohol | MV | 109,000 | MV = 100 | MV = 10% |
|  |  |  |  | Rhod = 10 | Rhod = 1% |
| PVA-Rhod-Stil | polyvinylalcohol | Stilbene | 72,730 | Stil = 100 | Stil = 10% |
|  |  |  |  | Rhod = 10 | Rhod = 1% |
| PHEAm-FITC-Azo | poly(N-cyclohexylacrylamide) | Azo | 143,254 | Azo = 74 | Azo = 7% |
|  |  |  |  | FITC = 10 | FTIC = 1% |
| PHEAm-Np | poly(N-cyclohexylacrylamide) | Np | 24,600 | Np = 200 | Np = 20% |

Additional Preparative Work on Nested Capsules

The movement of a polymer to an attractive interface was studied using real-time confocal microscopy, and is shown in FIG. 23. An aqueous fluid flow containing a positively-charged polymer (rhodamine-tagged, red) was dispersed as droplets into an oil continuous phase containing a negatively-charged surfactant. It was observed that the diffusion of polymer to the interface was nearly instantaneous with clearly defined rings observed shortly after droplet formation. By the time the droplets had reached the exit of the chip (<1 s) the polymer was exclusively located at the droplet interface.

The aqueous droplet contained exclusively 60 uM RC-PVa-Rhod-MV (no CB[8]) and the continuous oil phase was FC-40 perfluorinated oil containing 4% of the neutral surfactant XL171 and 0.2% of the carboxylic acid terminated Krytox to introduce negative charge via the carboxylate.

This rapid diffusion to the interface has been shown to be reversible; replacing the surfactant surrounding a preformed droplet with that of either a neutral, or oppositely-charged surfactant has been shown to disperse the polymer to the droplet bulk. Further, in a droplet containing orthogonally charged polymers this can be used to dynamically switch which polymer is present at the interface or in the bulk.

Additional Formation of Nested Capsules

FIG. 24 is a series of micrographs showing the formation of nested microdroplets in an (a) oil-water-oil and (b) chloroform-water-oil system. The micrographs show the subsequent formation of a nested capsule from the nested microdroplets upon complexation of a CB[8] host with polymeric molecules having suitable guest functionality (RC-PVA-Rhod-MV and RC-PVA-Rhod-Stil).

The oil used was FC40 perfluorinated oil.

In the oil-water-oil system (a), three oil droplets [containing Krytox (-ve) dopant via carboxylate and XL171 surfactant] were encapsulated in an aqueous droplet containing CB[8] and copolymers RC-PVA-Rhod-MV and RC-PVA-Rhod-Stil in an oil continuous phase (the oil phase containing Krytox and XL171) (see image 1). Upon drying, gradual evaporation of the aqueous phase resulted in the formation of a capsule skin form at the outer interface—however evaporation of the inner oil droplets is minimal (see image 2). Once the majority of the water has evaporated, the inner oil phase is able to evaporate/diffuse through the aqueous droplet allowing capsule formation at the inner interface giving rise to a capsules-in-capsule structure that resembles the original droplet architecture (see image 3).

In the chloroform-water-oil system (b), chloroform is used in place of the inner oil phase of the oil-water-oil system (a). Upon drying, the chloroform gradual evaporates through the aqueous phase (as expected from this relatively volatile solvent). This results in the inner capsule forming first (left image), proving that capsule formation is indeed occurring at the inner interface. Over time the aqueous phase evaporates giving rise to a capsule skin at the outer interface (middle then right images).

The surfactants and polymers were used as described in the Nested Capsules section above.

Orthogonal Capsules

Described below are several trigger-release mechanisms for use with suitable supramolecular capsules described of the present case. By way of exemplification, capsules based on CB[8] ternary complexes are described.

Reduction-Oxidation Triggered Release

The first release mechanism is based on reduction-oxidation (redox) chemistry. This is exemplified for the release of the methyl viologen cationic radical from a CB[8] ternary complex. As previously described (Jeon et al. *Chem. Commun.* 2002, 38, 1828), methyl viologen ($MV^{2+}$) is known to readily undergo one electron reduction of the moiety to yield a radical cationic species ($MV^{+\bullet}$). This exists as an equilibrium mixture of monomeric and dimeric forms in aqueous solution. In the presence of CB[8], however, the equilibrium is heavily biased towards the dimeric species and the formation of a stable 2:1 [$(MV^{+\bullet})_2 \subset CB[8]$] inclusion complex. This shown in FIG. 31, in the formation of a 2:1 [$(MV^{+\bullet})_2 \subset CB[8]$] complex consisting of CB[8] and two molecules of methyl viologen cationic radical ($MV^{+\bullet}$).

The redox-active viologen moiety is particularly useful as an electrochemical trigger for a CB[8]-based supramolecular system. While the association constant for the second guest (naphthol) binding in the presence of the [$(MV^{2+}) \subset CB[8]$] complex is in the range $8 \times 10^4$ $M^{-1}$ to $2 \times 10^5$ $M^{-1}$ (Appel et al. *J. Am. Chem. Soc.*, 2010, 132, 14251), the dimerization constant of $MV^{+\bullet}$ in the presence of equimolar CB[8] is estimated to be $2 \times 10^7$ $M^{-1}$, which is about 105 times larger than that of $MV^{+\bullet}$ alone and about 100 times larger than that of naphthol. Such a large difference results in the preferential formation of the 2:1 [$(MV^{+\bullet})_2 \subset CB[8]$] complex upon the addition of a reducing agent at the expense of the hetero-guest ternary complex, as shown in FIG. 32, which illustrates the preferential formation of the 2:1 [$(MV^{+\bullet})_2 \subset CB[8]$] inclusion complex over the [$(MV^{2+})(naphthol) \subset CB[8]$] ternary complex in the presence of a reducing agent:

This property has been extensively exploited in CB[n]-based chemistry, especially in probing the successful functionalization of AuNP surface using sodium dithionite ($Na_2S_2O_4$).

The application of this stimulus-responsive mechanism was investigated in microcapsules.

To monitor the release of a cargo in situ over time, several requirements for the experimental setup need to be satisfied, including an oxygen-free environment for the single electron reduction to occur, as well as a sealed chamber to prevent dehydration of the sample during long-term monitoring. For these purposes, a simple yet effective experimental chamber was constructed using flasks designed for culturing mammalian cells. These cell culture flasks are optically transparent and equipped with filter caps allowing for easy replacement of internal gas.

A glass slide containing dried capsules was placed in the cell culture flask on the microscope stage. An oxygen-free environment was then created by continuously delivering nitrogen gas into the chamber, before the capsules were rehydrated by depositing a drop of $Na_2S_2O_4$ solution or water using a needle through the filter cap. The continuous flow of nitrogen gas was likely to cause accelerated dehydration of the sample and hence the needle was removed and the cap of the flask was sealed for long-term storage.

Figure 11:
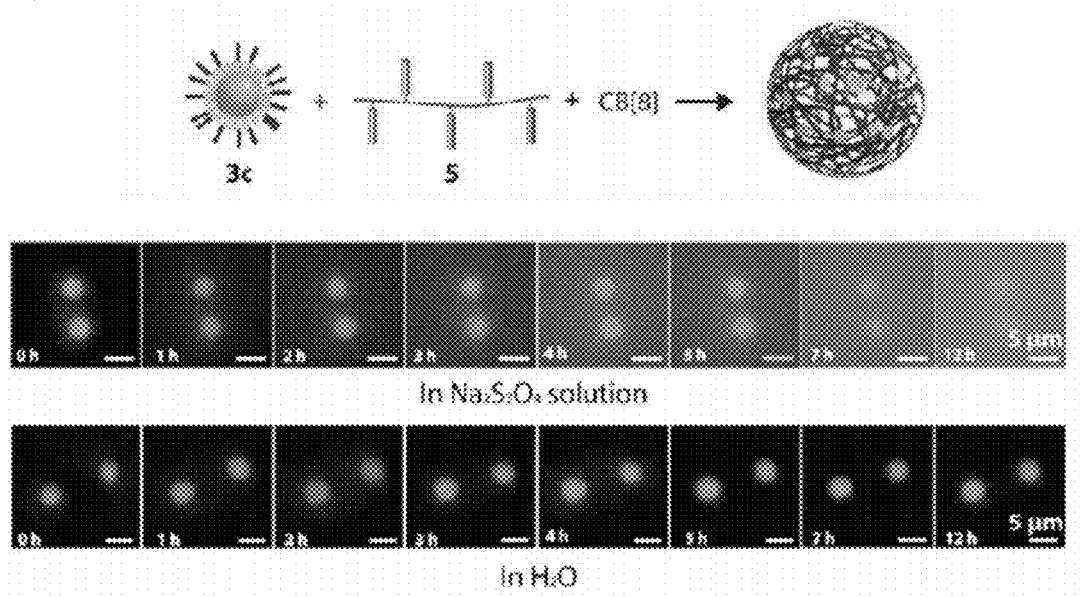
FIG. 11 is (top) a schematic of a microcapsule, where the shell of material is obtained from a composition comprising $MV^{2+}$-AuNP 3c, copolymer 5 and CB[8] ($[MV^{2+}]$=[naphthol]=[CB[8]]=3×10$^{-5}$ M); (middle) the fluorescence images of an encapsulated 500 kDa FITC-dextran in the microcapsules in an aqueous solution of $Na_2S_2O_4$ over 12 hours; and (bottom) the fluorescence images of the encapsulated 500 kDa FITC-dextran in the microcapsules in water over 12 hours.

The disruption of AuNP-embedded microcapsules was studied initially (FIG. 11). In the presence of the oxygen-free solution of $Na_2S_2O_4$ (1 mM), a controlled dissipation of the FITC fluorescence was observed over time (FIG. 11). After only one hour, blurring of the fluorescence outline was observed, while the entire background appeared fluorescent through slow diffusion after twelve hours. When an inert atmosphere was not maintained or in the absence of $Na_2S_2O_4$ (FIG. 11) the microcapsules failed to release the encapsulated 500 kDa FITC-dextran, as indicated by the localized FITC fluorescence over time. Here a large molecular-weight cargo such as 500 kDa FITC-dextran is too big to its content until a chemical trigger is applied.

The relatively slow but sustained release over twelve hours provides evidence for the strength of the capsule shell on account of the multivalent interactions between AuNPs and copolymers.

This redox stimulus was also studied for the polymeric counterpart of the AuNP-embedded microcapsules. The polymeric microcapsules were prepared from copolymers 5 and 14, cross-linked by CB[8] (FIG. 12(a)). Microdroplets containing an aqueous mixture of these materials and an FITC-labelled cargo were collected and dried on glass slides and place in a nitrogen chamber as described previously. Prior to being exposed to $Na_2S_2O_4$, it was noted that the microcapsules retained the FITC fluorescence.

Figure 12:
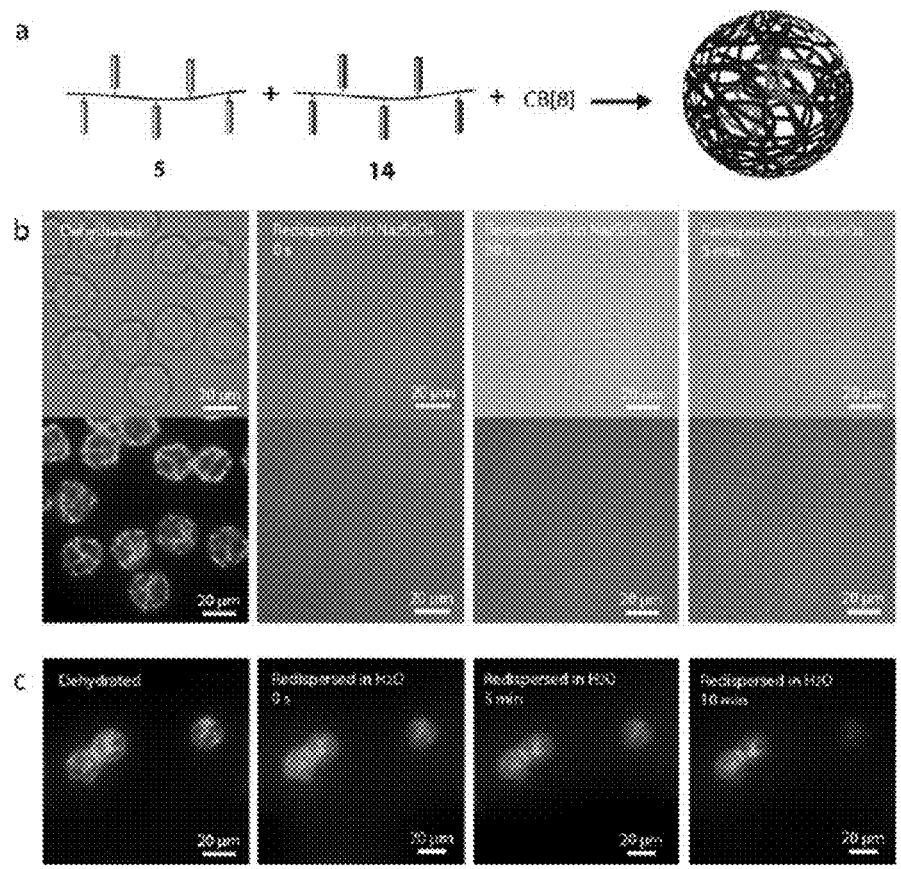
FIG. 12 is (a) a schematic of a microcapsule, where the shell of material is obtained from a composition comprising copolymers 5, 14 and CB[8] ($[MV^{2+}]$=[naphthol]= [CB[8]]=2.5×10$^{-5}$ M), containing 500 kDa FITC-dextran (1×10$^{-6}$ M); (b) the bright-field and fluorescence images of an encapsulated 500 kDa FITC-dextran in the microcapsules in an aqueous solution of $Na_2S_2O_4$ over 5 minutes; and (c) the fluorescence images of the encapsulated 500 kDa FITC-dextran in the microcapsules in water over 5 minutes.

Upon contact with an oxygen-free solution of $Na_2S_2O_4$, widespread diffusion of the fluorescence out of the microcapsule was observed instantaneously (FIG. 12(b)). The ness, and appropriate size make it a suitable guest for a number of host molecules (Xiao et al *J. Phys. Chem B* 2011, 115, 13796; Wu *Chem. Eur. J.* 2009, 15, 11675). Upon irradiation with UV light, it also undergoes photoisomerization from the trans-isomer to the cis-isomer, which is in general too bulky to remain in the cavity of the host molecule and hence dissociates from the supramolecular complex. The cis-azobenzene also isomerizes back to its trans-species upon either light or thermal stimulus without any by-products or degradation unlike its structural analogue stilbene which is known to undergo competing reactions under irradiation (Waldeck *Chem. Rev.* 1991, 91, 415) resulting in the loss of the cis-isomer after multiple cycles of photoisomerization.

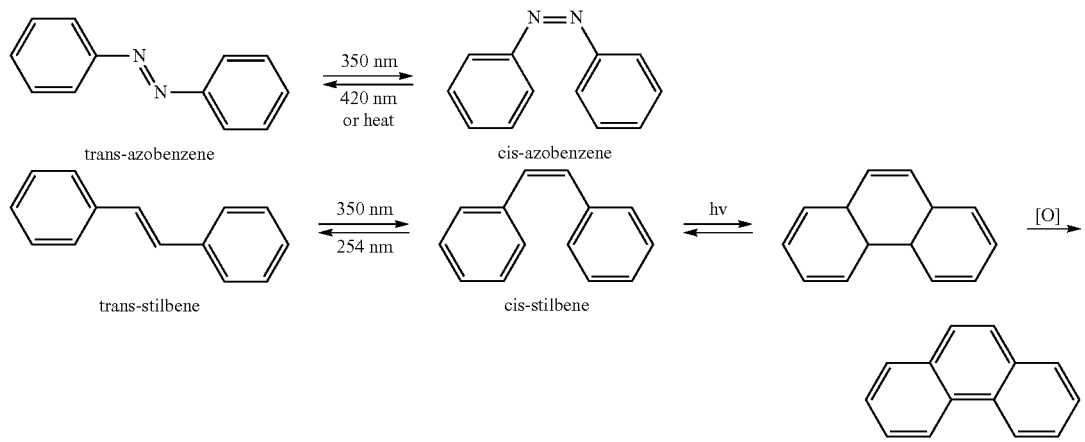

difference in the time-scale of cargo release in AuNP-embedded and polymeric microcapsules was not entirely understood. However this rapid effect is consistent with the observations of $MV^{2+}$-containing copolymers and small molecules complexation systems.

The intensity of the fluorescence increased slightly over the next 5 min, while the microcapsules appeared fragmented and visible in the corresponding bright field images. When $Na_2S_2O_4$ was absent, the rehydrated microcapsules appeared intact over time with minimal leakage of the FITC-labelled cargo (FIG. 12(c)). Therefore, the one-electron reduction of $MV^{2+}$ to its radical cation can also be used to trigger the self-aggregation of the $MV^{2+}$-containing copolymers at the expense of degrading polymeric microcapsules. This result demonstrates the versatility of the system, where the building blocks of the microcapsules can be changed according to the specific application while the ability to be triggered to release using redox stimuli is maintained where there is a suitable redox active guest present in a complex.

Light-Triggered Release

One of the few examples of photochemical switches used in a non-covalent interaction in a capsule shell is reported by Xiao et al (*J. Phys. Chem B* 2011, 115, 13796). The shell was composed of a mixture of two copolymers interlinked via a cyclodextrin-azobenzene inclusion complex, which, upon irradiation with UV light, dissociates to degrade the capsule shell and release the encapsulated content.

Azobenzene is one of the light triggers commonly used in supramolecular chemistry. Its hydrophobicity, electron-rich- As a common supramolecular host, CB[n]s have also been applied in conjunction with these light-sensitive functionalities, CB[7] has been observed to promote the spontaneous thermal trans-to-cis isomerisation of diamino-azobenzene derivatives, presumably as a result of stabilization of the cis-isomer through complexation with CB[7] (due to size complimentary and ion-dipole interaction between the protonated amino groups and the portal oxygen atoms of CB[7]) (Wu *Chem. Eur. J.* 2009, 15, 11675).

The CB[8] analogue with a bigger internal cavity is able to accommodate two molecules of stilbene and promotes the [2+2] photoreaction of its trans-species with a large acceleration in rate and high stereoselectivity (Jon et al. *Chemical Communications* 2001). Given the structural similarity between azobenzene and stilbene with naphthol, it has been postulated that they can be used as appropriate second guests in the 1:1:1 heteroguest complexation with $MV^{2+}$ and CB[8]. Initial studies on the use of trans-stilbene and trans-azobenzene as electron-rich guests has been carried out and the results suggest that it can serve as a replacement for naphthol in forming a stable 1:1:1 ternary complex with $MV^{2+}$ moieties in CB[8] (Ka=$10^5$ M) (FIG. 13(a)).

Figure 13:
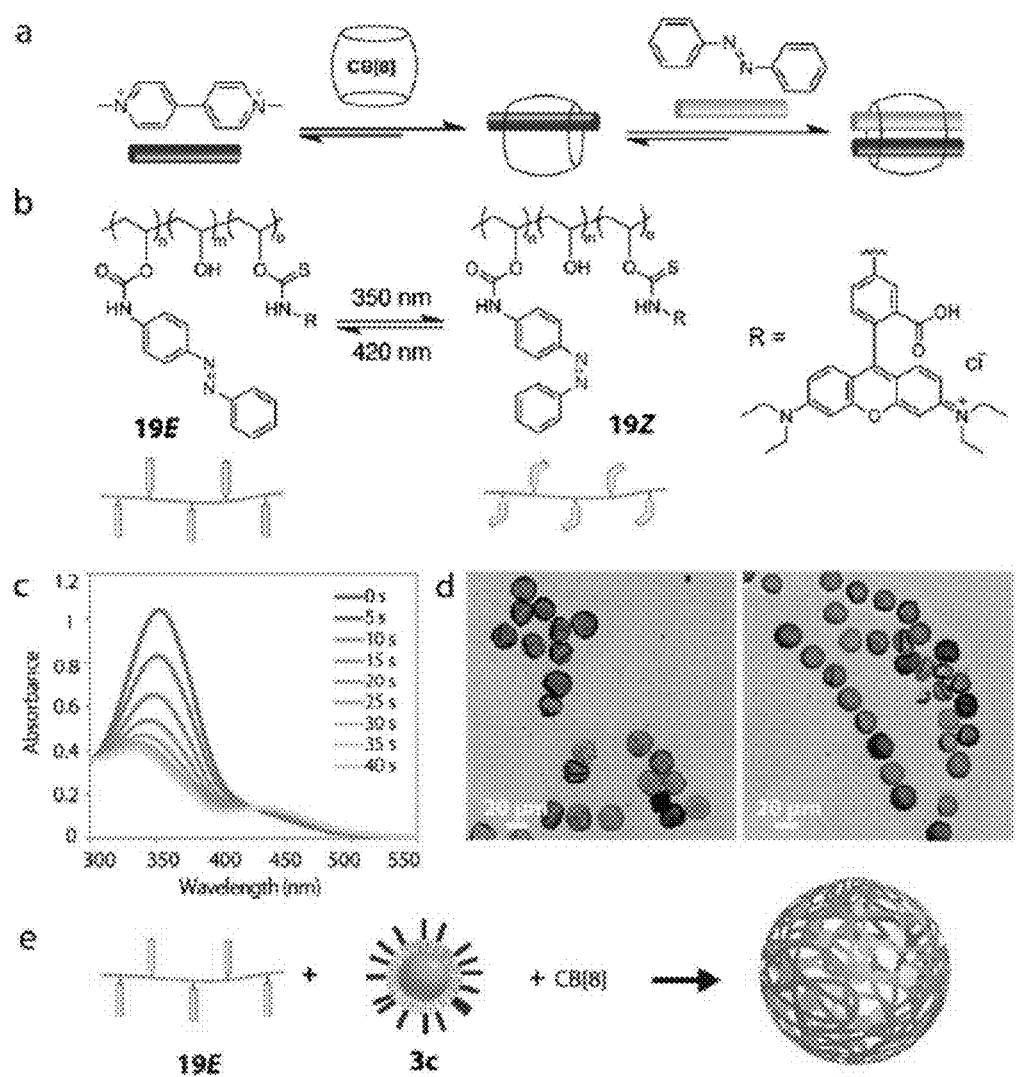
FIG. 13 is (a) a schematic showing the formation of [(trans-azobenzene)($MV^{2+}$)⊂CB[8]] ternary complex; (b)

Hence, an azobenzene-functionalized copolymer 19E was prepared with a poly hydroxyethyl acrylamide (PHeAm) polyvinyl alcohol (PVA)-based backbone (FIG. 13(b)). Upon irradiation with 350 nm light, the photoisomerization of the transazobenzene moieties occurs to produce the cis-azobenzene containing copolymer 19Z. The photochemistry of the copolymer was studied by obtaining the UV-vis spectra of the aqueous solution of copolymer 19E after photoirradiation at various time intervals. Shown in FIG. 13(c), 19E shows a significant absorption peak at approximately 350 nm, characteristic of the trans-azobenzene species. As the irradiation time lengthens, a decrease in the absorbance of trans-azobenzene is observed, accompanied by an increase in the absorbance at approximately 430 nm, typical of cis-azobenzene, until the equilibrium is reached.

Microcapsules were prepared using the copolymer 19E from microfluidic droplets containing an aqueous mixture of the copolymer, $MV^{2+}$-AuNP 3c, and CB[8] (FIG. 13(e)). As shown in FIG. 13(d), upon dehydration, microcapsules were successfully prepared showing a flattened structure with ridges and folds. The integrity of the capsules was demonstrated by rehydrating FITC-dextran-loaded microcapsules, which successfully retained the cargo without any leakage (FIGS. 14(b) and (c), 0 min). The photochemistry of the copolymer 19E as a part of the microcapsules was studied by irradiating the microcapsules dispersed in water using filtered light from a mercury lamp. After only 1 min of irradiation, an extensive leakage of the FITC fluorescence was observed (FIGS. 14(b) and (c), 1 min), which persisted and intensified as the irradiation duration increased. More notable changes were observed in the series of corresponding bright field images. The intact microcapsules prior to irradiation (FIGS. 14(b) and (c), 0 min) appeared completely degraded after exposure, leaving a random distribution of dark clusters (FIGS. 14(b) and (c), 20 min), which is thought to be clusters of AuNPs interlinked through CB[8].

These results clearly demonstrate the effectiveness of trans-azobenzene as a phototrigger in the supramolecular microcapsules. Upon irradiation, the transazobenzene species isomerized into its cis species, which was too bulky to be accommodated in the cavity of CB[8] alongside the $MV^{2+}$ moiety (FIG. 14(a)). This spatial change essentially disrupted the ternary complex, and therefore the degradation of the microcapsule shell and the release of the encapsulated cargo were achieved.

The same principle could also be applied to polymeric microcapsules, whereby the combination of $MV^{2+}$-bearing copolymer 14 and trans-azobenzene-modified copolymer 19E in the presence of CB[8] resulted in the successful fabrication of polymeric microcapsules susceptible to photochemical stimulation. As shown in FIG. 15(a), the microcapsule was capable of encapsulating the fluorescent cargo FITC-dextran (500 kDa). The integrity of the microcapsule was maintained while the content was retained upon rehydration (FIG. 15(b)). Its photochemistry was investigated by recording the fluorescence images of the microcapsule after irradiation with 360 nm light for different time intervals. However due to the lack of AuNPs as a calorimetric guide, the corresponding bright field images were not able to provide any additional information and hence were not recorded (FIG. 15(b), bright field).

The hydrated polymeric microcapsules were subjected to the same UV irradiation routine as for their AuNP-embedded counterparts. The results are summarized in FIG. 15(c), which shows a slight dissipation of the FITC fluorescence around the microcapsule after approximately 4 min of irradiation. Extended irradiation leads to more extensive leakage of the fluorescent indicator. Compared to its AuNP-embedded counterpart, which exhibited initial capsule shell degradation after merely 1 min of irradiation, the polymeric microcapsules required longer exposure to the light stimulus.

To illustrate the photo-sensitivity of the microcapsule shell in more detail, the photoisomerization experiment was also performed using laser scanning confocal microscopy (LSCM), which was expected to provide higher-quality images of the capsule shell and the release of the fluorescent cargo. A hand-held UV lamp at 365 nm was used as the alternative irradiation source with a low intensity of $8.9 \times 10^{-3}$ W/cm$^2$, since the LSCM was not equipped with a UV light source. The microcapsules containing 500 kDa FITC-dextran were rehydrated before exposure to the UV light and the cross-section images were taken after various time intervals. The capsule shell appeared to be intact despite the prolonged irradiation of 13 min, as seen by the integral capsule shell and the localization of the FITC fluorescence (images not shown). Such results were in marked contrast when compared to the previous experiment as shown in FIG. 15(d), where the leakage of the FITC-dextran was observed after merely 4 min of irradiation. This could be explained by the difference in the intensity of the hand-held UV lamp compared to that of the UV portion of the white light generated by mercury lamp (22.8 W/cm$^2$).

A detailed analysis of the rhodamine-B fluorescence images showing the capsule shell during the irradiation clearly revealed the process of the degradation of the polymeric shell (images not shown). The broadening of the rhodamine fluorescence over time is indicative of the slow diffusion of the rhodamine-bearing copolymer that has been released from the interlocked network of supramolecular ternary complexes upon the light stimulus. While such a slow process does not demonstrate the complete dissociation of the capsule shell or the release of the encapsulated cargo, it does provide evidence of the light-stimulated degradation of the supramolecularly-held polymeric microcapsule shell. These light-sensitive microcapsules were also redispersed in water over time without UV irradiation. Despite osmotic force-driven swelling, the dissipation of the rhodamine fluorescence was not observed.

Competitive Guest-Triggered Release

An additional stimulus that can be applied to these microcapsules is via the use of a competitive guest, on account of the supramolecular chemistry in the capsule shell. The use of a competitive guest to disrupt inclusion complexes is a common practice in many host-guest based supramolecular architectures (Patra et al.; *Langmuir* 2009, 25, 13852; Lan et al. *Chem. Comm.* 2012, 48, 8757).

Few examples of using competitive guests, however, can be found in the preparation and the stimuli-responsiveness of microcapsules. In an attempt to manipulate the size of a colloidal microcapsule interlinked via cyclodextrin-adamantane inclusion complexes, Patra et al. reported the use of adamantine-modified polyethylene glycol as a competitive amphiphilic guest (Patra et al., *Langmuir* 2009, 25, 13852). Subsequently, the competitive guest interferes with the host-guest recognition between the cyclodextrin host and the adamantane dithiol guest, causing the coalescence of destabilized colloidal microcapsules. In this particular example, the colloidosome is too unstable to be isolated and hence the role of the competitive guest as a trigger for controlled release of the encapsulated content was not explored.

The competitive guest used is 1-adamantamine. It belongs to the large molecular family of adamantane, which is a widely applied guest and competitive guest in the fundamental studies and application developments of many supramolecular host molecules, mostly as a result of its structural compatibility and hydrophobic nature (Liu et al. *J. Am. Chem. Soc.* 2005, 127, 15959; Chen et al. *Chem. Soc. Rev.* 2011, 40, 2254). Among these, the water soluble analogue 1-adamantamine can be used in aqueous solutions and has a high association affinity for the cavity of CB[8] ($8.2 \times 10^8$ M$^{-1}$). The use of adamantamine as a competitive guest was studied in the chain-end complexation of a functionalized poly(N-isopropyl-acrylamide) (PNIPAm) by a CB[8]-viologen complex (Rauwald et al. *Chem. Comm.* 2011, 47, 6000). While a dibenzofuran terminal moiety forms a ternary complex with CB[8] and MV$^{2+}$ in aqueous solution, the addition of adamantamine disrupts the complex to release the PNIPAm terminus (FIG. 16($a$)). Adamantamine was also used in cleaving the shell covering the polymeric microspheres via [(naphthol)(MV$^{2+}$)⊂CB[8]] complexes by competitively binding with CB[8] (FIG. 16($b$)).

Consequently, 1-adamantamine was investigated as a competitive guest in triggering the dissociation of the CB[8] complexes with naphthol and MV$^{2+}$ moieties. Polymeric microcapsules were prepared from copolymers 5 and 14, by mixing their aqueous solutions with CB[8] which is equimolar to the naphthol- and MV$^{2+}$-containing monomers (2.5× 10$^{-5}$ M) in microdroplets (FIG. 17($a$)). Encapsulated with 500 kDa FITC-dextran (1×10$^{-6}$ M) as a fluorescent indicator, these microcapsules were collected and allowed to dehydrate on a glass surface before the bright field and fluorescence images were obtained (FIG. 17($b$)). Due to the lack of internal support, the capsules collapsed to a toroidal morphology, with the majority of the FITC-dextran located around the edge of the flattened microcapsules as indicated by the more intense FITC fluorescence.

When dried microcapsules were redispersed in an aqueous solution of 1-adamantamine (100 μM), the diffusion of the FITC fluorescence was observed instantaneously (FIG. 17($c$)). The microcapsules were hard to observe in the bright-field image due to their transparency, while the initial stage of the cargo leakage was visible by the difference in fluorescence intensities of the background and of the microcapsules. The mechanism of such leakage was schematically represented in FIG. 17($d$), which depicts the disruption of the CB[8] ternary complex with naphthol and MV$^{2+}$ moieties by the complexation of CB[8] and 1-adamantamine, resulting in the dissociation of copolymers 5 and 14 and the degradation of the capsule shell. The release of the FITC labelled cargo was monitored for another 15 min, showing the blurring of the fluorescence of the microcapsules and of the background, suggesting the gradual but complete degradation of the microcapsules. Overall, the use of a competitive guest has been demonstrated to trigger the dissociation of the CB[8] ternary complex in the capsule shell and therefore the release of the encapsulated cargo.

Temperature-Triggered Release

Temperature is a versatile trigger for the cargo release of many types of microcapsules. One of the most widely applied building blocks is poly(N-isopropylacrylamide) (PNIPAm), a thermo-responsive polymer that undergoes a coil-to-globule transition at a lower critical solution temperature (LCST) (32° C.) (Wu et al. *Phys. Rev. Lett.* 1998, 80, 4092). Below the LCST, PNIPAm is water soluble and behaves as a coil of an amphiphilic polymer on account of the isopropyl groups in each monomer of PNIPAm. Above the LCST, PNIPAm phase separates to yield colloidal sized globules, which are too insoluble to remain in water. This temperature-dependent phase separation has been the basis of the trigger mechanism of many systems. Microcontainers prepared from a layer of N,N'-methylene bisacrylamide (MBA) cross-linked NIPAm templated with monodisperse silica particles have been reported (Zha et al. *Adv. Mater.* 2002, 14, 1090). The temperature-induced phase transition of PNIPAm above the LCST led to significant decrease in the particle dimensions and pore size that could entrap FITC molecules, while the cargo was released when the PNIPAm shell swelled below the LCST (Gao et al. *Polymer* 2005, 46, 1087). PNIPAm can also exist in a mixture of copolymers to form the capsules shell by grafting linear PNIPAm chains into the pores of the prepared polymer shell using plasma-graft pore-filling polymerization (Chu et al. *Langmuir* 2002, 18, 1856). As PNIPAm shrinks when the temperature is above the LCST, the other polymer remains intact and hence pores are created to release the encapsulated content. Thermosensitive microcapsules could also be fabricated using a double emulsion method by filling the middle liquid phase with a microgel of PNIPAm (Yang et al. *Lab Chip* 2009, 9, 961). The shrinkage of the hydrogel at elevated temperature ruptured the shell to release the cargo.

Therefore, the use of PNIPAm as a thermo-trigger for microcapsule cargo release was investigated. As a result of the modularity of the supramolecular chemistry in the capsule shell, the biphenyl functional group was employed to form an alternative hetero-guest combination with MV$^{2+}$. The formation of 1.1:1 [(MV$^{2+}$)(biphenyl)⊂CB[8]] ternary complexes follows the same two-step mechanism as shown in FIG. 19($a$), as a result of the structural similarity of the biphenyl moiety to other electron-rich guest functional groups (Biedermann et al. *Chem. Eur. J.* 2010, 16, 13716). The copolymer 20 was therefore synthesized with a PNIPAm backbone and biphenyl moieties as multivalent pendants. Microdroplet precursors were prepared using an aqueous mixture of the copolymer 20 and the MV$^{2+}$-bearing copolymer 14 in the presence of CB[8] (FIG. 17($b$)). Dehydration of the droplets yielded shriveled capsule-like structures with high monodispersity (FIG. 17($c$)). A close-up image of the microcapsule formation process reveals the difference in the morphology at various stages of dehydration (FIG. 17($d$)). The resemblance of these capsule-like structures to previously verified polymeric microcapsules confirms the stable capsule formation.

The temperature-dependent behaviour of the PNIPAm-based microcapsules was then studied by monitoring the rehydrated capsules on a temperature-controlled microscope stage. The temperature was set to rise by 5° C. per minute from the ambient temperature of 25° C. to 60° C. Considering the LCST of PNIPAm is approximately 32° C., the higher temperature above the LCST was designed to investigate the thermostability threshold of the microcapsules. A gradual but significant swelling of the microcapsules was observed as the temperature increased steadily. After 4 mins of heating at 45° C., nearly all microcapsules resumed their spherical shape, contrary to their original shriveled structures. After further heating to reach 60° C., clusters of dark spots appeared in the microcapsules, which is reminiscent of the morphology of the light-sensitive microcapsules after prolonged irradiation.

A negative control was prepared using the combination of copolymers 5 and 14, which do not possess thermosensitive polymer backbone. Bright field microscopic images of the capsules showed the lack of significant changes to the appearance of the microcapsules when rehydrated with increasing temperature. At room temperature, microcapsules of both formulations were maintained in water for 5 hours and no apparent changes to the integrity of the microcapsules were observed.

These observations provide promising evidence for the thermo-responsive nature of these PNIPAm-based microcapsules. This preliminary result showing the contrast in the extent of swelling above the LCST for the two types of microcapsules indicates the role of the PNIPAm-based copolymer 20 in the microcapsule formulation. Further experimental data are needed from monitoring the behaviour of cargo-loaded PNIPAm microcapsules at elevated temperature, where any changes in the pore size would be reflected by the retention or the leakage of the cargo. It is also envisaged that when both copolymers contain the PNIPAm functionality a far greater response will be observed.

Capsule Preparation

Microcapsules were prepared following from CB[8], copolymer 5, MV$^{2+-}$AuNP 3c, copolymers 5 and 14. 5 and 3c is known from the work of Zhang et al., *Science* 2012, 335, 690. Other polymers are readily prepared using the techniques described by Zhang et al.

In a typical experiment, the concentrations of the ternary complex-forming functional groups in the stock solutions of the reagents were 100 μM and upon mixing (1:1:1 v:v:v), the final concentrations were 33 μM for individual reagents. After formation, droplets were either collected in the PDMS reservoir downstream or transferred to a microscope slide. Upon collection, droplets were allowed to dehydrate over time for the complete formation of microcapsules. Optical microscope (IX71, Olympus) images were obtained for the dehydrated structures.

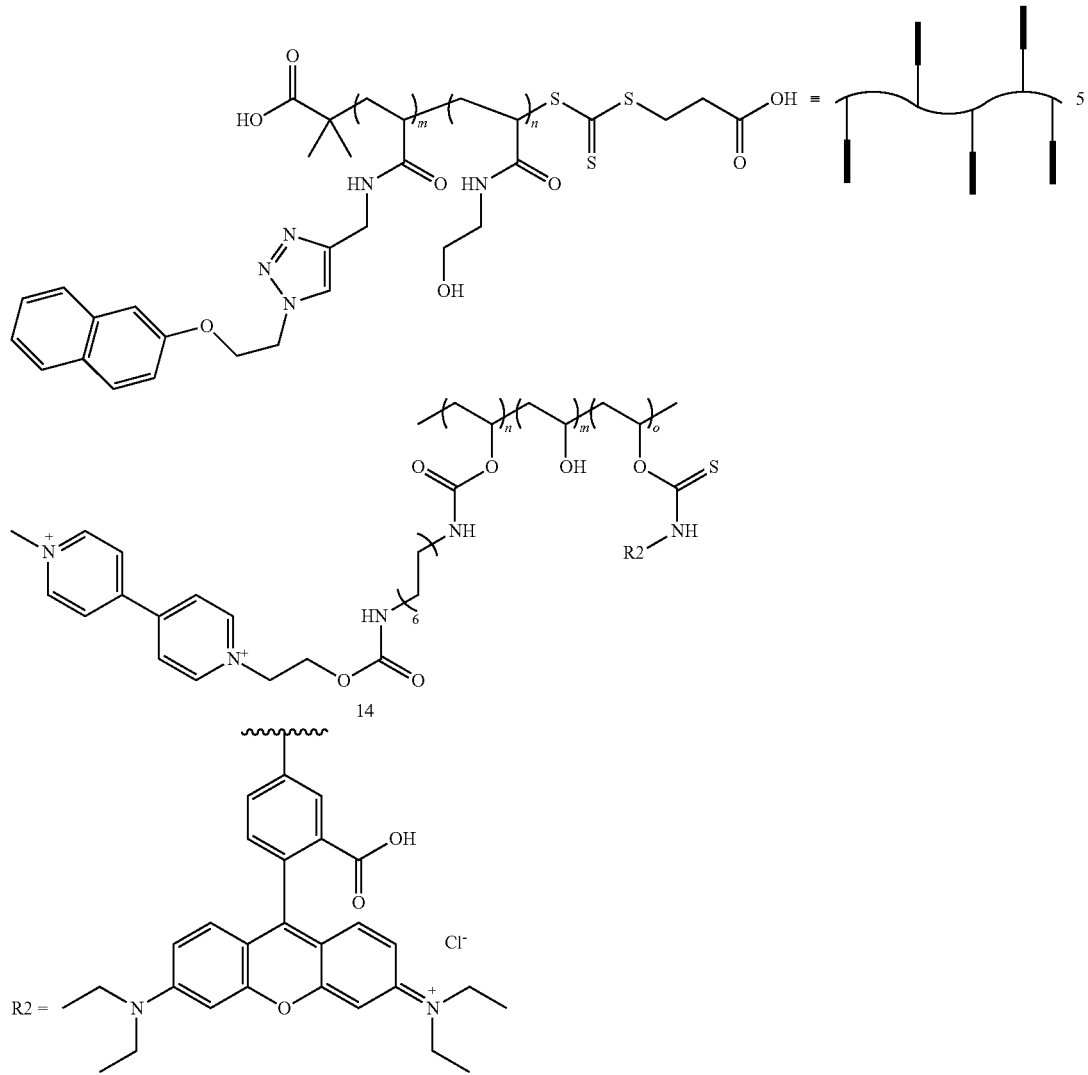

Using a one-inlet device design, a fluorous oil phase and an aqueous mixture of capsule-forming components were loaded into syringes with needles fitted with polyethylene tubing. The syringes were mounted on syringe pumps, while the other end of the tubing was inserted into the aqueous inlet of the device. Droplet formation was initiated as oil was first pumped into the device at 200 μL/h to fill the appropriate channels. The aqueous dispersed phase was then pumped into the device at 100 μL/h. Fluorous surfactant (2% w/w) was dissolved in FC-40 oil and used as the carrier phase.

To encapsulate the model cargo fluorescein isothiocyanate (FITC)-labelled dextran (500 kDa), a stock solution of the dextran was prepared (5 μM or 10 μM), mixed with the aqueous mixture of the capsule-forming reagents (1:3 v:v) and pumped into the microfluidic device. The final concentration of the dextran in droplets was either 1.3 μM or 2.5 μM.

These dextran-encapsulating droplet precursors were collected and dried in a similar fashion to their empty counterparts.

To enable long-term monitoring of the microcapsules in an oxygen-free environment, a simple microscope-compatible chamber was set up using a modified tissue culture flask (40 mL, Greiner™). A sample of microcapsules on a small piece of glass slide was placed inside the flask before the nitrogen gas was continuously introduced to the flask for 2 h using a needle pierced through the filter of the cap. In the meantime, 1 mL of water in a small vial was deoxygenated in a similar way by bubbling nitrogen gas for 1 h before a 0.5 g of $Na_2S_2O_4$ was added. The vial was quickly swirled for $Na_2S_2O_4$ to fully dissolve and then the solution was loaded to a syringe. After removing oxygen from the chamber, the cap was then sealed with Parafilm® and mounted on the fluorescence microscope to allow adjustment for focus and light intensity. Bright field and fluorescence images of the dehydrated microcapsules were obtained first. To rehydrate the microcapsules with the $Na_2S_2O_4$ solution, a few drops of the aqueous reagent was applied over the dehydrated capsules using the pre-filled syringe through the filter in the cap. The syringe was then withdrawn and the cap resealed again with more Parafilm® to ensure the oxygen-free environment, before bright field and fluorescence images of the rehydrated microcapsules were taken at different time intervals. Negative control was performed in the same procedure, but replacing the $Na_2S_2O_4$ solution with Milli-Q water.

A aqueous solution of the azbenzene-functionalized copolymer 19E ($3.7\times10^{-7}$ M, [trans-azobenzene]=$1.84\times10^{-4}$ M) was prepared and loaded into a quartz cuvette. An initial ultraviolet/visible (UV/vis) absorption spectrum was obtained before the solution was irradiated with 350 nm light in a Luzchem photoreactor with ten UV-A fluorescent lamps (for 350 nm irradiation) for various time intervals. UV/vis spectra of the solution was obtained after every photo-irradiation and the spectra overlaid for trend visualization.

Microcapsules were prepared following the procedure outlined above using CB[8], copolymer 19E, and $MV^{2+}$-AuNP 3c, or CB[8] and copolymers 17E and 14. The fluorescence microscope setup is described below. A dehydrated sample of microcapsules on a glass slide was mounted on the fluorescence microscope before its bright field and fluorescence images were obtained. The sample was rehydrated with a drop of Milli-Q water and was subjected to UV irradiation using the DAPI excitation filter (350 nm, with 25 bandwidth) for various time intervals. At the end of every UV irradiation, the bright field and FITC-fluorescence images were recorded.

The LSCM experimental is described below. Briefly, the dehydrated microcapsules were collected on a microscope cover slide. Samples were illuminated with either 488 nm or 543 nm laser lines for exciting the FITC-dextran and the rhodamine-containing copolymer respectively. The microcapsules were rehydrated and allowed to swell to the original spherical shape before a hand-held UV lamp (365 nm, Blak-Ray®) was used for irradiation. The sample was irradiation for various time intervals and the fluorescence cross-section images were obtained at the end of every irradiation. All images were taken in 512×512 pixels. The fluorescence intensity profiles and the two-color overlay fluorescence images were processed by Leica software.

Microcapsules were prepared following the procedure outlined above using CB[8] and copolymers 5 and 14. The fluorescence microscope setup is described below. A dehydrated sample of microcapsules on a glass slide was mounted on the fluorescence microscope before its bright field and fluorescence images were obtained. The sample was rehydrated with a drop of 1-adamantamine (1 mM) before the fluorescence images were recorded immediately.

Microcapsules were prepared following the procedure outlined above using CB[8] and copolymers 20 and 14, or CB[8] and copolymers 5 and 14. The fluorescence microscope setup is described below. A dehydrated sample of microcapsules on a glass slide was mounted on the optic microscope fitted with a thermo-controlled stage. The sample was rehydrated with Milli-Q water before its bright field images were obtained while the temperature increased at a rate of 5° C. per min until it reached 60° C.

Imaging

Fluorescence images were recorded using an EM-CCD camera (Xion+, Andor Technologies model A247 from Pixelinkand) connected to an inverted microscope (IX 71, Olympus) operating in epifluorescence mode, mounted with an automatic microscope stage (ProScan II, Prior Scientific). A mercury lamp (U-LH100HG, Olympus) was installed for wide-spectrum illumination with appropriate filters and dichroics (BrightLine©, Semrock) fitted to separate the fluorescence excitation and emission light. A computer controlled shutter was added to the excitation path to reduce the time during which the specimen was excited upon to minimize photobleaching. The camera, the stage and the shutter were controlled by a custom-written software (LabVIEW 8.2, National Instruments), which was used to record and analyze bright field and fluorescence images.

The integrity of the microcapsules was investigated using fluorescence microscopy.

Microdroplet precursors of various formulations encapsulating FITC-dextran (500 kDa) were prepared and allowed to dehydrate on a glass slide. The bright field and fluorescence images of the dehydrated structure were first recorded. The structure was then rehydrated with a drop of Milli-Q water before the fluorescence and bright field images were immediately recorded. To allow mechanical force-induced rupture of the capsule shell, the rehydration of the dehydrated structures was achieved by placing a water droppendant cover slide over the sample.

Sample preparation for LCMS imaging was initiated by collecting aqueous droplets in FC-40 oil in a PDMS reservoir mounted on a microscope cover slide. Samples were illuminated with either 488 nm or 543 nm laser lines for exciting the FITC-dextran and the rhodamine-containing copolymer respectively. The emission of FITC-dextrans, peaking at 520 nm (product data sheet) and the emission of rhodamine-containing copolymers, peaking at 582 nm, were collected over emission band passes of 550-540 nm and 560-650 nm respectively. The sample was imaged in the reservoir at focal plane at different time intervals to capture capsules at different stages of dehydration. The cross-section images of the droplet precursors and the resulting microcapsules were also obtained along the z-axis at a step size of 0.13 μm for every 1.5 μm. During acquisition, a desired fluorescence intensity was obtained by adjusting the intensity of laser, gain and offset, line averaging and frame averaging and the setting was kept constant for the remainder of the time.

Covalent Links and Crosslinks

Cucurbit[8]uril (CB[8]), can accommodate up to two aromatic guest molecules simultaneously inside its cavity as shown in FIG. 19(b), to form either 1:2 CB[8]•(guest)$_2$ homoternary complexes with monocationic guests or 1:1:1 heteroternary complexes with both a dicationic and a neutral guest. The preorganisation of two anthracenemoieties (see FIG. 19(a)) in the cavity of CB[8] in a face-to face π-π-stack dramatically increases the rate of photodimerisation between the two anthracenes and can be further utilised to photochemically ligate and cross-link polymers. This is discussed and exemplified below.

The anthracene-molecules were designed to carry a positive charge directly adjacent to the aromatic core in order to allow for strong complexation with CB[8]. For steric reasons, substitution of the 9-position of anthracene would impede the ability to form ternary complexes with CB[8]. Thus, anthracene derivatives carrying a substituent in the 2-position were used. Commercially available 2-aminoanthracene was subjected to reductive amination with para-formaldehyde and sodium cyanoborohydride which proceeded smoothly to yield N,N'-dimethyl-2-aminoanthracene in good yield and high purity without the need for further purification. Subsequently, quaternary ammonium salts were obtained employing powerful alkylating reagents such as methyl iodide (to yield 1a) and propargyl bromide (to yield a "click"-able precursor to 1b and 1c) with moderate yields.

Nevertheless, the purification steps (filtration) and ion-exchange to yield the chloride salt required only minimal effort. Labelling of macromolecules with such anthracene-moieties was achieved through copper-accelerated cycloaddition reactions from readily available end-group functional azidopoly(ethylene glycol) (PEG) and side-chain functional azidohydroxyethyl cellulose followed by purification through dialysis.

Host-Guest Complexation and Photodimerisation of Anthracene 1a

Initially, the binding characteristics of small molecule 1a with CB[8] were studied by $^1$H NMR, UV/vis and fluorescence spectroscopy, ESI-MS and isothermal titration calorimetry (ITC). In agreement with literature reports of other homoternary 1:2 CB[8]•(guest)$_2$ complexes (Jiao et al. *J. Am. Chem. Soc.*, 2010, 132, 15734; Liu et al. *Chem. Eur. J.*, 2011, 17, 9930), the characteristic shifts of the aromatic proton peaks were observed in the $^1$H NMR spectrum upon addition of CB[8]. UV/vis titration experiments (not shown) yielded evidence for a 1:2 complex stoichiometry, see FIG. 19(b). Furthermore, a strong excimer band emerged in the emission spectra of 1a when CB[8] was added, which is indicative of a face-to-face π-π-stack of anthracenemoieties in the host's cavity (Liu et al. *Chem. Eur. J.*, 2011, 17, 9930-9935). The dominant species in the ESI-MS spectra can be assigned to the CB[8]•1a$_2$ complex, which further confirms the suggested 1:2 homoternary complex formation of CB[8] with 1a.

Moreover, in ITC experiments the inflection point of the isotherm was observed at a 1:2 ratio of CB[8] to 1a, in agreement with the proposed 1:2 complex stoichiometry in solution. The overall aqueous ternary binding constant Ka(ternary)=(1.0±0.5)×10$^{12}$ M$^{-2}$ is essentially identical to the Ka(ternary) of a recently reported anthracenepyridinium guest. A deconvolution of Ka(ternary) into the individual binding constants $K_a(1)$ and $K_a(2)$, albeit numerically somewhat uncertain (Heitmann et al. (*Am. Chem. Soc.*, 2006, 128, 12574), $K_a(1)$=(4±1)×10$^4$M$^{-1}$ and $K_a(2)$=(2±1)×10$^7$ M$^{-1}$, clearly shows strong positive cooperativity, in contrast to previous reports of structurally similar guests (Heitmann et al. *J. Am. Chem. Soc.*, 2006, 128, 12574; Jiao et al. *J. Am. Chem. Soc.*, 2010, 132, 15734). Finally, the binding of 1a with CB[7], a smaller member of the cucurbit[n]uril family that can only form 1:1 complexes with aromatic guests (Kim et al. *J. Am. Chem. Soc.*, 2000, 122, 540; Lagona et al. *Angew. Chem. Int. Ed.*, 2005, 44, 4844) was also investigated with the aforementioned techniques and most importantly no excimer band was observed in the emission spectrum of an aqueous solution of CB[7] and 1a.

Having established that CB[8] efficiently π-π stacks the anthracene-units of 1a in its cavity, an investigation into the dimerisation of those moieties upon photoirradiation was carried out. It was previously demonstrated by Inoue et al. that the photodimerisation of anthracene-carboxylic acids and their g-cyclodextrin-appended esters in the presence of CB[8] yielded a completely different product distribution than in the absence of the CB[8] host (Yang et al. *J. Am. Chem. Soc.*, 2008, 130, 8574). From the reported binding constants, $K_a(1)$=2.4×10$^5$ M$^{-1}$ and $K_a(2)$=1.4×10$^4$ M$^{-1}$, it is unlikely that the CB[8] host quantitatively preorganised both molecules of neutral or negatively charged anthracene at the experimental conditions used (50 μM of CB[8] and anthracene species) and much more likely that the 1:1 complex was the predominant species in solution. Additionally, no acceleration in the photodimerisation rates were reported in the presence of CB[8], in contrast to previous reports where cyclodextrins were employed as hosts (Tamaki *Chem. Lett.*, 1984, 53; Nakamura et al. *J. Am. Chem. Soc.*, 2003, 125, 966). More recently, a neutral, covalently linked anthracene-π-π-stack dimer was utilised by the same group and photodimerisation in the presence of CB[8] resulted in impressively high ee-values of the asymmetric dimers. We were hoping to shorten the photodimerisation time required for anthracene derivatives, previously reported to take ca. 1 h to reach full conversion through the non-covalent template effect that results from the cooperative binding of positively charged anthracene derivatives with CB[8] (Yang et al. *J. Am. Chem. Soc.*, 2008, 130, 8574). Indeed, photoirradiation of a dilute aqueous solution of 1a (10 μM) and 0.5 equiv. CB[8] with a 350 nm light source led to a rapid decrease in the absorbance of the bands centered around 254 nm and 366 nm with an isosbestic point at 222 nm, reaching full conversion within 3 minutes (FIG. 20(a)).

Moreover, the fluorescence emission intensity decreased upon photoirradiation. Both the UV/vis and fluorescence kinetic data yielded an identical rate constant of 2×10$^{-2}$ s$^{-1}$ from mono-exponential fits. Control experiments carried out under identical conditions either in the presence of 1.0 equiv. of CB[7], or in the absence of any host, resulted in only 10% conversion on the same time scale and the rate constants in both cases were an order of magnitude lower than when the photodimerisation was carried out in the presence of CB[8] (see Table 1). The UV/vis spectral features of the product formed when 1a was photoirradiated in either the absence or presence of the CB[8] host were almost identical, suggesting that in both instances structurally similar products were formed. Additional confirmation for the proposed photodimerisation reaction came from ESI-MS measurements of the UV-light treated 1a and CB[8] mixture.

| Compound | Conc. of 1 (μM) | $k_{photo}{}^a$ (10$^{-3}$ s$^{-1}$) |
|---|---|---|
| 1a | 10 | 3 |
| 1a + CB[7] (1:1) | 10 | 2 |
| 1a + CB[8] (2:1) | 10 | 21 |
| 1a | 1 | 2 |
| 1a + CB[8] (2:1) | 1 | 17 |
| 1b | 10 | 2[b] |
| 1b + CB[8] (2:1) | 6 | 9 |
| 1c | 10 | 9[b] |
| 1c + CB[8] (2:1) | 6 | 13 |

[a]Photoreaction rates (350 nm irradiation) were determined from monoexponential fits of the absorbance at 254 nm vs. irradiation time. Identical sample volume and geometry, cuvette and light source were used in all cases.
[b]Side reactions occur After 15 minutes of photoirradiation only one species was observed in the ESI-MS spectrum, it possessed the correct m/z value and charge state and was identified as the [CB[8]•2a]$^{2+}$ complex; additional peaks including the 1:1 binary complex [CB[8]•1a]$^{+}$ were present prior to photoirradiation in the ESI-MS but were not observed after photoirradiation. Acetonitrile was subsequently added to the ESI-MS samples in order to release the anthracene-dimer from the ternary CB[8] complex. After photoirradiation the species at the m/z value 236 Da possessed a +2 charge, which is characteristic of the photodimer 2a whereas prior to photoirradiation, the monomeric 1a with a +1 charge was observed at the same m/z value.

Structural information was obtained from 1H NMR experiments (CB[8]: 1a=1:2; 500 μM in 1a). After 15 minutes of photoirradiation, a complete disappearance of the proton signals corresponding to the anthracene reactants in the CB[8] cavity were observed with the emergence of new peaks that can be assigned to a [4+4] anthracene cyclodimer (2a) as can be seen in the $^1$H NMR spectrum in FIG. 20(b). However, in the absence of the CB[8] host, only 50% reactant conversion was reached even after three hours of UV-light exposure. It is also important to note that a larger number of species were formed when 1a was photoirradiated in the absence of the CB[8] host. Subsequent NMR analysis of the uncomplexed photoreaction products further substantiated this finding. From the $^1$H and $^{13}$C NMR spectra of the products, it is clear that a [4+4]-type photoreaction of the anthracene moieties occurred, e.g. the 9- and 10-anthryl protons and carbons shifted upfield into the aliphatic peak region upon photoirradiation. In principle, four different regioisomers could result as racemic mixtures upon dimerisation of 1a. Analysis of the $^1$H and $^{13}$C NMR spectra revealed that an approximately equimolar mixture of two regioisomers was formed in presence of CB[8], whereas in the absence of host all four regioisomers were observed. The attempted structural assignment of such products by NOESY and COSY NMR was inconclusive, however, it is reasonable to assume that the NMR peaks of the N(CH$_3$)$_3$ groups are more downfield shifted for the head-to-head than for the head-to-tail dimers on account of charge accumulation on one face of the molecule. Under this premise, it follows from a comparison of all NMR spectra that only the head-to-tail dimers were produced for the CB[8] mediated photodimerisation.

The head-to-tail arrangement of two 1a molecules in the cavity of CB[8] is also energetically strongly preferred on account of minimised charge repulsion and maximised cation-π interactions of the quaternary ammonium groups with the carbonyls on both CB[8] portals, and as such it is most plausible that the head-to-tail templating of two anthracene monomers results in the preferential formation of the head-to-tail photodimer. Thus, from the combination of all the experimental observations, it can be concluded that the non-covalent tethering of two small-molecule anthracenemoieties carrying positive charges with CB[8] accelerates the anthracene photodimerisation reaction and reduces the number of regioisomers and side products.

Host-Guest Complexation and Photodimerisation of an Anthracene-Labeled PEG-Polymer In an effort to exploit the anthracene [4+4] photodimerisation for the ligation of polymeric entities, anthracene end-group labelled PEG (1b) with a molecular weight of 2.4 kDa was synthesised. The spectroscopic signatures observed for the CB[8] titration into to an aqueous solution of polymer 1b were very similar to its small-molecule analogue 1a, e.g. an excimer band around 500 nm in the emission, an isosbestic point at 259 nm in the UV/vis, and the characteristic upfield shifts of the aromatic protons in the 1H NMR spectrum which suggested that CB[8] can tether together two polymeric entities even at remarkably low concentrations (10 μM in 1b). The ternary binding constant, K$_a$(ternary)=(2.2±1.0)×10$^{10}$ M$^{-2}$ for polymer 1b was found by ITC measurement to be two orders of magnitude lower than that for the small molecule 1a, but is still sufficiently large to enable almost quantitative ternary complex formation in the μM-concentration regime.

Photoirradiation of the CB[8]•1b$_2$ complex with a 350 nm light source was again accompanied by a reduction in the fluorescence intensity, a decrease in the absorbance at 254 nm and 366 nm and the appearance of an isosbestic point at 226 nm, suggesting that the photoreaction of the ternary complexes CB[8]•1a$_2$ and CB[8]•1b$_2$ yielded structurally similar products. The rate of the CB[8] mediated photodimerisation of 1b is 9×10$^{-3}$ s$^{-1}$, approximately two times slower than for the small molecule 1a at the same concentration (see Table 1).

Further structural verification was obtained by ESI-MS experiments. Unfortunately, no ESI-MS signals could be observed for 1b (and its CB[8] complex) in neat aqueous solutions, thus, a large excess of acetonitrile had to be added (1:10) prior to injection. As was mentioned before, decomplexation of CB[8] assemblies readily occurs in H$_2$O:acetonitrile mixtures. Consequently, the peaks corresponding to the monomeric 1b polymer chains were observed prior to photoirradiation (results not shown). After 15 minutes of 350 nm light treatment in the presence of CB[8], the charge, assigned by the isotopic spacing, of the species at the same m/z value had doubled confirming that the photodimer 2b was indeed present (results not shown). The isotopically assigned charges were in agreement with those obtained from the peak-to-peak distance between the polymer-chains consisting of N and of (N+1) monomeric units. For example, ethylene oxide has a monomeric mass M (ethylene oxide) =44 Da and thus a m/z difference of 44 Da and 22 Da prior to and after photoirradiation in the presence of CB[8] yields charges of z=1 and z=2, respectively. A quantitative analysis of 1b conversion into the photodimerised polymer 2b is not possible using ESI-MS as the signal intensity is highly dependent on the ionization efficiency, and thus on the charge and length of the polymer chains, both of which were doubled upon photodimerisation. Thus, the photodimerisation conversion was monitored by $^1$H NMR experiments and was found to be quantitative within 15 minutes of photoirradiation when 0.5 equiv. of the host CB[8] was present (500 μM in 1b).

Furthermore, a shift of the retention time was observed in gel permeation chromatography (GPC) experiments, after photo irradiation of the 1b and CB[8] mixture, suggesting that a covalent bond was formed between the anthracene endgroups of two polymer chains. Prior to photoirradiation, the non-covalent CB[8] mediated ternary complex was not strong enough to withstand the separation forces on the GPC columns (at a flow rate of 0.6 mL/min) and resulted in decomplexation into the individual components, i.e. the GPC chromatograms of b alone, and the CB[8]•1b$_2$ complex were almost identical.

Photochemical Side Reactions in the Absence of the CB[8] Host

It was surprising that the rate of reactant consumption in the absence of the CB[8] host was similar for the small molecule 1a and polymer 1b, see Table 1, since a bimolecular cycloaddition should be sensitive to the rate of diffusion of the reactants. However, the relatively fast reactant consumption of 1b in the absence of CB[8] is the result of competing side reactions other than the anthracene-dimerisation. For instance, while the absorbance at 254 nm decreased upon photoirradiation, there was an increase in the absorbance in the 265-400 nm region when the sample was irradiated in the absence of CB[8], which is in contrast to the aforementioned findings for 1a, CB[8]•1a$_2$ and CB[8]•1b$_2$. Additionally, reversing the order of photoirradiation and CB[8] addition resulted in markedly different absorption spectra, suggesting that different chromophoric species are formed upon irradiation in the absence and presence of CB[8].

UV-light exposure of an aqueous solution of 1b led to the appearance of an emission band around 525 nm while irradiation of 1a, CB[8]•1a$_2$ and CB[8]•1b$_2$ solutions was accompanied by a decrease in the emission intensity. Additionally, this red-shifted emission band did not vanish if CB[8] was added after UV-light exposure. Structural information from ESI-MS experiments gave further evidence that photoirradiation of 1b in the absence and presence of CB[8] led to completely different photoreaction products. In fact, no evidence fore dimer of 1b could be found in the ESI-MS spectrum of a photoirradiated 1b solution, however, strong signals that could be attributed to a degraded hydroxyl-terminated poly(ethylene glycol) monomethylether, [HO—(CH$_2$CH$_2$—O)$_n$CH$_3$+Na]+ species were found. In addition, the degraded PEG showed a large polydispersity while the 1b starting material possessed a much narrower molecular weight distribution. It therefore must be concluded that the photoirradiation of 1b in the absence of the host is accompanied by hydrolytic cleavage of PEG chains at random positions. The cleavage of the anthracene-polymer linkage was also witnessed in $^1$H NMR experiments, revealing that only a small fraction of the polymer chains carried an aromatic end group after UV/light exposure. As further evidence, the anthracene by-product had precipitated as a red solid from the aqueous solution after photoirradiation of 1b in the absence of CB[8] host. Moreover, the residual aromatic peaks remained downfield (7.0-9.0 ppm), even after subsequent addition of CB[8], and were thus distinctively different from those of the covalent anthracene-dimers that were formed in the presence of CB[8].

Unfunctionalised PEG does not absorb light at 350 nm and was found to be stable under photoirradiation in a control experiment, thus, the degradation process of 1b is most likely initiated by the anthryl end group. A photoelectron transfer (PET) from the triazole unit of 1b to the cationic anthracene-moiety followed by thermal redox or radical reactions is a plausible mechanism for the cleavage of the anthracene-moiety and decomposition of the polymer backbone upon photoirradiation. It is worth mentioning that these side reactions were not likely the result of a photo-oxidation with dioxygen (O$_2$) since UV-light exposure of degassed aqueous solutions of 1b caused similar spectral changes at comparable comparable rates. From a synthetic point of view, it is of foremost importance that CB[8] complexation of the cationic anthracene moieties completely changed the photochemical reaction pathway from a degradation reaction in the absence to the desired anthracene-dimerisation in the presence of the CB[8] host.

Gel-Formation and Photochemical Crosslinking

In order to modify materials properties and exploit our anthracene dimerisation findings, side-chain functionalisation of hydroxyethyl cellulose (HEC) with the anthracene-moieties was carried out to induce supramolecular gelation through homoternary complexation upon addition of CB[8] followed by photo-crosslinking. The formation of supramolecular gels through non-covalent 1:1:1 ternary complex formation with CB[8] has been demonstrated (Appel et al. *J. Am. Chem. Soc.*, 2010, 132, 14251; Appel et al. *J. Am. Chem. Soc.*, 2012, 134, 11767). It would be advantageous for certain applications if covalent crosslinks could be introduced after the polymer has self-assembled into a network in order to increase the mechanical stability of the polymer and to slow down gel erosion. Here only two, instead of three, components are needed to trigger gelation: the anthracene-labeled HEC and CB[8], see FIG. 21(*b*) form schematic representation. FIG. 21(*a*) gives a pictorial view of the gels prior to and after photoirradiation. A 1.0 wt % solution of 1c in water is mildly viscous and fluoresces "blue" under UV-light, which is indicative for single anthracene units.

However, when CB[8] was added (0.5 equiv. per anthracene moiety), the fluorescence colour changed from blue to green, representative of the anthracene excimer emission from the 2:1 complex with CB[8] (second vial from the right). The solution also became much more jellylike but did not form a free-standing gel. However, photoirradiation for 15 minutes with a 350 nm light source resulted in a cross-linked polymer to such an extent that it remained a free-standing solid, suggesting that a covalently crosslinked polymer-network was formed (vial on the right in FIG. 21(*a*)). In the absence of CB[8] host, the photo-crosslinking did not occur to any appreciable extent leaving the viscosity of a 1.0 wt % of solution of modified HEC polymer unchanged (second vial from the left), even if the sample is photoirradiated for one hour. To quantify the mechanical strength of the materials, rheological experiments were carried out.

Mechanical testing of the hydrogels demonstrated the great improvement of the materials properties upon addition of CB[8] and subsequent UV-light treatment, which were far superior to those in the absence of the host.

Moreover, CB[8] complexation suppressed photochemical side reactions including degradation of the polymer backbones that were readily observed upon irradiation in the absence of the CB[8] host.

Capsule Formation and Photochemical Crosslinking

The methods above were adapted to provide a capsule having a shell including a network obtainable from the covalent cross-linking of a supramolecular network. The capsules were prepared using the methodologies established by Zhang et al., *Science* 2012, 335, 690 for the formation of capsules from microdroplets. In this example, anthracene-labelled hydroxyethyl cellulose was used as the sole building block, and this polymer was non-covalently linked and cross-linked with CB[8] at an aqueous droplet interface in an oil continuous phase. After formation of a capsule, the shell was irradiated thereby to generate covalent bonds between the anthracene guest molecules.

To generate water-in-oil microdroplets, three different fluids were injected into a microfluidic device by three syringe pumps (PHD, Harvard Apparatus) with controlled flow rates. Flourinert FC-40 (3M) containing a 3 wt % XL-171 nonionic surfactant and 2 wt % Krytox® 157FS (Dupont) was used as the continuous phase. One discontinuous aqueous phase was prepared by dissolving cucurbit [8]uril (CB[8]) in water, and another discontinuous phase was prepared by dissolving anthracene labelled hydroxyethyl cellulose (HEC, Mw=720 kDa) in water.

The continuous phase and each of the discontinuous phase solutions were loaded into three 1 mL syringes respectively before connecting to a microfluidic chip. Syringes with needles were mounted on syringe pumps and fitted with polyethylene tubing, while the other end of the tubing was inserted into the appropriate inlets of a microfluidic chip. Microdroplets formation was initiated as Flourinert FC-40 was first pumped into the device at the rate of 60 µL/h to fill the appropriate channels. The aqueous dispersed phase was then pumped into the device at 10-40 µL/h depending on individual experiment. In a typical experiment, the concentrations of anthracene labeled HEC and CB [8] were 60 µM and 30 µM respectively. All aqueous solutions were made in deionized water treated with a Milli-Q™ reagent system ensuring a resistivity of >15 MΩcm$^{-1}$. After formation, microdroplets were either collected in a PDMS reservoir downstream or transferred to a microscope slide.

Upon collection, droplets were allowed to dehydrate over 5 hours for the complete formation of isolated microcapsules. The prepared microcapsules were irradiated in 365 nm UV light for 60 seconds thereby to crosslink microcapsules with covalent bond by anthracene molecules.

Thus, host-accelerated photo-dimerisation was successfully applied to suitably end-group functionalised poly(ethylene glycol) and sidechain functionalised hydroxyethyl cellulose, which resulted in polymer-dimerisation, and gel network formation and capsule formation.

REFERENCES

Abraham et al. *Advanced Materials* 2008, 20, 2177
Ameloot et al. *Nat. Chem.* 2011, 3, 382
Appel et al. *J. Am. Chem. Soc.,* 2010, 132, 14251
Appel et al. *J. Am. Chem. Soc.,* 2012, 134, 11767
Biedermann et al. *Chem. Eur. J.* 2010, 16, 13716
Bush, M. E. et al *J. Am. Chem. Soc.* 2005, 127, 14511
Caruso et al. *Science* 1998, 282, 1111
Chen et al. *Chem. Soc. Rev.* 2011, 40, 2254
Chu et al. *Langmuir* 2002, 18, 1856
Comiskey et al. *Nature* 1998, 394, 253
Cui et al. *Adv. Funct. Mater.* 2010, 20, 1625
De Cock et al *Angew. Chem. Int. Ed.* 2010, 49, 6954
Donath et al. *Angew. Chem. Int. Ed.* 1998, 37, 2201
Gunther et al. *Lab chip* 2006, 6, 1487
Heitmann et al. *J. Am. Chem. Soc.,* 2006, 128, 12574
Huebner et al. *Lab Chip* 2008, 8, 1244
Jeon et al. *Chem. Commun.* 2002, 38, 1828
Jiao et al. *Org. Lett.* 2011, 13, 3044
Jiao et al. *J. Am. Chem. Soc.,* 2010, 132, 15734
Jon et al. *Chemical Communications* 2001
Ke et al. *Angew. Chem.* 2011, 123, 3073
Kim et al. *J. Am. Chem. Soc.,* 2000, 122, 540
Lagona et al. *Angew. Chem. Int. Ed.,* 2005, 44, 4844
Lan et al. *Chem. Comm.* 2012, 48, 8757
Liu et al. *Chem. Eur. J.,* 2011, 17, 9930
Moghaddam et al. *J. Am. Chem. Soc.* 2011, 133, 3570
Nakamura et al. *J. Am. Chem. Soc.,* 2003, 125, 966
Patra et al., *Langmuir* 2009, 25, 13852
PCT/GB2012/051787
Peyratout et al. *Angew. Chem. Int. Ed.* 2004, 43, 3762
Priest et al. *Lab Chip* 2008, 8, 2182
Rauwald et al. *J. Phys. Chem.* 2010, 114, 8606
Rauwald et al. *Chem. Comm.* 2011, 47, 6000
Tamaki *Chem. Lett.,* 1984, 53
Theberge et al. *Angew. Chem. Int. Ed.* 2010, 49, 5846
US 2008/0199519
Utada et al. *Science* 2005, 308, 537
Waldeck *Chem. Rev.* 1991, 91, 415
Wang et al., *Chemistry of Materials* 2008, 20, 4194
Wu et al. *Phys. Rev. Lett.* 1998, 80, 4092
Wu *Chem. Eur. J.* 2009, 15, 11675
WO 2009/071899
WO 2013/014452
Xao et al *J. Phys. Chem B* 2011, 115, 13796
Ku et al. *AIChE Journal* 2006, 52, 3005
Yang et al. *J. Am. Chem. Soc.,* 2008, 130, 8574
Yang et al. *Lab Chip* 2009, 9, 961
Yang et al. *Angew. Chem.* 2011, 123, 497
Zha et al. *Adv. Mater.* 2002, 14, 1090
Zhang et al. *Science* 2012, 335, 690
Zhou et al. *Electrophoresis* 2009, 31, 2

The invention claimed is:

1. A nested capsule comprising a first capsule held within a second capsule, and each of the first and second capsules has a shell that is a supramolecular cross-linked network, wherein
   each shell is obtainable from the complexation of a composition comprising a host and one or more building blocks having suitable guest functionality, thereby to form a supramolecular cross-linked network, wherein the second capsule is not provided as a layer on the surface of the first capsule, and the supramolecular cross-linked network includes a non-covalent complex of the host and the one or more building blocks having suitable guest functionality.

2. The nested capsule according to claim 1, wherein the host is selected from cucurbituril, cyclodextrin, calix[n]arene, and crown ether compounds, and the one or more building blocks having suitable guest functionality for the cucurbituril, cyclodextrin, calix[n]arene, and crown ether hosts.

3. The nested capsule according to claim 2, wherein the host is a cucurbituril compound, and the one or more building blocks having suitable cucurbituril guest functionality.

4. The nested capsule according to claim 3, wherein the host is CB[8].

5. The nested capsule according to claim 1, wherein the shell of the first capsule is different to the shell of the second capsule.

6. The nested capsule according to claim 5, wherein a building block present in the shell of the first capsule is not present in the shell of the second capsule.

7. The nested capsule according to claim 1, wherein each capsule shell is obtainable from the complexation of (a) a composition comprising a host and (1) or (2); or (b) a composition comprising a plurality of covalently linked hosts and (1), (2) or (3), wherein:
   (1) comprises a first building block covalently linked to a plurality of first guest molecules and a second building block covalently linked to a plurality of second guest molecules, wherein a first guest molecule and a second guest molecule together with the host are suitable for forming a ternary guest-host complex;
   (2) comprises a first building block covalently linked to a plurality of first guest molecules and a plurality of second guest molecules, wherein a first and a second guest molecule together with the host are suitable for forming a ternary guest-host complex, optionally the composition further comprises a second building block covalently linked to one or more third guest molecules, one or more fourth guest molecules or both, wherein a third and a fourth molecule together with the host are suitable for forming a ternary guest-host complex, and/or the first and fourth molecules together with the host are suitable for forming a ternary guest-host complex, and/or the second and third molecules together with the host are suitable for forming a ternary guest-host complex;
(3) comprises a first building block covalently linked to a plurality of first guest molecules, wherein the first guest molecule together with the host are suitable for forming a binary guest-host complex.

8. The nested capsule according to claim 7, wherein each capsule shell is obtainable from the complexation of a composition comprising a host and (1) or (2).

9. The nested capsule according to claim 1, wherein one of the first and second capsules has a building block that is anionic, and the other of first and second capsules has a building block that is cationic.

10. The nested capsule according to claim 1, wherein one of the first and second capsules has two anionic building blocks.

11. The nested capsule according to claim 1, wherein one of the first and second capsules has two cationic building blocks.

12. The nested capsule according to claim 1, wherein the each of the first and second capsules has a building block that is a polymeric molecule.

13. A nested capsule according to claim 1, wherein the nested capsule holds an encapsulant.

14. The nested capsule according to claim 13, wherein the first capsule holds a first encapsulant and the second capsule holds a second encapsulant.

15. The nested capsule according to claim 14, wherein the first encapsulant is different to the second encapsulant.

16. The nested capsule according to claim 13, wherein the nested capsule holds an encapsulant that is a biomolecule.

17. The nested capsule according to claim 16, wherein the biomolecule has a detectable label.

18. A method of delivering an encapsulant to a location, the method comprising the steps of:
   (i) providing a nested capsule according to claim 13;
   (ii) delivering the nested capsule to a location; and
   (iii) permitting release of the encapsulated encapsulant from the nested capsule at the location.

19. The method of claim 18, wherein the encapsulant is held in the first capsule or the second capsule or both.

20. A method of delivering a plurality of encapsulants to one or more locations, the method comprising the steps of:
   (i) providing a nested capsule according to claim 14;
   (ii) delivering the nested capsule to a location;
   (iii) permitting release of the second encapsulant from the second capsule at a first location; and
   (iv) subsequently permitting release of the first encapsulant from the first capsule at the first location or a second location.

21. A method of delivering a plurality of encapsulants to a location, the method comprising the steps of:
   (i) providing a nested capsule according to claim 14;
   (ii) delivering the nested capsule to a location; and
   (iii) permitting release of the second encapsulant from the second capsule at a first location and simultaneously permitting release of the first encapsulant from the first capsule, thereby to deliver the first and second encapsulants to the location.

22. A method of synthesis, the method comprising the steps of:
   (i) providing a nested capsule according to claim 14, wherein the first and second encapsulants are interactable;
   (ii) permitting release of the first encapsulant from the first capsule into the second capsule, thereby to permit the first encapsulant to interact with the second encapsulant to yield a product; and
   (iii) optionally permitting the release of the product from the second capsule.

23. A method for the preparation of a nested capsule according to claim 1, the method comprising the steps of:
   (i) providing a first capsule, wherein the first capsule has a shell that is a supramolecular cross-linked network;
   (ii) encapsulating the first capsule within a shell of a second capsule, wherein the shell of the second capsule is a supramolecular cross-linked network, thereby to form a nested capsule.

24. A method for the preparation of a nested capsule according to claim 1, the method comprising the steps of:
   (i) providing a first droplet within a second droplet, wherein each of the first and second droplets has at its interface components suitable for forming a shell that is a supramolecular cross-linked network;
   (ii) permitting the components of the first and the second droplet to form a supramolecular cross-linked network, thereby to form a nested capsule.

25. The nested capsule according to claim 1, wherein each shell is a covalently cross-linked network, wherein the network is obtainable from the supramolecular cross-linked network by the ternary complexation of the composition comprising the host and one or more building blocks having suitable guest functionality, thereby to form the supramolecular cross-linked network, wherein the covalent cross-links are obtainable from the reaction of the guests held in the ternary complex.

26. A method of synthesising a nested capsule according to claim 1, the method comprising the steps of:
   (i) forming a first droplet of a first fluid in a continuous phase of a second fluid;
   (ii) forming a second droplet of the second fluid in a continuous phase of a third fluid, wherein the second droplet contains the first droplet or a capsule obtained therefrom;
   (iii) providing a first building block having guest functionality at the interface of the first fluid and the second fluid, and permitting the first building block to complex with a host at the interface;
   (iv) providing a second building block having guest functionality at the interface of the second fluid and the third fluid, and permitting the first building block to complex with a host at the interface.

* * * * *